(12) United States Patent
DeOrazio et al.

(10) Patent No.: US 6,828,341 B2
(45) Date of Patent: Dec. 7, 2004

(54) CYCLOHEXYLAMINE DERIVATIVES AS SUBTYPE SELECTIVE N-METHYL-D-ASPARTATE ANTAGONISTS

(75) Inventors: Russell Joseph DeOrazio, Schenectady, NY (US); Sham Shridhar Nikam, Ann Arbor, MI (US); Ian Leslie Scott, Delanson, NY (US); Brian Alan Sherer, Clifton Park, NY (US)

(73) Assignee: Warner-Lambert Company, Morris Plains, NJ (US)

(*) Notice: Subject to any disclaimer, the term of this patent is extended or adjusted under 35 U.S.C. 154(b) by 144 days.

(21) Appl. No.: 10/108,086

(22) Filed: Mar. 27, 2002

(65) Prior Publication Data

US 2003/0004212 A1 Jan. 2, 2003

Related U.S. Application Data

(60) Provisional application No. 60/279,169, filed on Mar. 27, 2001.

(51) Int. Cl.[7] .................... C07D 413/04; C07D 277/10; C07D 263/58; C07D 261/04; C07D 307/52
(52) U.S. Cl. ........................ 514/365; 548/229; 548/205; 548/240; 514/376; 514/378; 514/470; 549/466
(58) Field of Search .................. 548/229, 205, 548/240; 514/376, 365, 378, 470; 549/466

(56) References Cited

U.S. PATENT DOCUMENTS 6,015,824 A    1/2000   Alanine et al. ............. 514/375

FOREIGN PATENT DOCUMENTS

| EP | 0300272 | 1/1989 |
| EP | 0937458 | 8/1999 |
| EP | 0982026 | 3/2000 |
| WO | 9634864 | 11/1996 |
| WO | 9912924 | 3/1999 |
| WO | 9948891 | 9/1999 |
| WO | 0192239 | 12/2001 |

OTHER PUBLICATIONS

Yang, et al., "Diastereoselective [3+2] cycloadditions of a camphor-derived chiral N-acryloxylhydrazide with nitrile oxides: the preparation of optically pure Δ²-isoxazolines", Tetrahedron Letters, vol. 41, 2000, pp. 1453-1456.

European Search Report, EP 02 006 325.1.

Primary Examiner—Richard L. Raymond
Assistant Examiner—Hong Liu
(74) Attorney, Agent, or Firm—Suzanne M. Harvey; David R. Kurlandsky; Mehdi Ganjeizadeh

(57) ABSTRACT

Described are cyclohexylamine derivatives of Formula I

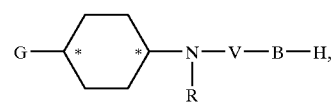

Formula VI

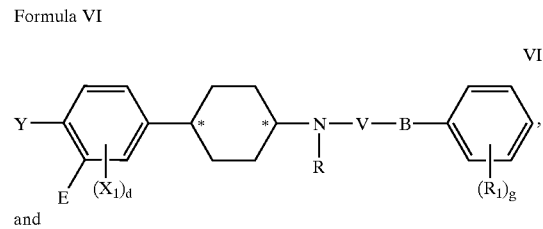

and

Formula VIa

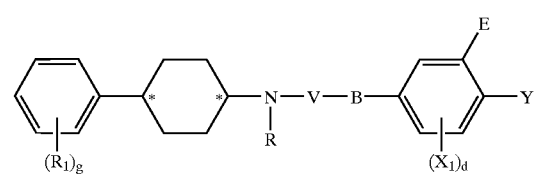

and pharmaceutically acceptable salts thereof, wherein $R_1$, g, *, R, V, B, E, Y, G, H, $X_1$, and d are as defined in the description. The compounds of Formulas I, VI, and VIa are antagonists of NMDA receptor channel complexes useful for treating cerebral vascular disorders such as, for example, stroke, cerebral ischemia, trauma, hypoglycemia, anxiety, migraine headache, convulsions, Parkinson's disease, aminoglycoside antibiotics-induced hearing loss, psychosis, glaucoma, CMV retinitis, opioid tolerance or withdrawal, chronic pain, or urinary incontinence.

10 Claims, No Drawings

CYCLOHEXYLAMINE DERIVATIVES AS SUBTYPE SELECTIVE N-METHYL-D-ASPARTATE ANTAGONISTS

This application claims priority to U.S. Ser. No. 60/279,169, filed Mar. 27, 2001, the entire contents of which are herein incorporated by reference.

FIELD OF THE INVENTION

The invention provides cyclohexylamine derivatives as N-Methyl-D-Aspartate (NMDA) antagonists, pharmacological compositions comprising the derivatives, and methods of treating diseases and disorders responsive to antagonism of NMDA receptors using the derivatives.

BACKGROUND OF THE INVENTION

Many of the physiological and pathophysiological effects of the endogenous excitatory neurotransmitter glutamate are mediated via actions at N-Methyl-D-Asparate (NMDA) receptors. Over-excitation of the NMDA receptors on postsynaptic cells—mediated by excessive release of glutamate from nerve endings or glial cells—results in a massive calcium ion influx through a calcium ion channel into neuronal cells, leading to neuronal cell death. These events occur under ischemic or hypoxic conditions such as, for example, stroke, hypoglycemia, cardiac arrest, or acute physical trauma.

NMDA receptors in vivo form an NMDA receptor channel complex in cell walls comprising at least three binding domains, including a glutamic acid (or NMDA) recognition site, a channel blocking binding site, and a strychnine-insensitive glycine binding site. Physiologically, a blockade of at least one of these sites terminates the channel opening of the NMDA receptor, thereby preventing calcium ion influx into cells. Accordingly, an NMDA receptor antagonist is therapeutically useful because it minimizes damage to the central nervous system induced by calcium ion influx under ischemic or hypoxic conditions.

A functional NMDA receptor is comprised of the combination of at least one subunit termed "NR1," which has 8 splice variants including NR1A, and one (or more) subunit termed "NR2A," "NR2B," "NR2C," and "NR2D." The combinations are designated NR1/2A, NR1/2B, NR1/2C and NR1/2D, respectively. The different NR2 subunits have distinct developmental and anatomical distributions. This suggests that agents that selectively antagonize one NR1/NR2 combination would have therapeutic actions without the psychotomimetic or dysphoric side effects associated with antagonists which block multiple NR1/NR2 combinations.

A subtype-selective NMDA receptor antagonist may be identified by methods well-known in the pharmaceutical arts, such as, for example, screening compounds in an electrophysiology assay. In one such electrophysiology assay, different subunit combinations of recombinant NR1 and NR2 receptors are expressed in Xenopus oocytes, and a potential agent is administered at different concentrations. NMDA-based electrical currents are activated by co-administration of fixed concentrations of an excitatory amino acid such as, for example, glutamic acid or glycine. The ability of an agent to antagonize the activation of the electrical current by an excitatory amino acid is measured by recording the change in the current versus the change in the concentration of the agent.

Screening of compounds in recent years have identified a number of NMDA receptor antagonists that have been used in animal and clinical human studies to demonstrate proof of concept for use of such an antagonist in the treatment of a variety of disorders. Disorders known to be responsive to blockade of NMDA receptors include acute cerebral ischemia (stroke or cerebral trauma, for example), muscular spasm, convulsive disorders, pain, including chronic and neuropathic pain, anxiety, and chronic neurodegenerative disorders such as Parkinson's disease. NMDA receptor antagonists may also be used to prevent tolerance to opiate analgesia or to help control symptoms of withdrawal from addictive drugs. In fact, excessive excitation by neurotransmitters may be responsible for the loss of neurons in a wide variety of conditions. Additional conditions include cerebral vascular disorders such as cerebral ischemia or cerebral infarction resulting in a range of conditions such as thromboembolic or hemorrhagic stroke, cerebral vasospasm, hypoglycemia, cardiac arrest, status epilepticus, perinatal, asphyxia anoxia, such as from near drowning, pulmonary surgery and cerebral trauma, as well as lathyrism, Alzheimer's disease, and Huntington's disease. Other conditions amendable to treatment with an subtype-selective NMDA receptor antagonist include amyotrophic lateral sclerosis (ALS), epilepsy, and schizophrenia.

For example, studies have demonstrated that compounds that act as antagonists at NMDA receptors have beneficial pharmacological effects on patients suffering from Parkinson's disease. In Parkinson's disease, there is a loss of dopamine neurons in the substantia nigra. Secondary to this dopamine loss is a hyperactivity of specific brain glutamatergic pathways. This glutamatergic hyperactivity is thought to mediate some of the pathophysiological aspects of Parkinson's disease, as well as some of the side effects associated with the long-term treatment of the disease by dopamine agonists, such as L-DOPA, pergolide, ropinirole, or pramipexole. Clinical studies in humans have demonstrated that antagonists at NMDA receptors have beneficial effects in Parkinson's disease or in treating the side effects associated with the treatment of Parkinson's disease with dopamine agonists.

Pain is another example of a condition shown to be responsive to NMDA receptor antagonism. For example in previous studies, stimulation of NMDA receptors by afferent nerves transmitting painful stimuli has been demonstrated to be involved in hyperalgesic and neuropathic pain states. Animal studies have demonstrated that compounds that act as antagonists at NMDA receptors have beneficial effects in treating hyperalgesic and neuropathic pain states.

However, while NMDA antagonists have been successfully used to demonstrate the proof of concept mentioned above, very few, if any, of these antagonists have shown a suitable drug profile in clinical studies. This is so even though numerous NMDA receptor antagonists have been synthesized and tested.

The difficulty referenced above with demonstrating clinical utility of NMDA receptor antagonists has been the antagonists' lack of NMDA receptor subtype selectivity and/or biological activity when dosed orally. Before the present invention, many of the drugs of the NMDA receptor antagonist class were nonselective antagonists of NMDA receptor subtypes that were administered intravenously (IV), which accounts for their undesired side effects and the present need for selective, orally efficacious agents, respectively. Given that the need for medicinal agents that treat diseases responsive to antagonism of NMDA receptors remains unmet, the search for NMDA receptor antagonists that are subtype-selective and orally efficacious continues.

We have discovered a series of novel cyclohexylamines that are subtype-selective NMDA receptor antagonists and are efficacious in vivo when dosed orally. All that is needed to practice the invention is to administer from 1 to 6 times daily to a patient in need thereof, a therapeutically effective amount of a compound of the invention. As is discussed below, determination of dosage forms and amounts of the invention compounds, routes of administration, and identification of patients in need of treatment, is within the average skill in the pharmaceutical and medical arts.

SUMMARY OF THE INVENTION

One embodiment of the present invention is a compound of Formula I

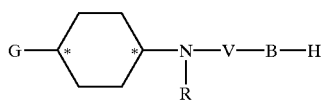

I and pharmaceutically acceptable salts thereof, wherein:

* means cis or trans or mixtures thereof;
G and H are

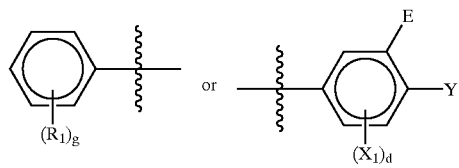

but are never the same;
R is hydrogen, alkyl, substituted alkyl, alkenyl, substituted alkenyl, $C(O)R_2$, $C(O)OR_2$, $C(O)NHR_2$, aralkyl, hydroxyalkyl, aminoalkyl, amino (hydroxy) alkyl, alkylaminoalkyl, carboxyalkyl, or $OR_2$ wherein $R_2$ is alkyl alkenyl or aralkyl;
$R_1$ is independently selected from alkyl, substituted alkyl, alkenyl, substituted alkenyl, alkoxy, substituted alkoxy, alkylaminoalkyl, hydroxyalkyl, (aminocarbonyl)-alkyl, (alkylthio)-alkyl, carboxyalkyl, haloalkyl, and halogen;
g is an integer of from 0 to 3;
V is $(CH_2)_n$ or $(CH_2)_m$—C=O, wherein n is an integer of from 1 to 4, and m is an integer of from 0 to 4;
$X_1$ is alkyl, substituted alkyl, alkenyl, substituted alkenyl, alkoxy, substituted alkoxy, aralkyl, substituted aralkyl, halogen, haloalkyl, cyano, nitro, amino, aminoalkyl, alkylaminoalkyl, hydroxyalkyl, carboxyalkyl, (aminocarbonyl)-alkyl, (alkylthio)-alkyl, or C(O)-alkyl;
d is an integer of from 0 to 2;
E is hydrogen; and
Y is OH; or
E and Y may be taken together with the phenylene to which they are attached to form a fused 9- or 10-membered bicyclic ring, containing from 0 to 3 heteroatoms in E—Y selected from N, O, and S, wherein E is a linker group containing 2 or 3 atoms of the bicyclic ring, and Y is a hydrogen bond donor group containing 1 atom of the bicyclic ring; and
B is a 4-, 5-, or 6-membered, carbon-linked heterocyclene, containing from 1 to 3 heteroatoms, which are N, O, or S, selected from the group consisting of:

(i) 1-aza-2-cyclobutanon-3,4-diyl of formula

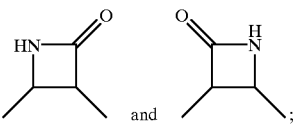

and ;

(ii) a 5-membered aromatic, nonaromatic dihydro, or nonaromatic tetrahydro diradical heterocyclic ring having carbon atoms and from 1 to 3 heteroatoms selected from N, O, and S;

(iii) a 5-membered oxo-substituted, nonaromatic tetrahydro, diradical heterocyclic ring having carbon atoms and 1 or 2 heteroatoms selected from N, O, and S;

(iv) a 6-membered aromatic, nonaromatic tetrahydro, or nonaromatic hexahydro diradical heterocyclic ring having carbon atoms and 1 or 2 heteroatoms, which heteroatoms are nitrogen, and (v) a 6-membered nonaromatic oxo-substituted hexahydro diradical heterocyclic ring having carbon atoms and 1 or 2 heteroatoms which are nitrogen and 0 or 1 heteroatom which is oxygen wherein the atoms of the heterocyclene ring that are bonded to the group V and the phenyl bearing the group $(X_1)_d$ are carbon atoms, and further wherein when B is a nonaromatic heterocycle containing sulfur, said sulfur may further comprise

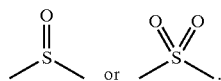

Preferred are compounds of Formula II

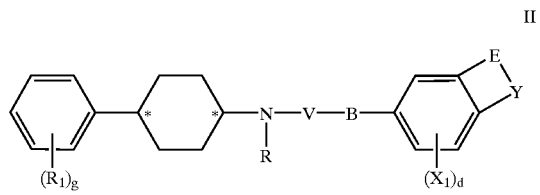

II and pharmaceutically acceptable salts thereof wherein *, $R_1$, g, R, $X_1$, and d are as defined above for Formula I;

B is a heterocyclene selected from the group consisting of:

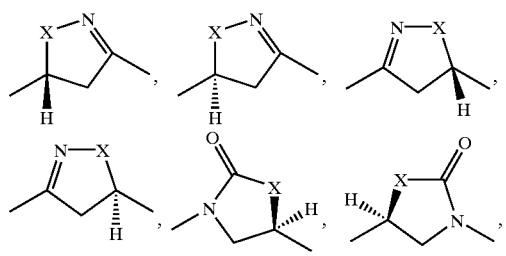

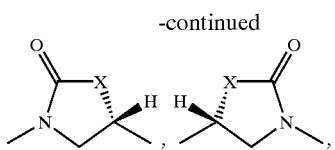

wherein X is O, S, or N—R₃ wherein R₃ is hydrogen or alkyl;
E and Y are taken together with the phenylene to which they are attached to form a fused 9- or 10-membered bicyclic ring, containing from 0 to 3 heteroatoms in E—Y selected from N, O, and S, wherein E is a linker group containing 2 or 3 atoms of the bicyclic ring, and Y is a hydrogen bond donor group containing 1 atom of the bicyclic ring;
V is CH₂; and
one X₁ is ortho to B and para to E.

More preferred are compounds of Formula II and pharmaceutically acceptable salts thereof wherein Y is selected from —N(H)—, —CH(OH)—, and —N(OH)—, and
E is selected from —CH=CH—, —CH₂—CH₂—, —CH=N—, —C(O)—CH₂—, —CH₂—C(O)—, —CH₂—S(O)—, —CH₂—S(O)₂—, —N=C(H)—, —N(H)—C(O)—, —O—C(O)—, —S—C(O)—, —N=N—, —CH=CH—C(H)—, —CH₂—CH₂—CH₂—, —CH₂—CH₂—C(O)—, —CH₂—CH₂—S(O)—, —CH₂—CH₂—S(O)₂—, —CH=CH—C(O)—, —N=CH—C(O)—, —O—CH₂—C(O)—, —S—CH₂—C(O)—, and —N(H)—C(O)—C(O)—; or
Y is selected from =C(OH)—; and
E is selected from —CH=CH—C(H)=, —C(O)—C(H)=, —C(O)—N=, —O—N=, —S—N=, —C(O)—N(H)—N=, —CH=N—N=, —CH=N(O)—N=, and —N(H)—C(O)—N=.

Still more preferred are compounds of Formula II and pharmaceutically acceptable salts thereof wherein —E—Y— is selected from the group consisting of
—CH=CH—N(H)—,
—(CH₂)₂—N(H)—,
—CH=N—N(H)—,
—C(O)—CH₂—N(H)—,
—CH₂—C(O)—N(H)—,
—CH₂—S(O)—N(H)—,
—CH₂—S(O)₂—N(H)—,
—CH=CH—CH(OH)—,
—(CH₂)₂—CH(OH)—,
—C(O)—C(H)=C(OH)—,
—C(O)—N=C(OH)—,
—N=CH—N(H)—,
—N(H)—C(O)—N(H)—,
—O—C(O)—NH—,
—S—C(O)—NH—,
—O—N=CH(OH)—,
—S—N=CH(OH)—,
—N=N—N(H)—,
—N=N—N(OH)—,
—CH=CH—CH=C(OH)—,
—(CH₂)₃—CH(OH)—,
—(CH₂)₂—C(O)—N(H)—,
—(CH₂)₂—S(O)—N(H)—,
—(CH₂)₂—S(O)₂—N(H)—,
—CH=CH—C(O)—N(H)—,
—C(O)—NH—N=C(OH)—,
—CH=N—N=C(OH)—,
—CH=N(O)—N=C(OH)—,
—N(H)—C(O)—N=C(OH)—,
—N=CH—C(O)—NH—,
—O—CH₂—C(O)—NH—,
—S—CH₂—C(O)—NH—, and
—N(H)—C(O)—C(O)—N(H)—.

Also preferred are compounds of Formula III

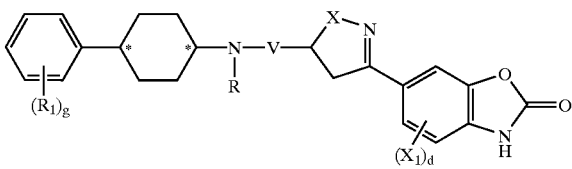

and pharmaceutically acceptable salts thereof, wherein *, R₁, g, R, X₁, d, and V are as defined above for Formula I, and X is O, S, or N—R₃ wherein R₃ is hydrogen or alkyl.

More preferred is a compound of Formula III and a pharmaceutically acceptable salt thereof, which is trans-6-(5-{[methyl-4-phenyl-cyclohexyl)-amino]-methyl-4,5-dihydro-isoxazol-3-yl}-3H-benzoxazol-2-one.

Also preferred are compounds of Formula IV

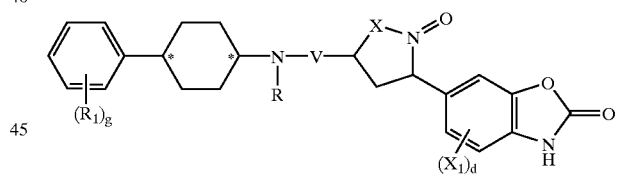

and pharmaceutically acceptable salts thereof, wherein *, R₁, g, R, X₁, d, and V are as defined above for Formula I, and X is O, S, or N—R₃ wherein R₃ is hydrogen or alkyl.

More preferred is a compound of Formula IV and pharmaceutically acceptable salts thereof, selected from the group consisting of:
trans-6-{5-[4-(4-fluoro-phenyl)-cyclohexylamino]methyl-2-oxo-oxazolidin-3-yl}-3H-benzoxazol-2-one;
trans-6-{5-[4-(4-fluoro-phenyl)-cyclohexylamino]methyl-2-oxo-oxazolidin-3-yl}-3H-benzoxazol-2-one hydrochloride;
trans-6-(5-{[4-(4-fluoro-phenyl)-cyclohexyll-methyl-amino}methyl-2-oxo-oxazolidin-3-yl)-3H-benzoxazol-2-one; and
trans-6-(5-{[4-(4-fluoro-phenyl)-cyclohexyll-methyl-amino}methyl-2-oxo-oxazolidin-3-yl)-3H-benzoxazol-2-one hydrochloride.

Also preferred are compounds of Formula V

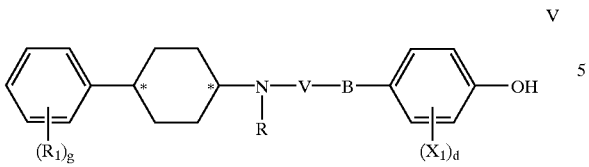

and pharmaceutically acceptable salts thereof, wherein *, $R_1$, g, R, V, B, $X_1$, and d are as defined above for Formula I.

Another embodiment of the present invention is a compound of Formulae VI and VIa

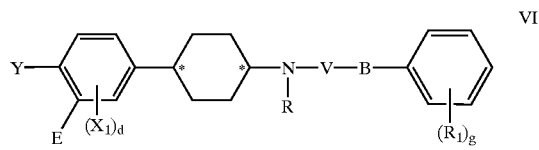

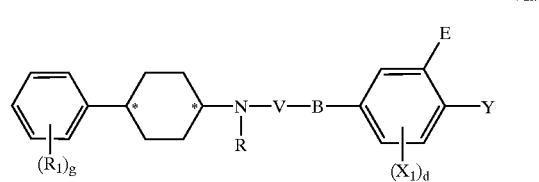

and pharmaceutically acceptable salts thereof, wherein

* means cis or trans or mixtures thereof;
R is hydrogen, alkyl, substituted alkyl, alkenyl, substituted alkenyl, $C(O)R_2$, $C(O)OR_2$, $C(O)NHR_2$, aralkyl, hydroxyalkyl, aminoalkyl, amino (hydroxy) alkyl, alkylaminoalkyl, carboxyalkyl, or $OR_2$ wherein $R_2$ is alkyl, alkenyl or aralkyl;
$R_1$ is independently selected from alkyl, substituted alkyl, alkenyl, substituted alkenyl, alkoxy, substituted alkoxy, alkylaminoalkyl, hydroxyalkyl, (aminocarbonyl)-alkyl, (alkylthio)-alkyl, carboxyalkyl, haloalkyl, and halogen;
g is an integer of from 0 to 3;
V is $(CH_2)_n$ or $(CH_2)_m$—C=O, wherein n is an integer of from 1 to 4, and m is an integer of from 0 to 4;
$X_1$ is alkyl, substituted alkyl, alkenyl, substituted alkenyl, alkoxy, substituted alkoxy, aralkyl, substituted aralkyl, halogen, haloalkyl, cyano, nitro, amino, aminoalkyl, alkylaminoalkyl, hydroxyalkyl, carboxyalkyl, (aminocarbonyl)-alkyl, (alkylthio)-alkyl, or C(O)-alkyl;
d is an integer of from 0 to 2;
E is hydrogen; and
Y is OH; or
E and Y may be taken together with the phenylene to which they are attached to form a fused 9- or 10-membered bicyclic ring, containing from 0 to 3 heteroatoms in E—Y selected from N, O, and S, wherein E is a linker group containing 2 or 3 atoms of the bicyclic ring, and Y is a hydrogen bond donor group containing 1 atom of the bicyclic ring; and
B is a 4-, 5-, or 6-membered, carbon-linked heterocyclene, containing from 1 to 3 heteroatoms, which are N, O, or S, selected from the group consisting of:

(i) 1-aza-2-cyclobutanon-3,4-diyl of formula

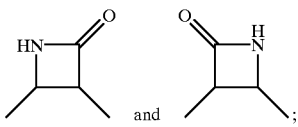

and                ;

(ii) a 5-membered aromatic, nonaromatic dihydro, or nonaromatic tetrahydro diradical heterocyclic ring having carbon atoms and from 1 to 3 heteroatoms selected from N, O, and S;
(iii) a 5-membered oxo-substituted, nonaromatic tetrahydro, diradical heterocyclic ring having carbon atoms and 1 or 2 heteroatoms selected from N, O, and S;
(iv) a 6-membered aromatic, nonaromatic tetrahydro, or nonaromatic hexahydro diradical heterocyclic ring having carbon atoms and 1 or 2 heteroatoms, which heteroatoms are nitrogen, and
(v) a 6-membered nonaromatic oxo-substituted hexahydro diradical heterocyclic ring having carbon atoms and 1 or 2 heteroatoms which are nitrogen and 0 or 1 heteroatom which is oxygen wherein the atoms of the heterocyclene ring that are bonded to the group V and the phenyl bearing the group $(X_1)_d$ are carbon atoms, and further wherein when B is a nonaromatic heterocycle containing sulfur, said sulfur may further comprise

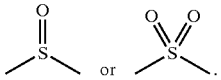

Preferred are compounds of Formula VII

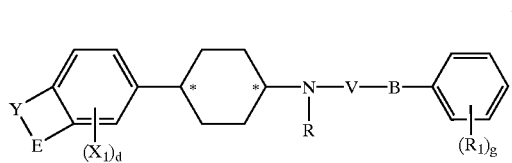

and pharmaceutically acceptable salts thereof, wherein

*, $R_1$, g, R, $X_1$, and d are as defined above for Formula VI;
B is a heterocyclene selected from the group consisting of:

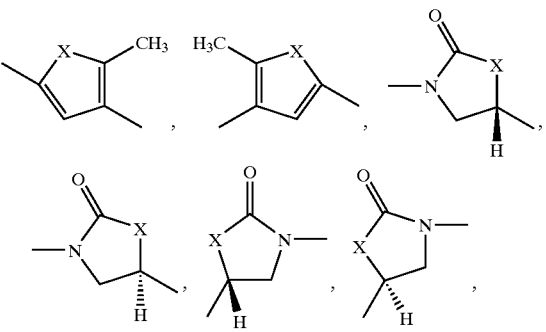

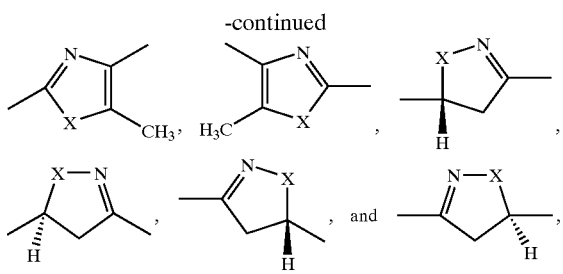

X is O, S, or N—R₃ wherein R₃ is hydrogen or alkyl;
V is CH₂;
E and Y are taken together with the phenylene to which they are attached to form a fused 9- or 10-membered bicyclic ring, containing from 0 to 3 heteroatoms in E—Y selected from N, O, and S, wherein E is a linker group containing 2 or 3 atoms of the bicyclic ring, and Y is a hydrogen bond donor group containing 1 atom of the bicyclic ring; and one $X_1$ is ortho to B and para to E.

More preferred are compounds of Formula VII and pharmaceutically acceptable salts thereof wherein Y is selected from —N(H)—, —CH(OH)—, and —N(OH)—, and
E is selected from —CH=CH—, —CH₂—CH₂—, —CH=N—, —C(O)—CH₂—, —CH₂—C(O)—, —CH₂—S(O)—, —CH₂—S(O)₂—, —N=C(H)—, —N(H)—C(O)—, —O—C(O)—, —S—C(O)—, —N=N—, —CH=CH—C(H)—, —CH₂—CH₂—CH₂—, —CH₂—CH₂—C(O)—, —CH₂—CH₂—S(O)—, —CH₂—CH₂—S(O)₂—, —CH=CH—C(O)—, —N=CH—C(O)—, —O—CH₂—C(O)—, —S—CH₂—C(O)—, and —N(H)—C(O)—C(O)—; or
Y is selected from =C(OH)—; and
E is selected from —CH=CH—C(H)=, —C(O)—C(H)=, —C(O)—N=, —O—N=, —S—N=, —C(O)—N(H)—N=, —CH=N—N=, —CH=N(O)—N=, and —N(H)—C(O)—N=.

Still more preferred are compounds of Formula VII and pharmaceutically acceptable salts thereof wherein —E—Y— is selected from the group consisting of
—CH=CH—N(H)—,
—(CH₂)₂—N(H)—,
—CH=N—N(H)—,
—C(O)—CH₂—N(H)—,
—CH₂—C(O)—N(H)—,
—CH₂—S(O)—N(H)—,
—CH₂—S(O)₂—N(H)—,
—CH=CH—CH(OH)—,
—(CH₂)₂—CH(OH)—,
—C(O)—C(H)=C(OH)—,
—C(O)—N=C(OH)—,
—N=CH—N(H)—,
—N(H)—C(O)—N(H)—,
—O—C(O)—NH—,
—S—C(O)—NH—,
—O—N=CH(OH)—,
—S—N=CH(OH)—,
—N=N—N(H)—,
—N=N—N(OH)—,
—CH=CH—CH=C(OH)—,
—(CH₂)₃—CH(OH)—,
—(CH₂)₂—C(O)—N(H)—,
—(CH₂)₂—S(O)—N(H)—,
—(CH₂)₂—S(O)₂—N(H)—,
—CH=CH—C(O)—N(H)—,
—C(O)—NH—N=C(OH)—,
—CH=N—N=C(OH)—,
—CH=N(O)—N=C(OH)—,
—N(H)—C(O)—N=C(OH)—,
—N=CH—C(O)—NH—,
—O—CH₂—C(O)—NH—,
—S—CH₂—C(O)—NH—, and
—N(H)—C(O)—C(O)—N(H)—.

Also preferred are compounds of Formula VIII

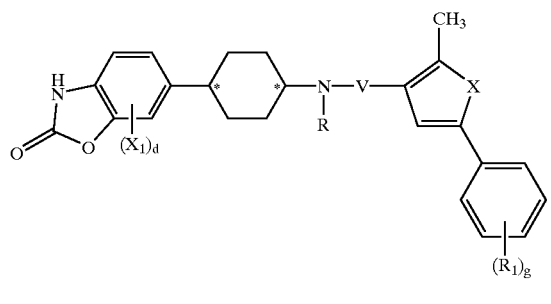

and pharmaceutically acceptable salts thereof, wherein $X_1$, d, *, R, V, $R_1$, and g are as defined above for Formula VI, and X is O, S, or N—R₃ wherein R₃ is hydrogen or alkyl.

More preferred is a compound of Formula VIII and a pharmaceutically acceptable salt thereof which is trans-6-{4-[methyl-(2-methyl-5-phenyl-furan-3-ylmethyl)-amino]-cyclohexyl}-3H-benzoxazol-2-one.

Also preferred are compounds of Formula IX

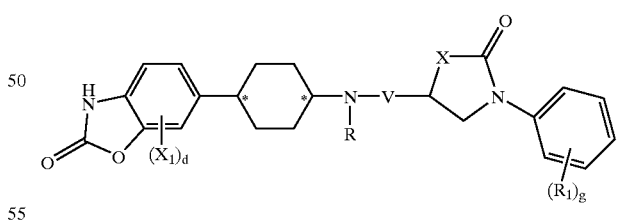

and pharmaceutically acceptable salts thereof, wherein $X_1$, d, *, R, V, $R_1$, and g are as defined above for Formula VI, and X is O, S, or N—R₃ wherein R₃ is hydrogen or alkyl.

More preferred is a compound of Formula IX and a pharmaceutically acceptable salt thereof, selected from the group consisting of:
trans-(R)-6-{4-[(2-oxo-3-phenyl-oxazolidin-5-ylmethyl)amino]-cyclohexyl}-3H-benzoxazol-2-one;
trans-(R)-6-{4-[methyl-(2-oxo-3-phenyl-oxazolidin-5-ylmethyl)amino]-cyclohexyl}-3H-benzoxazol-2-one.

Also preferred are compounds of Formula X

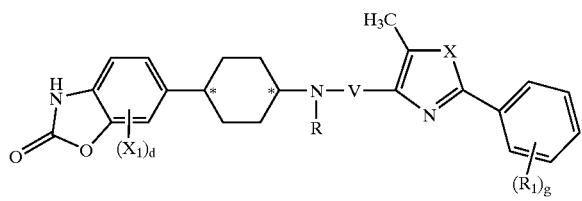

and pharmaceutically acceptable salts thereof, wherein $X_1$, d, R, V, $R_1$, and g are as defined above for Formula VI, and X is O, S, or N—$R_3$ wherein $R_3$ is hydrogen or alkyl.

More preferred is a compound of Formula X and a pharmaceutically acceptable salt thereof, selected from the group consisting of:
trans-6-{4-[(5-methyl-2-phenyl-thiazol-4-ylmethyl)-amino]-cyclohexyl}-3H-benzoxazol-2-one; and
trans-6-{4-(methyl-(5-methyl-2-phenyl-thiazol-4-ylmethyl)-amino]-cyclohexyl}-3H-benzoxazol-2-one.

Also preferred are compounds of Formula XI

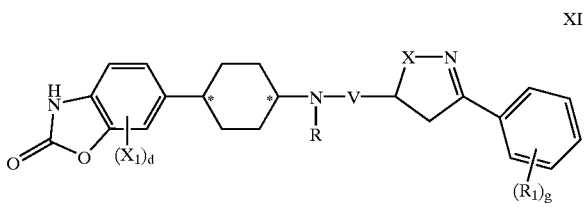

and pharmaceutically acceptable salts thereof, wherein $X_1$, d, *, R, V, $R_1$, and g are as defined above for Formula VI, and X is O, S, or N—$R_3$ wherein $R_3$ is hydrogen or alkyl.

More preferred is a compound of Formula XI and a pharmaceutically acceptable salt thereof, selected from the group consisting of:
trans-6-(4-{[3-(4-fluoro-phenyl)-4,5-dihydro-isoxazol-5-ylmethyl]-amino}-cyclohexyl)-3H-benzoxazol-2-one; and
trans-6-(4-{[3-(4-fluoro-phenyl)-4,5-dihydro-isoxazol-5-ylmethyl]-methyl-amino}-cyclohexyl)-3H-benzoxazol-2-one.

Also preferred are compounds of Formula XII

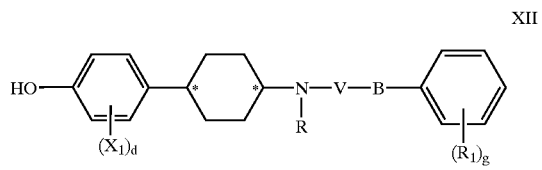

and pharmaceutically acceptable salts thereof, wherein $X_1$, d, R, *, $R_1$, g, V, and B are as defined above for Formula VI.

The invention also provides a pharmaceutical composition, comprising a therapeutically effective amount of a compound of Formula I, or a pharmaceutically acceptable salt thereof, together with a pharmaceutically acceptable diluent, carrier, or excipient.

In a preferred embodiment, the invention provides a pharmaceutical composition, comprising a therapeutically effective amount of a compound of Formula I, or a pharmaceutically acceptable salt thereof, selected from the group consisting of:
trans-6-(5-{[methyl-(4-phenyl-cyclohexyl)-amino]-methyl}-4,5-dihydro-isoxazol-3-yl)-3H-benzoxazol-2-one;
trans-6-{5-[4-(4-fluoro-phenyl)-cyclohexylamino]-methyl-2-oxo-oxazolidin-3-yl}-3H-benzoxazol-2-one; and
trans-6-(5-[{4-(4-fluoro-phenyl)-cyclohexyl]-methyl-amino}-methyl-2-oxo-oxazolidin-3-yl)-3H-benzoxazol-2-one;
together with a pharmaceutically acceptable diluent, carrier, or excipient.

The invention also provides a pharmaceutical composition, comprising a therapeutically effective amount of a compound of Formula VI, or a pharmaceutically acceptable salt thereof, together with a pharmaceutically acceptable diluent, carrier, or excipient.

In a preferred embodiment, the invention provides a pharmaceutical composition, comprising a therapeutically effective amount of a compound of Formula VI, or a pharmaceutically acceptable salt thereof, selected from the group consisting of:
trans-6-{4-[methyl-(2-methyl-5-phenyl-furan-3-ylmethyl)-amino]-cyclohexyl}-3H-benzoxazol-2-one;
trans-(R)-6-{4-[2-oxo-3-phenyl-oxazolidin-5-ylmethyl)-amino]-cyclohexyl}-3H-benzoxazol-2-one;
trans-(R)-6-{4-[methyl-(2-oxo-3-phenyl-oxazolidin-5-ylmethyl)-amino]-cyclohexyl}-3H-benzoxazol-2-one;
trans-6-{4-[(5-methyl-2-phenyl-thiazol-4-ylmethyl)-amino]-cyclohexyl}-3H-benzoxazol-2-one;
trans-6-{4-[methyl-(5-methyl-2-phenyl-thiazol-4-ylmethyl)-amino]-cyclohexyl}-3H-benzoxazol-2-one;
trans-6-(4-{[3-(4-fluoro-phenyl)-4,5-dihydro-isoxazol-5-ylmethyl]-amino}-cyclohexyl)-3H-benzoxazol-2-one; and
trans-6-(4-{[3-(4-fluoro-phenyl)-4,5-dihydro-isoxazol-5-ylmethyl]-methyl-amino}-cyclohexyl)-3H-benzoxazol-2-one;
together with a pharmaceutically acceptable diluent, carrier, or excipient.

The invention also provides a method of treating disorders responsive to the selective blockade of the N-methyl-D-aspartate receptor subtypes in a mammal, including a human, suffering therefrom, which comprises administering a therapeutically effective amount of a compound of Formula I, or a pharmaceutically acceptable salt thereof.

In a preferred embodiment, the invention provides a method of treating disorders responsive to the selective blockade of the N-methyl-D-aspartate receptor subtypes in a mammal, including a human, suffering therefrom, comprising administering a compound of Formula I, or a pharmaceutically acceptable salt thereof, wherein the disorder being treated is selected from stroke, cerebral ischemia, depression, trauma, hypoglycemia, anxiety, migraine headache, convulsions, aminoglycoside antibiotics-induced hearing loss, psychosis, glaucoma, CMV retinitis, opioid tolerance or withdrawal, pain, including chronic pain, neuropathic pain, or surgical pain, and urinary incontinence.

In a more preferred embodiment, the invention provides a method of treating disorders responsive to the selective blockade of the N-methyl-D-aspartate receptor subtypes in a mammal, including a human, suffering therefrom comprising administering a compound of Formula I, or a pharmaceutically acceptable salt thereof, wherein the disorder being treated is pain.

In another more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, wherein the disorder being treated is Parkinson's disease.

In a still more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, selected from the group consisting of:

trans-6-(5-{[methyl-(4-phenyl-cyclohexyl)-amino]-methyl}-4,5-dihydro-isoxazol-3-yl)-3H-benzoxazol-2-one;

trans-6-{5-[4-(4-fluoro-phenyl)-cyclohexylamino]-methyl-2-oxo-oxazolidin-3-yl}-3H-benzoxazol-2-one; and trans-6-(5-{[4-(4-fluoro-phenyl)-cyclohexyl]-methyl-amino}-methyl-2-oxo-oxazolidin-3-yl)-3H-benzoxazol-2-one;

together with a pharmaceutically acceptable diluent, carrier, or excipient.

In another more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, further comprising administering a dopamine agonist.

In another more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, further comprising administering a dopamine agonist wherein said dopamine agonist is L-DOPA.

In another preferred embodiment, the invention provides a method of treating disorders comprising administering a compound of Formula I or a pharmaceutically acceptable salt thereof in unit dosage form.

The invention also provides a method of treating disorders responsive to the selective blockade of the N-methyl-D-aspartate receptor subtypes in a mammal, including a human, suffering therefrom which comprises administering a compound of Formula VI or a pharmaceutically acceptable salt thereof.

In a preferred embodiment, the invention provides a method of treating disorders responsive to the selective blockade of the N-methyl-D-aspartate receptor subtypes in a mammal, including a human, suffering therefrom comprising administering a compound of Formula VI or a pharmaceutically acceptable salt thereof, wherein the disorder being treated is selected from stroke, cerebral ischemia, depression, trauma, hypoglycemia, anxiety, migraine headache, convulsions, aminoglycoside antibiotics-induced hearing loss, psychosis, glaucoma, CMV retinitis, opioid tolerance or withdrawal, pain, including chronic pain, neuropathic pain, or surgical pain, and urinary incontinence.

In a more preferred embodiment, the invention provides a method of treating disorders responsive to the selective blockade of the N-methyl-D-aspartate receptor subtypes in a mammal, including a human, suffering therefrom comprising administering a compound of Formula VI or a pharmaceutically acceptable salt thereof, wherein the disorder being treated is pain.

In another more preferred embodiment, the invention provides a method of treating disorders responsive to the selective blockade of the N-methyl-D-aspartate receptor subtypes in a mammal, including a human, suffering therefrom comprising administering a compound of Formula VI or a pharmaceutically acceptable salt thereof, wherein the disorder being treated is Parkinson's disease.

In a still more preferred embodiment, the invention provides a method of treating disorders responsive to the selective blockade of the N-methyl-D-aspartate receptor subtypes in a mammal, including a human, suffering therefrom comprising administering a compound of Formula VI or a pharmaceutically acceptable salt thereof, selected from the group consisting of:

trans-6-{4-[methyl-(2-methyl-5-phenyl-furan-3-ylmethyl)-amino]-cyclohexyl}-3H-benzoxazol-2-one;

trans-(R)-6-{4-[2-oxo-3-phenyl-oxazolidin-5-ylmethyl)-amino]-cyclohexyl}-3H-benzoxazol-2-one;

trans-(R)-6-{4-[methyl-(2-oxo-3-phenyl-oxazolidin-5-ylmethyl)-amino]-cyclohexyl}-3H-benzoxazol-2-one;

trans-6-{4-[(5-methyl-2-phenyl-thiazol-4-ylmethyl)-amino]-cyclohexyl}-3H-benzoxazol-2-one;

trans-6-{4-[methyl-(5-methyl-2-phenyl-thiazol-4-ylmethyl)-amino]-cyclohexyl}-3H-benzoxazol-2-one;

trans-6-(4-{[3-(4-fluoro-phenyl)-4,5-dihydro-isoxazol-5-ylmethyl]-amino}-cyclohexyl)-3H-benzoxazol-2-one; and trans-6-(4-{[3-(4-fluoro-phenyl)-4,5-dihydro-isoxazol-5-ylmethyl]-methyl-amino}-cyclohexyl)-3H-benzoxazol-2-one;

together with a pharmaceutically acceptable diluent, carrier, or excipient.

In another more preferred embodiment, the invention provides a method of treating disorders responsive to the selective blockade of the N-methyl-D-aspartate receptor subtypes in a mammal, including a human, suffering therefrom comprising administering a compound of Formula VI or a pharmaceutically acceptable salt thereof, further comprising administering a dopamine agonist.

In another more preferred embodiment, the invention provides a method of treating disorders responsive to the selective blockade of the N-methyl-D-aspartate receptor subtypes in a mammal, including a human, suffering therefrom comprising administering a compound of Formula VI or a pharmaceutically acceptable salt thereof, further comprising administering a dopamine agonist wherein said dopamine agonist is L-DOPA.

In another preferred embodiment, the invention provides a method of treating disorders comprising administering a compound of Formula VI or a pharmaceutically acceptable salt thereof in unit dosage form.

Another embodiment of the present invention is a compound selected from the group consisting of:

6-(cyclohexanone-4-yl)benzoxazolin-2-one;

3-(3-benzyloxy-4-nitro-phenyl)-5-[methyl-(4-phenyl-cyclohexyl)-amino]methyl-4,5-dihydro-isoxazole;

3-(4-amino-3-hydroxy-phenyl)-5-[methyl-(4-phenyl-cyclohexyl)-amino]methyl-4,5-dihydro-isoxazole;

3-(methylamino)methyl-2-methyl-5-phenyl-furan;

5-(aminomethyl)-3-phenyl-2-oxo-oxazolidine;

6-[5-(aminomethyl)-2-oxo-oxazolidin-3-yl]-3H-benzoxazol-2-one;

4-(aminomethyl)-5-methyl-2-phenyl-thiazole; and 5-(aminomethyl)-3-(4-fluorophenyl)-4,5-dihydro-isoxazole.

Another embodiment of the present invention is a method of preparing compounds of Formula I and pharmaceutically acceptable salts thereof, wherein V is $(CH_2)_n$ wherein n is an integer of from 1 to 4 and $R_1$, g, *, R, B, $X_1$, d, E, and Y are as defined above for Formula I, comprising reductively aminating a ketone of Formula XIII

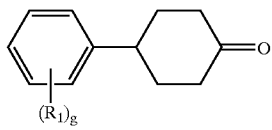

XIII wherein $R_1$ and g are as defined above, with an amine of Formula XIV

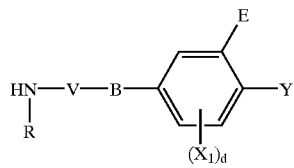

XIV wherein R, V, B, $X_1$, d, E, and Y are as defined above.

Another embodiment of the present invention is a method of preparing a compound of Formula VI

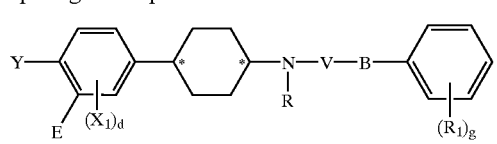

VI and pharmaceutically acceptable salts thereof wherein V is $(CH_2)_n$ wherein n is an integer of from 1 to 4 and Y, E, $X_1$, d, R, B, *, $R_1$, and g are as defined above for Formula VI, comprising reductively aminating a ketone of Formula XV

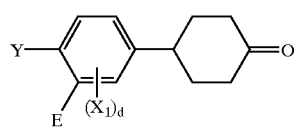

XV wherein Y, E, $X_1$, and d are as defined above, with an amine of Formula XVI

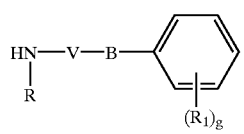

XVI wherein R, V, B, $R_1$, and g are as defined above.

DETAILED DESCRIPTION OF THE INVENTION

As described above, one aspect of the present invention are compounds of Formula I

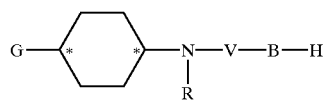

I and pharmaceutically acceptable salts thereof, wherein $R_1$, g, *, R, V, B, E, Y, $X_1$, and d are as defined above for Formula I.

All of the references cited herein, including patents, are incorporated herein by reference.

The following definitions apply to terms used in this specification and claims.

The term "subject" means a mammal, including a human.

Preferred subjects are humans, cats, dogs, cows, horses, pigs, and sheep.

The term "$IC_{50}$" means the concentration of test compound required to inhibit activity of a receptor or enzyme by 50%.

The term "L-DOPA" means 3-hydroxy-L-tyrosine.

The term "$(X_1)_d$" wherein d is an integer of from 0 to 2 means the group $X_1$ is present 0 to 2 times on the phenylene to which it is attached. The groups $X_1$ are independently the same or different. Illustrative examples of substituted phenylenes are drawn below.

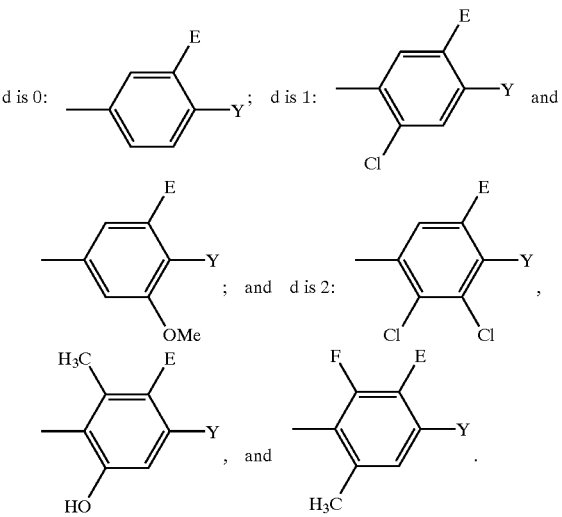

Likewise the term "$(R_1)_g$" wherein g is an integer of from 0 to 3 means the group $R_1$ is present 0 to 3 times on the phenyl to which it is attached. The groups $R_1$ are independently the same or different. Illustrative examples of substituted phenyls are drawn below.

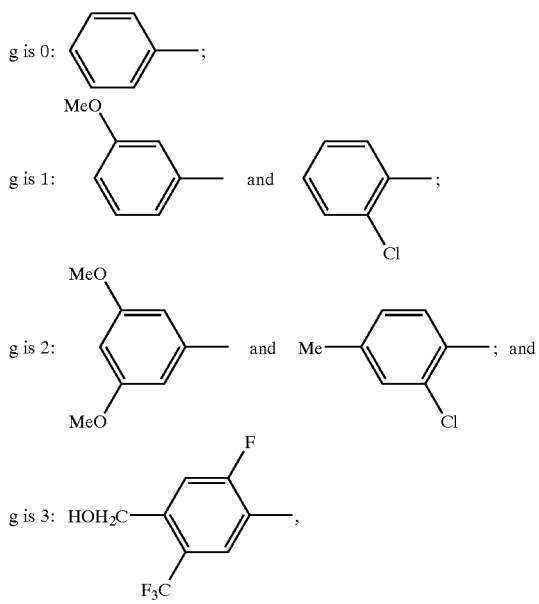

-continued

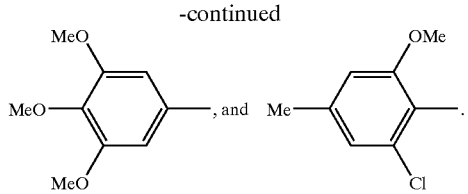

The term "comprising," which is synonymous with the terms "including," "containing," or "characterized by," is inclusive or open-ended and does not exclude additional, unrecited elements or method steps from the scope of the invention that follows.

The phrase "consisting of" is closed-ended and excludes any element, step, or ingredient not specified in the description of the invention that follows.

The phrase "consisting essentially of" limits the scope of the invention that follows to the specified elements or steps and those further elements or steps that do not materially affect the basic and novel characteristics of the invention.

The phrase "filter aid" means a filter medium comprising small particulates. Illustrative examples of filter aids include kieselguhr and CELITE (Celite Corporation, Lompoc, Calif.), a diatomaceous earth filter aid.

The term "alkyl" means a straight or branched, unsubstituted or substituted, hydrocarbon group having from 1 to 12 carbon atoms. Preferred alkyl groups are $C_1$–$C_6$ alkyl. Typical examples of unsubstituted alkyl groups include methyl (i.e., $CH_3$—), ethyl, 1-propyl, and 2-propyl, 1-butyl, 2-butyl, 2-methyl-1-propyl, 1,1-dimethylethyl, 1-pentyl, 2-pentyl, 3-pentyl, 2,2-dimethylpropyl, 1-hexyl, 2-hexyl, 3-hexyl, 4-methyl-1-pentyl, 1-heptyl, 2-heptyl, 3-heptyl, 4-heptyl, 5-methyl-1-hexyl, 1-octyl, 2-octyl, 3-octyl, 4-octyl, 6-methyl-1-heptyl, 5,5-dimethylhexyl, 1-nonyl, 2-nonyl, 1-decyl, 2-decyl, 1-undecyl, 2-undecyl, 1-dodecyl, and 5-dodecyl. Substituted alkyl groups are described below.

The term "alkenyl" means a straight or branched, unsubstituted or substituted, hydrocarbon group having from 2 to 12 carbon atoms and 1 or 2 sites of unsaturation. Preferred groups are $C_2$–$C_6$ alkenyl. Illustrative examples of unsubstituted alkenyl groups include ethenyl [i.e., $CH_2$=C(H)—], 1-propenyl, 2-propenyl, 1-buten-1-yl, 2-buten-1-yl, 1-penten-1-yl, 2-penten-1-yl, 1-penten-3-yl, 1-penten-5-yl, 1-hexen-1-yl, 1-hexen-4-yl, 2-hexen-1-yl, 3-hexen-1-yl, 2-octen-3-yl, 5-nonen-2-yl, 4-undecen-4-yl, and 5-dodecen-2-yl. Substituted alkenyl groups are defined below.

The term "alkoxy" means a straight or branched, substituted or unsubstituted, alkyl group of from 1 to 12 carbon atoms linked through an oxygen atom. Preferred is $C_1$–$C_6$ alkoxy. Illustrative examples of unsubstituted alkoxy groups include methoxy (i.e., $CH_3$—O—), ethoxy, isopropoxy, tert-butoxy, isopentoxy, octyloxy, and 7,7-dimethyloctyloxy. Substituted alkoxy groups are defined below.

The term "aryl" means an unsubstituted or substituted aromatic carbocyclic ring having 6 or 10 carbon atoms. Illustrative examples of unsubstituted aryl groups include phenyl (i.e., $C_6H_5$—), 1-naphthyl, and 2-naphthyl. Substituted aryl groups are defined below.

The term "aralkyl" means an unsubstituted or substituted aromatic carbocyclic ring having 6 or 10 carbon atoms (i.e., an aryl group) linked through an alkylene group, wherein alkylene is as defined below. Illustrative examples of unsubstituted aralkyl groups include benzyl, 2-phenylethyl, 3-phenylpropyl, 4-phenylbutyl, 3-methyl-3-phenylpropyl, 1-naphthylmethyl, 1-naphthylethyl, 3-(1-naphthyl)-propyl, 4-(1-naphthyl)-butyl, 4-(2-naphthyl)-butyl, 4-phenylheptyl, and 12-(2-hydroxyphenyl)-dodec-3-yl. Substituted aralkyl groups are defined below.

The term "alkylene" means a straight or branched hydrocarbon chain diradical of from 1 to 12 carbon atoms. Preferred groups are $C_1$–$C_6$ alkylene. Illustrative examples of alkylene groups include methylene (i.e., —$CH_2$—), 1,2-ethylene, 1,2-propylene, 1,3-propylene, 2,2-dimethylhexane-1,6-diyl, and dodecan-1,12-diyl.

The term "cycloalkyl" means an unsubstituted or substituted, saturated carbocyclic ring having from 3 to 7 carbon atoms. Illustrative examples of unsubstituted cycloalkyl groups include cyclopentyl, cyclopropyl, cyclohexyl or cycloheptyl. Substituted cycloalkyl is defined below.

As discussed above, the groups alkyl, alkenyl, alkoxy, aryl, aralkyl, and cycloalkyl may be substituted. These substituted groups are respectively termed:

"substituted alkyl",

"substituted alkenyl",

"substituted alkoxy",

"substituted aryl",

"substituted aralkyl", and

"substituted cycloalkyl".

These are groups substituted with from 1 to 3 substituents independently selected from halogen, OH, O—($C_1$–$C_6$ alkyl), OC(O)—($C_1$–$C_6$ alkyl), —($C_1$–$C_6$ alkylene)—OH, —($C_1$–$C_6$ alkylene)—O—($C_1$–$C_6$ alkyl), $NH_2$, N(H)—($C_1$–$C_6$ alkyl), N—($C_1$–$C_6$ alkyl)$_2$, NHC(O)—($C_1$–$C_6$ alkyl), —($C_1$–$C_6$ alkylene)—$NH_2$, —($C_1$–$C_6$ alkylene)—N(H)—($C_1$–$C_6$ alkyl), —($C_1$–$C_6$ alkylene)—N—($C_1$–$C_6$ alkyl)$_2$, SH, S—($C_1$–$C_6$ alkyl), S—C(O)—($C_1$–$C_6$ alkyl), —($C_1$–$C_6$ alkylene)—SH, —($C_1$–$C_6$ alkylene)—S—($C_1$–$C_6$ alkyl), unsubstituted cycloalkyl, C(O)—($C_1$–$C_6$ alkyl), $CO_2H$, $CO_2$—($C_1$–$C_6$ alkyl), C(O)$NH_2$, C(O)NH—($C_1$–$C_6$ alkyl), and C(O)N—($C_1$–$C_6$ alkyl)$_2$, wherein ($C_1$–$C_6$ alkyl) means a straight or branched hydrocarbon radical having from 1 to 6 carbon atoms, ($C_1$–$C_6$ alkylene) means a straight or branched hydrocarbon chain diradical of from 1 to 6 carbon atoms, and unsubstituted cycloalkyl is as defined above. Further, one of the three substituents in substituted alkyl, substituted alkenyl (on saturated carbons only), substituted alkoxy, substituted aralkyl (on saturated carbon atoms only) and substituted cycloalkyl may be oxo. Examples of these substituted groups are provided below.

Illustrative examples of substituted alkyl groups include $HOCH_2$, $CF_3$,

$(CH_2)_4SCH_3$, $(CH_2)_8NH_2$, $C(CH_3)_2CH[CO_2C(CH_3)_3]CH_3$, $CF_2OH$, and $CH(CO_2H)CH_2CH_2C(O)NMe_2$.

Illustrative examples of substituted alkenyl groups include 2-fluoro-ethen-1-yl [i.e., CH(F)=C(H)—], methyl propenoate-2-yl,

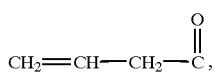

and 5-iso-butoxy-1-penten-5-yl.

Illustrative examples of substituted alkoxy groups include fluoromethoxy (i.e., FCH$_2$—O—), 2-ethoxycarbonyl-ethoxy, 4-aminocarbonyl-oxybutyl,

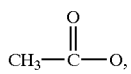

and 8-thio-nonyloxy [i.e., CH$_3$CH(SH)—(CH$_2$)$_7$—O—].

Illustrative examples of substituted aryl groups include 2-fluorophenyl, 2,4,6-trimethoxyphenyl, 4-chloro-2-methylphenyl, 5,6-dichloro-naphth-1-yl, and 8-(dimethylaminomethyl)-naphth-2-yl.

Illustrative examples of substituted aralkyl groups include 4-fluorophenylmethyl, 2-(2,4,6-trimethoxyphenyl)-ethyl, 3-(2-carboxyphenyl)-propyl, 4-phenyl-4-hydroxy-butyl, 4-(2-dimethylaminomethyl-naphth-1-yl)-butyl, benzoyl, and 12-(2-hydroxyphenyl)-dodec-3-yl.

Illustrative examples of substituted cycloalkyl groups include 3-methyl-cyclopentyl, cyclohexanon-4-yl, 4-hydroxy-cyclohexyl, and 1-methoxy-cycloheptyl.

The term "heteroatom" includes nitrogen, oxygen, and sulfur. When the heteroatom is incorporated in a nonaromatic ring, the heteroatom further includes

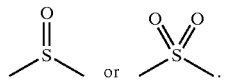

The term "oxo" means =O.

The term "oxo-substituted" means any group which contains a carbon atom that is substituted with an oxo group. A carbon atom substituted with an oxo group forms a carbonyl group, which is a group of formula C=O.

The phrase "fused 9- or 10-membered bicyclic ring containing from 0 to 3 heteroatoms" means a group wherein two ring systems share two and only two atoms. Illustrative examples of a fused bicyclic group containing 0 heteroatoms

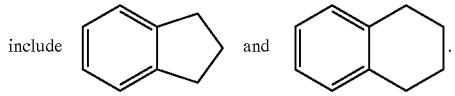

The term "halogen" means bromine, chlorine, fluorine or iodine.

The term "aminoalkyl" means a H$_2$N group linked through an alkylene group, wherein alkylene has the meaning as defined above. Illustrative examples of aminoalkyl groups include aminomethyl (i.e., H$_2$N—CH$_2$—), 3-aminopropyl, and 1-amino-1,1-dimethylethyl.

The term "alkylaminoalkyl" means an alkyl group, linked through an N(H) group, which in turn is linked through an alkylene group, wherein alkyl and alkylene are as defined above. Ilustrative examples of alkylaminoalkyl groups include methylaminomethyl (i.e., CH$_3$NHCH$_2$—), 3-(tert-butylamino)-propyl, and 6-(hexylamino)-hexyl.

The term "hydroxyalkyl" means an OH group linked through an alkylene group, wherein alkylene has the meaning defined above. Illustrative examples of hydroxyalkyl groups include hydroxymethyl, 2-hydroxyethyl, and 2-hydroxy-1,1-dimethylethyl.

The term "(aminocarbonyl)-alkyl" means an H$_2$NC(O) group linked through an alkylene group, wherein alkylene has the meaning defined above. Illustrative examples of (aminocarbonyl)-alkyl groups include H$_2$NC(O)—CH$_2$— and H$_2$NC(O)—C(CH$_3$)$_3$.

The term "(alkylthio)-alkyl-" means an alkyl group linked through a sulfur atom, which in turn is linked through an alkylene group, wherein alkyl and alkylene have the meanings defined above. Illustrative examples of (alkylthio)-alkyl groups include CH$_3$—S—CH$_2$—, CH$_3$CH$_2$—S—(CH$_2$)$_2$—, and CH$_3$CH(CH$_3$)CH$_2$C(CH$_3$)$_2$—S—C(CH$_3$)$_2$CH$_2$—.

The term "carboxyalkyl" means a CO$_2$H group linked through an alkylene group, wherein alkylene has the meaning defined above. Illustrative examples of carboxyalkyl groups include carboxymethyl, 2-carboxyethyl, and 2-carboxy-1,1-dimethylethyl.

The term "amino" means the —NH$_2$ group.

The term "haloalkyl" means a halogen linked through an alkylene group, wherein halogen and alkylene are as defined above. Illustrative examples of haloalkyl include trifluoromethyl, difluoromethyl, fluoromethyl, and 2,2,2-trichloroethyl.

The term "C(O)-alkyl" means an alkyl group as defined above linked through a carbonyl carbon atom. Illustrative examples of C(O)-alkyl groups include acetyl (i.e., C(O)CH$_3$), 2,2-dimethylpropionyl, and dodecanoyl.

The term "heterocyclene" means a 4-, 5-, or 6-membered, heterocyclic diradical, containing from 1 to 3 heteroatoms which are N, O, or S, and wherein the radical atoms are carbon atoms, selected from the group consisting of:

(i) 1-aza-2-cyclobutanon-3,4-diyl of formula

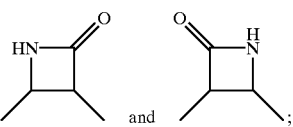

(ii) a 5-membered aromatic, nonaromatic dihydro, or nonaromatic tetrahydro ring diradical having carbon atoms and from 1 to 3 heteroatoms selected from N, O, and S;

(iii) a 5-membered oxo-substituted nonaromatic tetrahydro ring diradical having carbon atoms and 1 or 2 heteroatoms selected from N, O, and S;

(iv) a 6-membered aromatic, nonaromatic tetrahydro, or nonaromatic hexahydro ring diradical having carbon atoms and 1 or 2 heteroatoms, which heteroatoms are nitrogen, and (v) a 6-membered nonaromatic oxo-substituted hexahydro ring diradical having carbon atoms and 1 or 2 heteroatoms which are nitrogen and 0 or 1 heteroatom which is oxygen;

wherein when B is a nonaromatic heterocyclene containing sulfur, said sulfur may further comprise

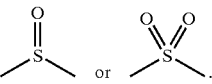

Illustrative examples of 5- and 6-membered heterocyclenes include:

1) A 5-membered heterocyclic ring diradical having one heteroatom which is N, O, or S such as, for example, the following rings:

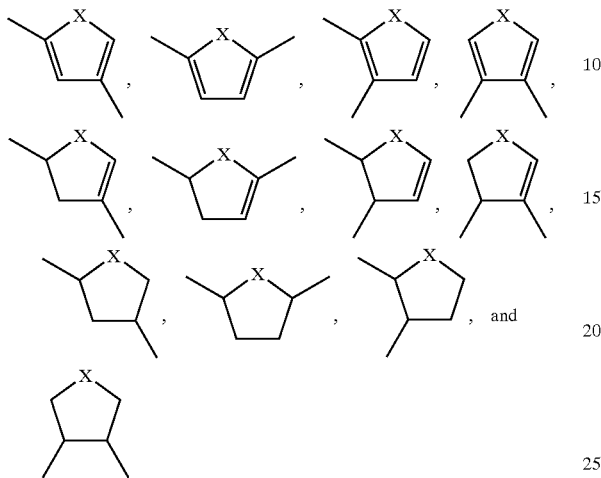

wherein X is O, S, or N—R wherein R is H or alkyl.

2) A 5-membered heterocyclic ring diradical having 2 heteroatoms independently selected from N, O, and S such as, for example, the following rings:

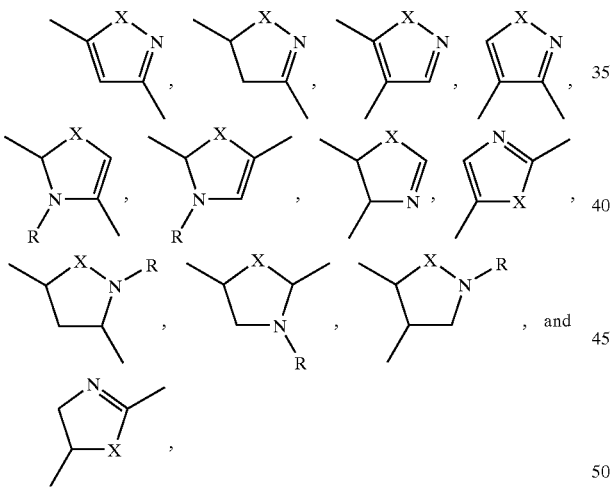

wherein X and R are as defined above in 1).

3) A 5-membered heterocyclic ring diradical having 3 heteroatoms independently selected from N, O, and S such as, for example, the following rings:

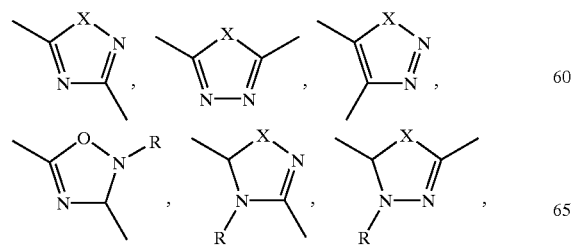

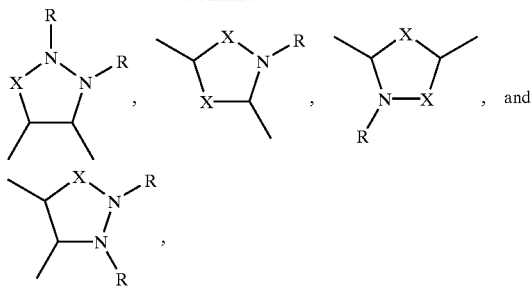

wherein X and R are as defined above in 1).

4) A 6-membered aromatic heterocyclic ring diradical having from 1 to 3 nitrogen atoms such as, for example, the following rings:

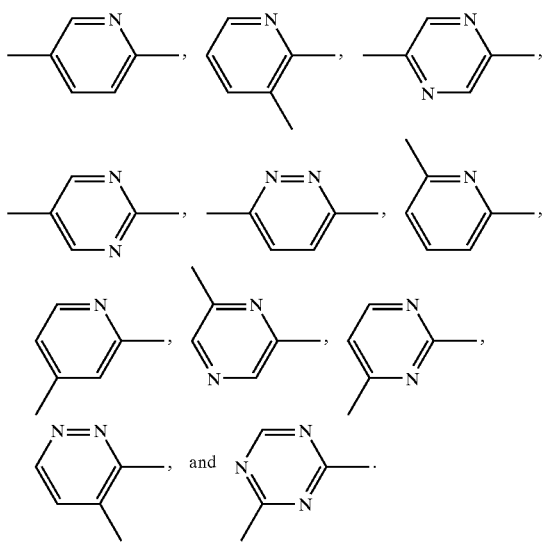

5) A 6-membered nonaromatic tetrahydro heterocyclic ring diradical having 1 or 2 nitrogen atoms such as, for example, the following rings:

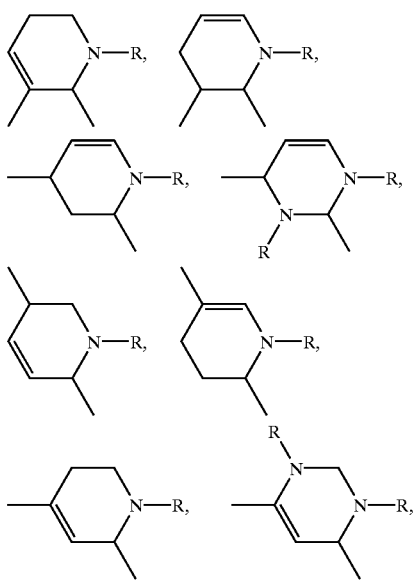

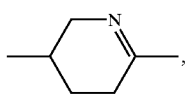

wherein R is independently hydrogen or alkyl;

6) A 6-membered nonaromatic hexahydro heterocyclic ring diradical having 1 or 2 nitrogen atoms such as, for example, the following rings:

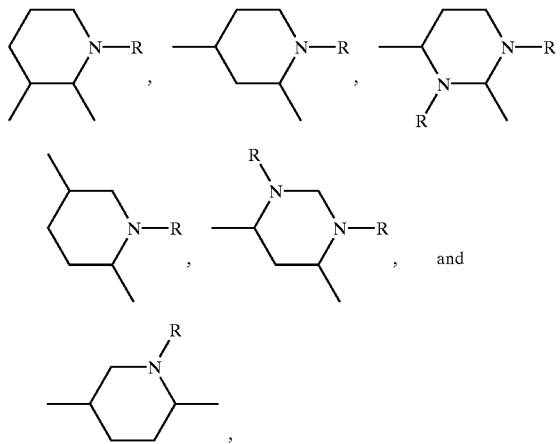

wherein R is independently hydrogen or alkyl;

7) A 5-membered oxo-substituted heterocyclic nonaromatic tetrahydro ring diradical having 1 or 2 heteroatoms independently selected from N, O, and S such as, for example, the following rings:

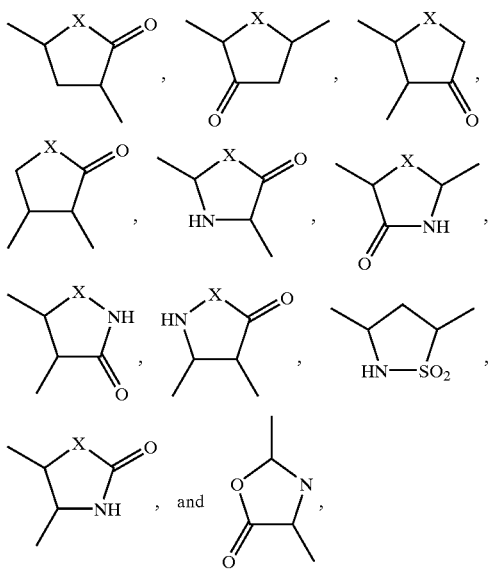

wherein X and R are as defined above in 1).

8) A 6-membered oxo-substituted hexahydro nonaromatic heterocyclic ring diradical having 1 or 2 nitrogen atoms, and 0 or 1 heteroatoms selected from O and S, such as, for example, the following rings:

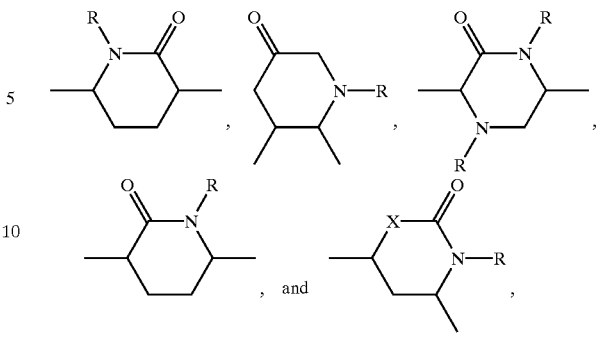

wherein R and X are as defined above in 1).

It is to be appreciated that the above rings in 1) to 8) are for illustration only and do not represent all possible isomers or rings that are described above by the term "heterocyclene." Rather, one of ordinary skill in the art of organic chemistry would know what is meant by the term heterocyclene in view of the above.

It is also to be appreciated that the compounds of Formula I, Formula VI, and Formula VIa may have chiral centers, in which case all stereoisomers thereof, both separately and as racemic and/or diastereoisomeric mixtures, are included.

Some of the compounds of Formula I, Formula VI, and Formula VIa are capable of further forming nontoxic pharmaceutically acceptable acid-addition and/or base salts. All of these forms are within the scope of the present invention.

For example, pharmaceutically acceptable acid addition salts of the compounds of Formula I, Formula VI, and Formula VIa include salts derived from inorganic acids such as hydrochloric, nitric, phosphoric, sulfuric, hydrobromic, hydriodic, hydrofluoric, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of basic invention compounds are prepared by contacting the free base forms of the invention compounds with a sufficient amount, usually 1 mole equivalent, of the desired acid to produce the salt in the conventional manner.

Pharmaceutically acceptable base salts are formed with metal cations, such as alkali and alkaline earth metal cations or amines, including organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenediamine, N-methylglucamine, and procaine (see, for example, Berge, supra., 1977).

Base salts of acidic invention compounds are prepared by contacting the free acid form of the invention compounds with a sufficient amount, usually 1 mole equivalent, of the desired base to produce a salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the invention may be prepared by a number of methods well-known to a person of average skill in the arts of organic and medicinal chemistries.

It should be appreciated that the organic and medicinal chemistry arts provide the skilled artisan with electronically searchable literature, reaction, and reagent databases and a wide variety of commercially available starting materials. For example, see the databases of the Chemical Abstracts service (Columbus, Ohio); Katritzky, Alan R., *Handbook of Heterocyclic Chemistry*, Pergamon Press, Ltd., 1985, Volumes 4 and 5; and The Aldrich Catalog (Sigma-Aldrich Corporation, St. Louis, Mo.).

For examples of the preparation of optically pure $\Delta^2$—isoxazolines (i.e., chiral $\Delta^2$—isoxazolines that consist of only one enantiomer, or substantially one enantiomer), see Yang, K-S, et al. *Tetrahedron Letters*, 2000;41:1453–1456 or Shimizu, M. et al. *Chemistry Letters*, 1996:455–456.

As described above, some of the invention compounds possess chiral centers. It should be appreciated that a person skilled in the medicinal and organic chemistry arts is able to prepare chiral invention compounds by classical resolution techniques and/or asymmetric synthesis.

It should also be appreciated for purposes of synthesizing the compounds of the present invention that reactive functional groups present in starting materials, reaction intermediates, or reaction products may be protected during chemical reactions using protecting groups which render the reactive functional groups substantially inert to the reaction conditions. After the chemical reaction requiring a protecting group for the starting material, reaction intermediate, or reaction product is completed, the protecting group may be removed. (See for example, *Protective Groups in Organic Synthesis*, 2nd ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), $\beta,\beta,\beta$-trichloroethoxycarbonyl (TCEC), $\beta$-iodoethoxycarbonyl; aryloxycarbonyl groups, such as benzyloxycarbonyl (CBZ), p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc. Use of protecting groups in organic synthesis is well within the skill of the average artisan.

It should be appreciated that reagents, solvents, and starting materials necessary for the preparation of the compounds of the invention may be purchased from a number of commercial sources or may be readily prepared by a number of methods well known to one of average skill in the art of organic chemistry. Further, reactions used to prepare the invention compounds can be carried out under a wide variety of conditions comprising solvents, reagents, catalysts, temperatures, time, atmosphere, and pressure.

Many different methods may be used to prepare the invention compounds. However for purposes of practicing the invention, which comprises compounds, pharmaceutical compositions, and methods of treating certain disorders and diseases, it does not matter how the compounds are made. Nevertheless, novel methods of preparing the invention compounds are valuable as they may afford improvements in ease of synthesis or purification, cost of preparation, or process time. As discussed above, the invention provides novel methods of making the invention compounds.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" by Theodora Green, supra. A number of general reactions such as oxidations and reductions are not shown in detail but can be done by methods understood by one skilled in the art. General transformations are well reviewed in "Comprehensive Organic Transformation" by Richard Larock, and the series "Compendium of Organic Synthetic Methods" (1989) published by Wiley-Interscience. In general, the starting materials were obtained from commercial sources unless otherwise indicated.

For example, one method of preparing a compound of Formula VIa is described below in Scheme 1.

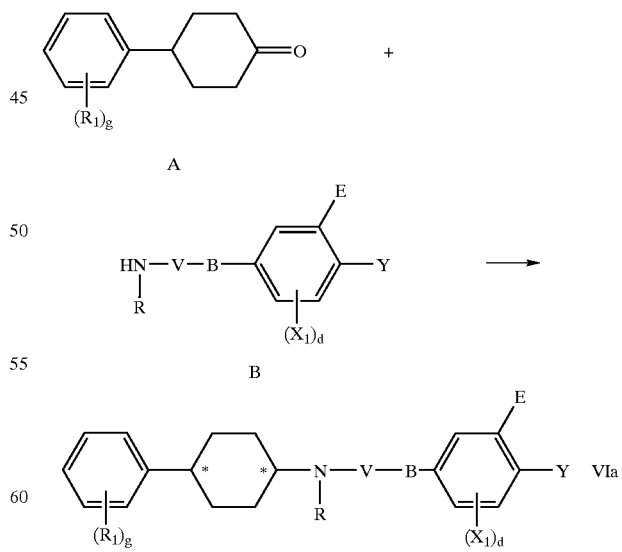

wherein $R_1$, g, *, R, V, B, E, Y, $X_1$, and d are as defined above for Formula VIa.

In Scheme 1, a compound of Formula A, wherein $R_1$ and g are as defined above, is allowed to react with a compound of Formula B, wherein R, V, B, E, Y, $X_1$, and d are as defined above, under reductive amination conditions to provide a compound of Formula VIa. In a preferred procedure, a compound of Formula A and a compound of Formula B (as its free base or an acid addition salt such as, for example, an HCl salt or a salt with acetic acid) in a molar ratio of about 1:1 are dissolved or suspended in a solvent such as, for example, THF, 2-propanol, 1,2-dichloroethane, dichloromethane, dioxane, and the like, optionally about 1 molar equivalent of a tertiary amine base such as, for example, triethylamine, diisopropylethylamine, N-methylmorpholine, and the like is added, and the mixture is stirred. Then an excess of a suitable hydride reducing agent is added such as, for example, sodium borohydride, sodium triacetoxyborohydride, and the like, and the mixture is stirred to provide a compound of Formula VIa. Preparation of Example 4a is representative of the chemistry described in Scheme 1.

Another method of preparing a compound of Formula VIa is described below in Scheme 2.

Scheme 2

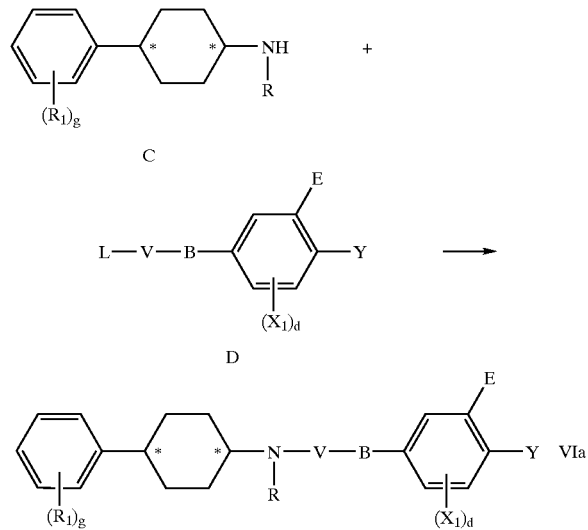

wherein $R_1$, g, *, R, V, B, $X_1$, d, E, and Y are as defined above for Formula VIa and L is a leaving group such that when V is $(CH_2)_n$ or $(CH_2)_m$—C=O, wherein m is not 0, L is, for example, halogen, $CH_3CO_2$—, $CF_3CO_2$—, $CF_3SO_3$—, p-toluyl-$SO_3$—, and the like; and when V is C=O, L is, for example, halogen, hydroxy, which can form intermediates activated for displacement by a compound of Formula C by reaction with coupling agents such as, for example, carbonyldiimidazole (CDI), N,N'-dicyclohexylcarbodiimide (DCC), and the like, benzotriazol-1-yl, imidazol-1-yl, $CH_3CO_2$—, and the like.

In Scheme 2, a compound of Formula C, wherein $R_1$, g, and R are as defined above, is allowed to react with a compound of Formula D, wherein L is a leaving group which is displaced by a compound of Formula C, to provide a compound of Formula VIa. In a preferred procedure, a compound of Formula C is dissolved or suspended in an aprotic, polar solvent such as, for example, N,N-dimethylformamide (DMF), ethyl acetate, dimethylsulfoxide (DMSO), acetonitrile, nitromethane, acetone, and the like, and optionally a 1 to 2 molar equivalents of a non-nucleophilic base such as, for example, triethylamine, diisopropylethylamine, sodium hydride, and the like is added, followed by addition of a compound of Formula D as a neat material (i.e., only the material itself in solid or liquid form) or in a solution of an aprotic, polar solvent such as, for example, the aprotic, polar solvents recited above, at an addition rate that maintains a desired reaction temperature, and the mixture is stirred in air or under an inert atmosphere such as, for example, nitrogen or argon, to give a compound of Formula VIa. In another preferred procedure, a compound of Formula C is dissolved or suspended in an aprotic, nonpolar solvent such as, for example, tetrahydrofuran (THF), diethylether, hexanes, and the like, and about 1 molar equivalent of a strong base such as, for example, n-butyl lithium, sec-butyl lithium, tert-butyl lithium, potassium hexamethyldisilazide (KHMDS), and the like is added, followed by addition of a compound of Formula D as a neat material or in a solution of a nonpolar, aprotic solvent such as, for example, the nonpolar, aprotic solvents recited above, at an addition rate that maintains a desired reaction temperature, and the mixture is stirred to give a compound of Formula VIa. In still another preferred procedure, a compound of Formula D, wherein L-V— is HO—C(O)—, is dissolved or suspended in an aprotic solvent such as, for example, THF, DMF, ethyl acetate, and the like, and about 1 molar equivalent of a coupling agent such as, for example, CDI, DCC, bis(2-oxo-3-oxazolidinyl)phosphinic chloride (BOP-Cl), and the like, followed by addition of a compound of Formula C as a neat material or in a solution of an aprotic solvent such as, for example, the aprotic solvents recited above, at an addition rate that maintains a desired reaction temperature, and the mixture is stirred to give a compound of Formula VIa wherein V is $(CH_2)_m$—C=O, wherein m is 0. Optionally, the compound of Formula VIa wherein V is $(CH_2)_m$—C=O, wherein m is 0 can be reduced using hydride-type reducing agents such as, for example, diisobutylaluminum hydride (DIBAL-H) in nonpolar, aprotic solvents such as, for example, THF, ethyl ether, toluene, and the like, to give a compound of Formula VIa wherein V is $(CH_2)_n$ wherein n is 1. In Scheme 2, the preferred molar ratio of a compound of Formula C to a compound of Formula D is about 1:1.

Another method of preparing a compound of Formula VIa is described below in Scheme 3.

Scheme 3

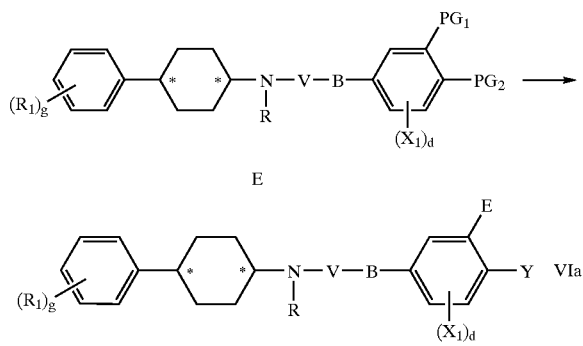

wherein $R_1$, g, *, R, V, B, $X_1$, d, E, and Y are as defined above for Formula VIa, and $PG_1$ and $PG_2$ are protecting groups which may be deprotected to provide the groups E and Y, respectively, of compounds of Formula VIa. Illustrative examples of $PG_1$ are hydrogen (when E is H), —O-benzyl, —S-benzyl, —NH-benzyl, —NH-(4-methoxybenzyl), —NH—BOC, —NH—CBZ, —O-TBDMS, —$CH_2$-halo, C(O)—$CH_2$-halo, —$CO_2$Me, C(O—$CH_2$)$_2$, $CH_2CH_2CO_2$Me, and the like. Illustrative examples of $PG_2$ are —NH-benzyl, —NH-(4- methoxybenzyl), —NH—BOC, —NH—CBZ, CO$_2$Me, —O-benzyl, —O-TBDMS, and the like.

In Scheme 3, a compound of Formula E is deprotected to give a compound of Formula VIa. In a preferred procedure, a compound of Formula E, wherein PG$_1$ and/or PG$_2$ is —O-benzyl, —S-benzyl, —NH-benzyl, —NH—CBZ, and the like, is dissolved or suspended in a suitable solvent such as, for example, acetic acid, ethanol, THF, dichloromethane, and the like, and allowed to react with a deprotecting reagent such as, for example, a mixture of hydrogen gas and a suitable hydrogenation catalyst such as, for example, palladium on carbon, palladium on barium sulfate, platinum on carbon, sponge nickel, and the like, under pressure, phosphorous tribromide, hydrochloric acid, titanium tetrachloride, and the like, at an addition rate that maintains a desired reaction temperature, to give a compound of Formula VIa. Preparation of Example 1 is representative of the chemistry described in Scheme 3.

Another method of preparing a compound of Formula VIa is described below in Scheme 4.

Scheme 4

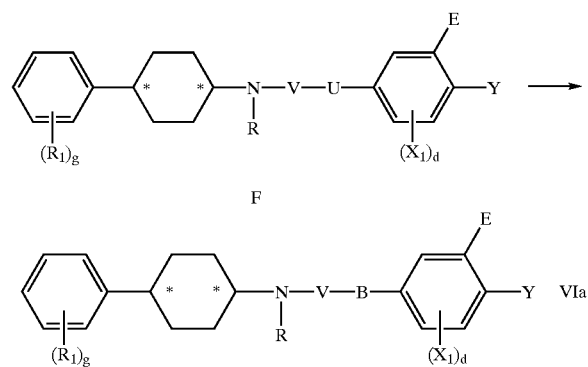

wherein R$_1$, g, *, R, V, B, X$_1$, d, E, and Y are as defined above for Formula VIa, and U is —C(H)=C(H)— or —C≡C—.

In Scheme 4, a compound of Formula F is allowed to react with a 2-membered, 3-membered, or 4-membered cyclization reagent to give a compound of Formula VIa, wherein B is a 4-membered, 5-membered, or 6-membered heterocyclene, respectively. In a preferred procedure, a compound of Formula F is dissolved or suspended in an aprotic solvent such as, for example, THF, dichloromethane, acetone, DMF, and the like, and allowed to react with a 3-membered cyclizing reagent such as, for example, an alkylazide, alkyldiazomethane, acetonitrile oxide, prepared by reaction of an aldoxime such as, for example, acetaldoxime [i.e., CH$_3$C(H)=N—OH] with a radical generating agent such as, N-bromosuccinimide (NBS), N-chlorosuccinimide (NCS), and the like, or a 4-membered cyclizing reagent such as, for example, H$_2$C=C(H)—C(H) =N-EDG, wherein EDG is an electron donating group such as, for example, —N(CH$_3$)$_2$, —OMe, and the like, to give a compound of Formula VIa.

Another method of preparing a compound of Formula VIa is described below in Scheme 5.

Scheme 5

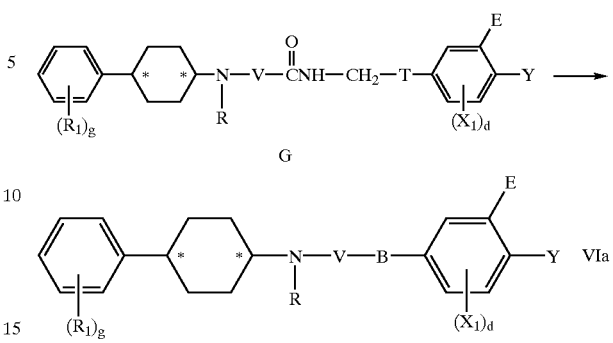

wherein R$_1$, g, *, R, V, X$_1$, d, E, and Y are as defined above for Formula VIa, B is oxazole, dihydrooxazole, thiazole, or dihydrothiazole, and T is C=O or C(H)OH.

In Scheme 5, a compound of Formula G is allowed to react with a reagent and/or catalyst under cyclizing conditions to provide a compound of Formula VIa. In a preferred procedure, a compound of Formula G is dissolved in an aprotic solvent such as, for example, THF, ethyl acetate, DMF, DMSO, and the like, and a dehydrating reagent such as, for example, anhydrous magnesium sulfate, anhydrous calcium chloride, activated three angstrom molecular sieves, trimethoxymethane, oxalyl chloride, PCl$_5$, phosphorous pentoxide and the like, is added and optionally an acid catalyst such as, for example, trifluoroacetic acid, paratoluenesulfonic acid, and the like, is added, and the mixture is stirred to provide a compound of Formula VIa, wherein B is oxazole or dihydrooxazole. In another preferred procedure, a compound of Formula G is dissolved in an aprotic solvent such as, for example, THF, ethyl acetate, DMF, DMSO, and the like, and a sulfurating reagent (i.e., a reagent that introduces a sulfur atom) such as, for example, P$_2$S$_5$, [2,4-bis(4-methoxyphenyl)-1,3-dithian-2,4-diphosphetane-2,4-disulfide] (i.e., Lawesson's reagent), and the like, is added, and the mixture is stirred to provide a compound of Formula VIa, wherein B is thiazole or dihydrothiazole.

Another method of preparing a compound of Formula VIa is described below in Scheme 6.

Scheme 6

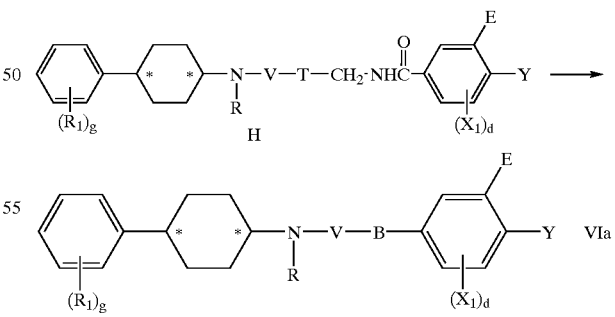

wherein R$_1$, g, *, R, V, X$_1$, d, E, and Y are as defined above for Formula VIa, B is oxazole, dihydrooxazole, thiazole, or dihydrothiazole, and T is C=O or C(H)OH.

In Scheme 6, a compound of Formula H is allowed to react with a reagent and/or catalyst under cyclizing conditions to provide a compound of Formula VIa. Preferred procedures are as described above in Scheme 5.

Another method of preparing a compound of Formula VIa is described below in Scheme 7.

Scheme 7

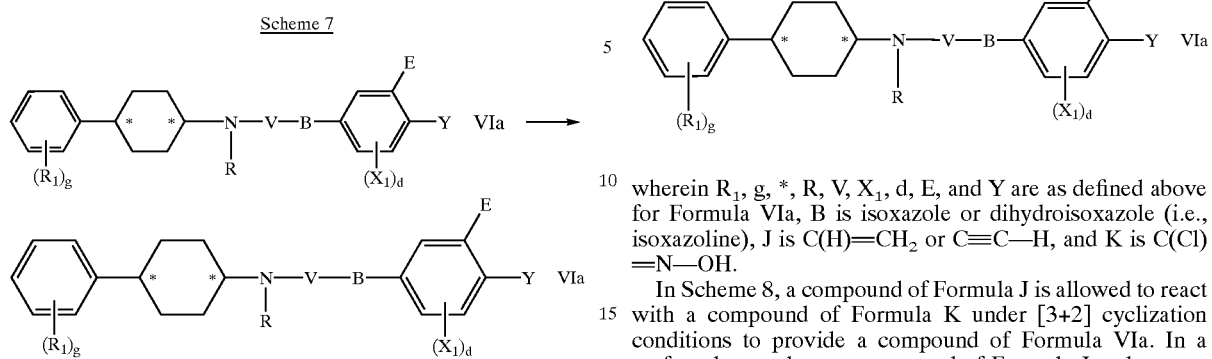

wherein $R_1$, g, *, R, V, B, $X_1$, d, E, and Y are as defined above for Formula VIa.

In Scheme 7, a compound of Formula VIa is allowed to react with a reagent to provide a different compound of Formula VIa. In a preferred procedure, a compound of Formula VIa wherein V is $(CH_2)_mC=O$ is dissolved or suspended in a suitable aprotic, nonpolar solvent such as, for example, THF, methyltertbutylether (MTBE), hexanes, and the like, and a reducing agent such as, for example, lithium aluminum hydride, sodium borohydride, sodium triacetoxyborohydride, diisobutylaluminum hydride (DIBAL), and the like, is added at an addition rate that maintains a desired reaction temperature, and the mixture is stirred to give a compound of Formula VIa wherein V is $(CH_2)_n$.

In another preferred procedure, a compound of Formula VIa wherein R is hydrogen is dissolved or suspended in a suitable aprotic, nonpolar solvent such as, for example, THF, MTBE, hexanes, and the like, and an alkylating agent of Formula $L_1$-R wherein L is halogen, o-tosyl, O-mesyl, and the like, and R is alkyl or wherein $L_1$-R is a dialkyl sulfate, is added, and the mixture is stirred to give a compound of Formula VIa wherein R is alkyl. Preparation of Example 4b is representative of the chemistry described in Scheme 7.

Another method of preparing a compound of Formula VIa is described below in Scheme 8.

Scheme 8

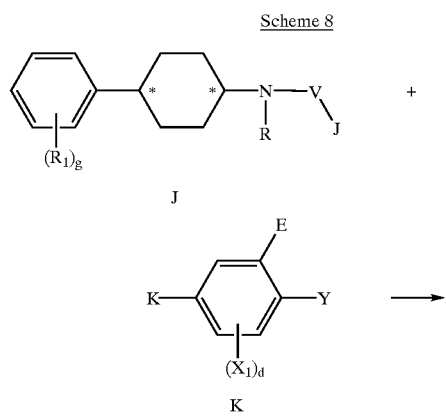

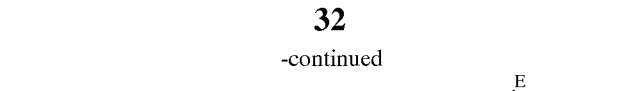

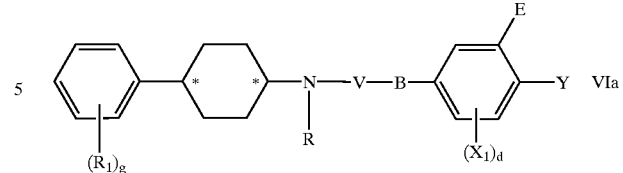

wherein $R_1$, g, *, R, V, $X_1$, d, E, and Y are as defined above for Formula VIa, B is isoxazole or dihydroisoxazole (i.e., isoxazoline), J is $C(H)=CH_2$ or $C\equiv C-H$, and K is $C(Cl)=N-OH$.

In Scheme 8, a compound of Formula J is allowed to react with a compound of Formula K under [3+2] cyclization conditions to provide a compound of Formula VIa. In a preferred procedure, a compound of Formula J and a compound of Formula K are dissolved or suspended in a solvent such as, for example, methanol, ethanol, THF, ethyl acetate, toluene, dichloromethane, and the like, and optionally a non-nucleophilic base such as, for example, triethylamine, diisopropylethylamine, sodium hydride, and the like is added, and the mixture is stirred to provide a compound of Formula VIa.

Further, one method of preparing a compound of Formula VI is described below in Scheme 9.

Scheme 9

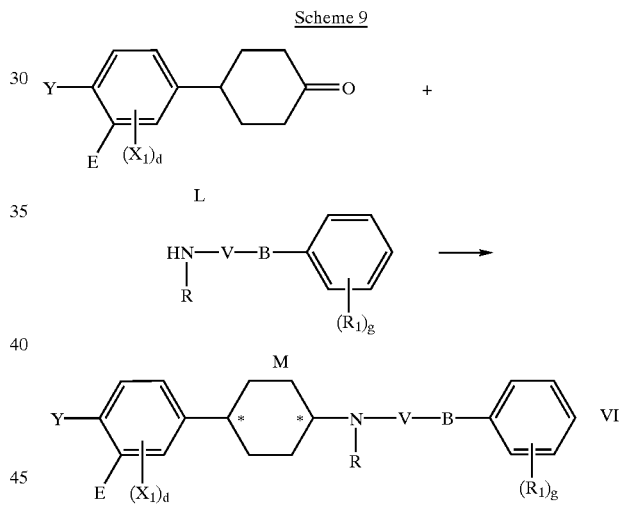

wherein $R_1$, g, *, R, V, B, E, Y, $X_1$, and d are as defined above for Formula VI.

In Scheme 9, a compound of Formula L, wherein Y, E, $X_1$, and d are as defined above, is allowed to react with a compound of Formula M, wherein R, V, B, $R_1$, and g are as defined above, under reductive amination conditions to provide a compound of Formula VI. In a preferred procedure, a compound of Formula L and a compound of Formula M (as its free base or an acid addition salt such as, for example, an HCl salt or a salt with acetic acid) in a molar ratio of about 1:1 are dissolved or suspended in a solvent such as, for example, THF, 2-propanol, 1,2-dichloroethane, dichloromethane, dioxane, and the like, optionally about 1 molar equivalent of a tertiary amine base such as, for example, triethylamine, diisopropylethylamine, N-methylmorpholine, and the like is added, and the mixture is stirred. Then an excess of a suitable hydride reducing agent such as, for example, sodium borohydride, sodium triacetoxyborohydride, and the like is added, and the mixture is stirred to provide a compound of Formula VI. Preparation of Examples 2, 3a, 5a, and 6a are representative of the chemistry described in Scheme 9.

Another method of preparing a compound of Formula VI is described below in Scheme 10.

Scheme 10

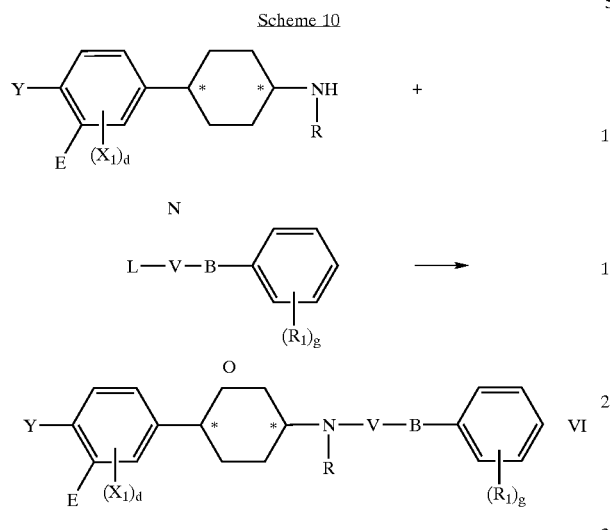

wherein Y, E, $X_1$, d, R, *, V, B, $R_1$, and g are as defined above for Formula VI and L is a leaving group such that when V is $(CH_2)_n$ or $(CH_2)_m$—C=O, wherein m is not 0, L is, for example, halogen, $CH_3CO_2$—, $CF_3CO_2$—, $CF_3SO_3$—, p-toluyl-$SO_3$—, and the like; and when V is C=O, L is, for example, halogen, hydroxy, which can form intermediates activated for displacement by a compound of Formula C by reaction with coupling agents such as, for example, carbonyldiimidazole (CDI), N,N'-dicyclohexylcarbodiimide (DCC), and the like, benzotriazol-1-yl, imidazol-1-yl, $CH_3CO_2$—, and the like.

In Scheme 10, a compound of Formula N, wherein Y, E, $X_1$, d, *, and R are as defined above, is allowed to react with a compound of Formula O, wherein L is a leaving group which is displaced by a compound of Formula N, to provide a compound of Formula VI. In a preferred procedure, a compound of Formula N is dissolved or suspended in an aprotic, polar solvent such as, for example, N,N-dimethylformamide (DMF), ethyl acetate, dimethylsulfoxide (DMSO), acetonitrile, nitromethane, acetone, and the like, and optionally a 1 to 2 molar equivalents of a non-nucleophilic base such as, for example, triethylamine, diisopropylethylamine, sodium hydride, and the like is added, followed by addition of a compound of Formula O as a neat material (i.e., only the material itself in solid or liquid form) or in a solution of an aprotic, polar solvent such as, for example, the aprotic, polar solvents recited above, at an addition rate that maintains a desired reaction temperature, and the mixture is stirred in air or under an inert atmosphere such as, for example, nitrogen or argon, to give a compound of Formula VI. In another preferred procedure, a compound of Formula N is dissolved or suspended in an aprotic, nonpolar solvent such as, for example, tetrahydrofuran (THF), diethylether, hexanes, and the like, and about 1 molar equivalent of a strong base such as, for example, n-butyl lithium, sec-butyl lithium, tert-butyl lithium, potassium hexamethyldisilazide (KHMDS), and the like is added, followed by addition of a compound of Formula O as a neat material or in a solution of a nonpolar, aprotic solvent such as, for example, the nonpolar, aprotic solvents recited above, at an addition rate that maintains a desired reaction temperature, and the mixture is stirred to give a compound of Formula VI. In still another preferred procedure, a compound of Formula O, wherein L-V— is HO—C(O)—, is dissolved or suspended in an aprotic solvent such as, for example, THF, DMF, ethyl acetate, and the like, and about 1 molar equivalent of a coupling agent such as, for example, CDI, DCC, bis(2-oxo-3-oxazolidinyl)phosphinic chloride (BOP—Cl), and the like, followed by addition of a compound of Formula N as a neat material or in a solution of an aprotic solvent such as, for example, the aprotic solvents recited above, at an addition rate that maintains a desired reaction temperature, and the mixture is stirred to give a compound of Formula VI. In Scheme 10, the preferred molar ratio of a compound of Formula N to a compound of Formula O is about 1:1.

Another method of preparing a compound of Formula VI is described below in Schemel 11.

Scheme 11

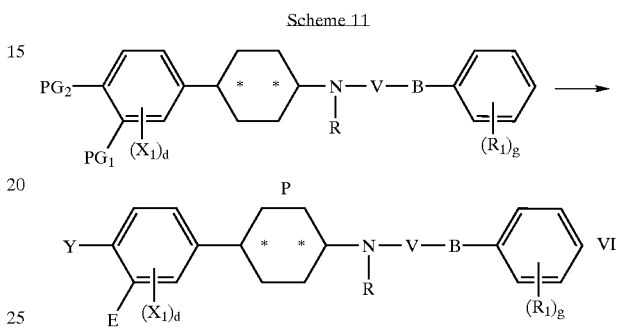

wherein $R_1$, g, *, R, V, B, $X_1$, d, E, and Y are as defined above for Formula VI, and $PG_1$ and $PG_2$ are protecting groups which may be deprotected to provide the groups E and Y, respectively, of compounds of Formula VI. Illustrative examples of $PG_1$ are hydrogen (when E is H), —O-benzyl, —S-benzyl, —NH-benzyl, —NH-(4-methoxybenzyl), —NH—BOC, —NH—CBZ, —O-TBDMS, —$CH_2$-halo, C(O)—$CH_2$-halo, —$CO_2$Me, C(O—$CH_2$)$_2$, $CH_2CH_2CO_2$Me, and the like. Illustrative examples of $PG_2$ are —NH-benzyl, —NH-(4-methoxybenzyl), —NH—BOC, —NH—CBZ, $CO_2$Me, —O-benzyl, —O-TBDMS, and the like.

In Scheme 11, a compound of Formula P is deprotected to give a compound of Formula VI. In a preferred procedure, a compound of Formula P, wherein $PG_1$ and/or $PG_2$ is —O-benzyl, —S-benzyl, —NH-benzyl, —NH—CBZ, and the like, is dissolved or suspended in a suitable solvent such as, for example, acetic acid, ethanol, THF, dichloromethane, and the like, and allowed to react with a deprotecting reagent such as, for example, a mixture of hydrogen gas and a suitable hydrogenation catalyst such as, for example, palladium on carbon, palladium on barium sulfate, platinum on carbon, sponge nickel, and the like, under pressure, phosphorous tribromide, hydrochloric acid, titanium tetrachloride, and the like, at an addition rate that maintains a desired reaction temperature, to give a compound of Formula VI.

Another method of preparing a compound of Formula VI is described below in Scheme 12.

Scheme 12

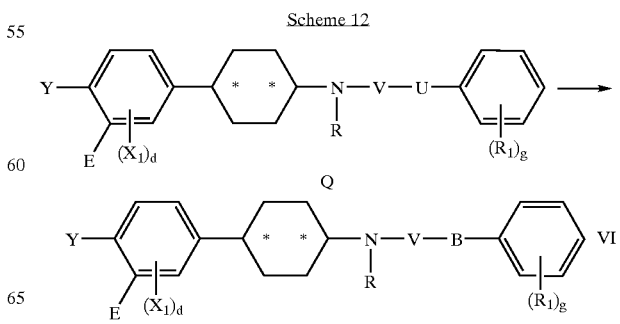

wherein $R_1$, g, *, R, V, B, $X_1$, d, E, and Y are as defined above for Formula I, and U is —C(H)=C(H)— or —C≡C—.

In Scheme 12, a compound of Formula Q is allowed to react with a 2-membered, 3-membered, or 4-membered cyclization reagent to give a compound of Formula VI, wherein B is a 4-membered, 5-membered, or 6-membered heterocyclene, respectively. In a preferred procedure, a compound of Formula Q is dissolved or suspended in an aprotic solvent such as, for example, THF, dichloromethane, acetone, DMF, and the like, and allowed to react with a 3-membered cyclizing reagent such as, for example, an alkylazide, alkyldiazomethane, acetonitrile oxide, prepared by reaction of an aldoxime such as, for example, acetaldoxime [i.e., $CH_3C(H)$=N—OH] with a radical generating agent such as, N-bromosuccinimide (NBS), N-chlorosuccinimide (NCS), and the like, or a 4-membered cyclizing reagent such as, for example, $H_2C$=C(H)—C(H)=N-EDG, wherein EDG is an electron donating group such as, for example, —N(CH$_3$)$_2$, —OMe, and the like, to give a compound of Formula VI.

Another method of preparing a compound of Formula VI is described below in Scheme 13.

Scheme 13

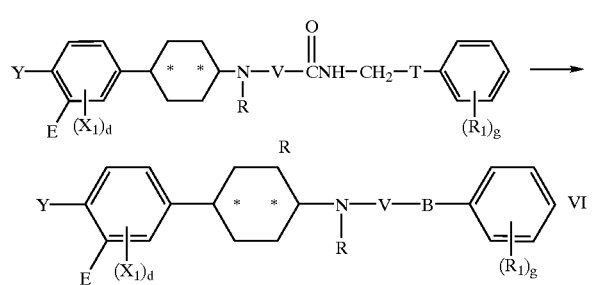

wherein $R_1$, g, *, R, V, $X_1$, d, E, and Y are as defined above for Formula VI, B is oxazole, dihydrooxazole, thiazole, or dihydrothiazole, and T is C=O or C(H)OH.

In Scheme 13, a compound of Formula R is allowed to react with a reagent and/or catalyst under cyclizing conditions to provide a compound of Formula VI. In a preferred procedure, a compound of Formula R is dissolved in an aprotic solvent such as, for example, THF, ethyl acetate, DMF, DMSO, and the like, and a dehyrdating reagent such as, for example, anhydrous magnesium sulfate, anhydrous calcium chloride, activated three angstrom molecular sieves, trimethoxymethane, oxalyl chloride, PCl$_5$, phosphorous pentoxide and the like, is added and optionally an acid catalyst such as, for example, trifluoroacetic acid, para-toluenesulfonic acid, and the like, is added, and the mixture is stirred to provide a compound of Formula VI, wherein B is oxazole or dihydrooxazole. In another preferred procedure, a compound of Formula R is dissolved in an aprotic solvent such as, for example, THF, ethyl acetate, DMF, DMSO, and the like, and a sulfurating reagent (i.e., a reagent that introduces a sulfur atom) such as, for example, $P_2S_5$, [2,4-bis(4-methoxyphenyl)-1,3-dithian-2,4-diphosphetane-2,4-disulfide] (i.e., Lawesson's reagent), and the like, is added, and the mixture is stirred to provide a compound of Formula VI, wherein B is thiazole or dihydrothiazole.

Another method of preparing a compound of Formula VI is described below in Scheme 14.

Scheme 14

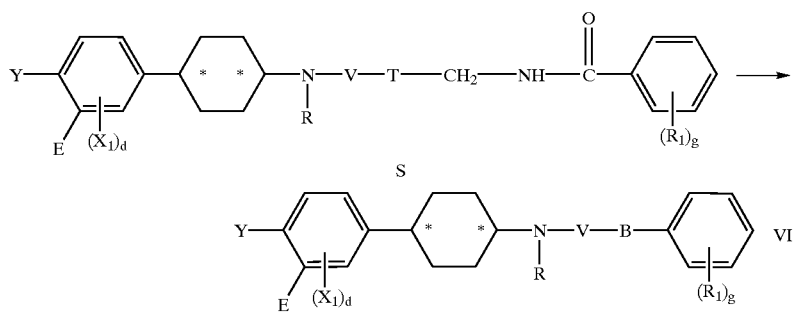

wherein $R_1$, g, *, R, V, $X_1$, d, E, and Y are as defined above for Formula VI, B is oxazole, dihydrooxazole, thiazole, or dihydrothiazole, and T is C=O or C(H)OH.

In Scheme 14, a compound of Formula S is allowed to react with a reagent and/or catalyst under cyclizing conditions to provide a compound of Formula VI. Preferred procedures are as described above in Scheme 13.

Another method of preparing a compound of Formula VI is described below in Scheme 15.

Scheme 15

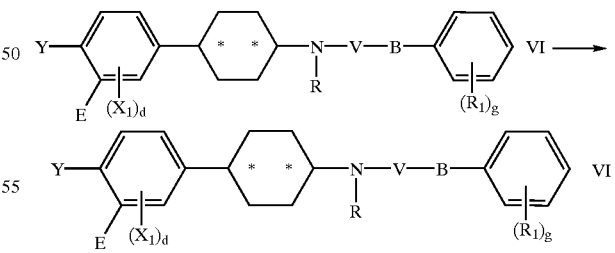

wherein $R_1$, g, *, R, V, B, $X_1$, d, E, and Y are as defined above for Formula VI.

In Scheme 15, a compound of Formula VI is allowed to react with a reagent to provide a different compound of Formula VI. In a preferred procedure, a compound of Formula VI wherein V is $(CH_2)_mC$=O is dissolved or suspended in a suitable aprotic, nonpolar solvent such as, for example, THF, methyltertbutylether (MTBE), hexanes, and the like, and a reducing agent such as, for example, lithium aluminum hydride, sodium borohydride, sodium triacetoxyborohydride, diisobutylaluminum hydride (DIBAL), and the like, is added at an addition rate that maintains a desired reaction temperature, and the mixture is stirred to give a compound of Formula VI wherein V is $(CH_2)_n$.

In another preferred procedure, a compound of Formula VI wherein R is hydrogen is dissolved or suspended in a suitable aprotic, nonpolar solvent.such as, for example, THF, MTBE, hexanes, and the like, and an alkylating agent of Formula $L_1$—R wherein L is halogen, o-tosyl, o-mesyl, and the like, and R is alkyl or wherein $L_1$—R is a dialkyl sulfate, is added, and the mixture is stirred to give a compound of Formula VI wherein R is alkyl. The preparations of Examples 3b, 5b, and 6b are representative of the chemistry described in Scheme 15.

Another method of preparing a compound of Formula VI is described below in Scheme 16.

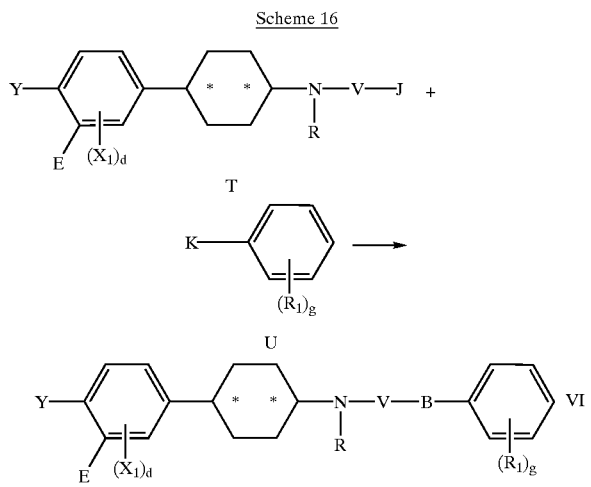

wherein $R_1$, g, *, R, V, $X_1$, d, E, and Y are as defined above for Formula VI, B is isoxazole or dihydroisoxazole (i.e., isoxazoline), J is C(H)=CH$_2$ or C≡C—H, and K is C(Cl)=N—OH.

In Scheme 16, a compound of Formula T is allowed to react with a compound of Formula U under [3+2] cyclization conditions to provide a compound of Formula VI. In a preferred procedure, a compound of Formula T and a compound of Formula U are dissolved or suspended in a solvent such as, for example, methanol, ethanol, THF, ethyl acetate, toluene, dichloromethane, and the like, and optionally a non-nucleophilic base such as, for example, triethylamine, diisopropylethylamine, sodium hydride, and the like is added, and the mixture is stirred to provide a compound of Formula VI.

Preparation of certain compounds of the present invention use the general methods described immediately below.
General Methods HCl salts were prepared by treatment of a MeOH solution of the amine with excess HCl in Et$_2$O (1 M). The salts were isolated either by filtration if they precipitated directly from the etherial solution, or by first removal of the solvent under reduced pressure, and then crystallization (Et$_2$O:MeOH).

Purity was determined by reversed phase HPLC by the following methods:

Method A: column: YMC J'SPHERE (YMC Company, Limited, Kyoto, Japan) C18, ODS-M80, 150×4.6 mm, 4 µm; solvent A: 0.1% H$_3$PO$_4$ in 95:5 H$_2$O:CH$_3$CN; solvent B: 0.1% H$_3$PO$_4$ in 95:5 CH$_3$CN:H$_2$O; gradient: 10–100% B over 15 minutes; flow: 1 mL minute$^{-1}$; detection: 210 nm.

Method B: column: YMC J'SPHERE C18, ODS-M80, 150×4.6 mm, 4µ; solvent A: 0.1% H$_3$PO$_4$ in 0.1% H$_3$PO$_4$ in 95:5 H$_2$O:CH$_3$CN; solvent B: 0.1% H$_3$PO$_4$ in 95:5 CH$_3$CN:H$_2$O; gradient: 10–100% B over 15 minutes; flow: 1 mL minute$^{-1}$; detection: 210 nm.

Method C: column: DYNAMAX C-18, 250×21.4 mm, 300 Å; solvent A: 0.1% trifluoroacetic acid in 95:5 H$_2$O:CH$_3$CN; solvent B: 0.1% trifluoroacetic acid in 95:5 CH$_3$CN:H$_2$O; gradient: 10–100% B over 30 minutes; flow: 10 mL minute$^{-1}$; detection: 210 nm.

Further, the examples use certain common intermediates. These intermediates may be prepared by the procedures described below in Preparations 1 to 4.

PREPARATION 1

A preparation of 6-(4-cyclohexanonyl)benzoxazolin-2-one (5) is shown in Scheme 17.

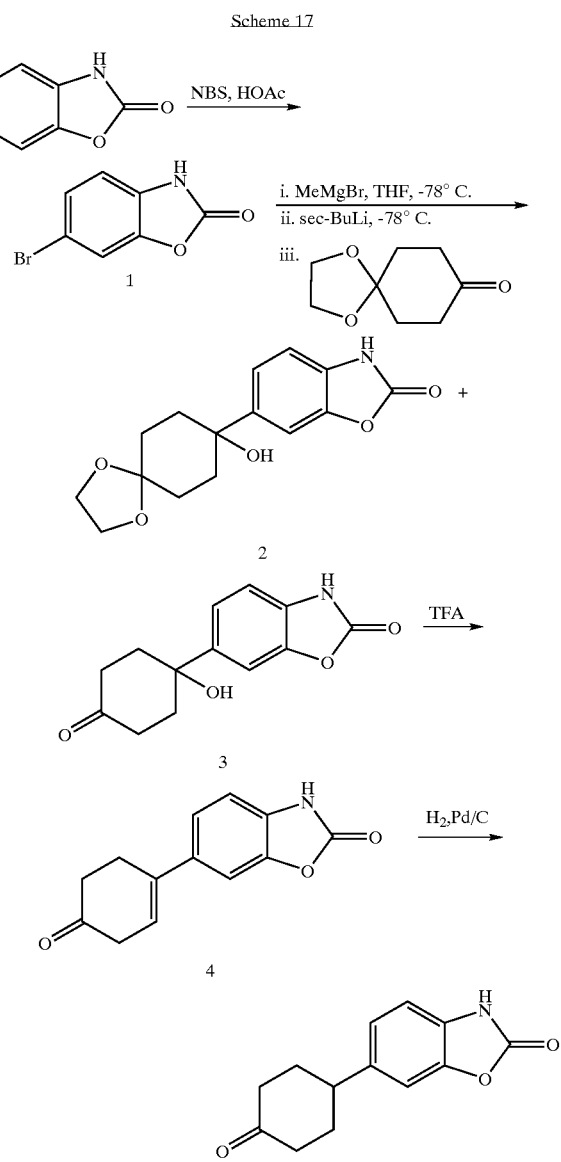

Step 1: N-Bromosuccinimide (NBS, 26.6 g, 0.15 mol) was added to a stirred solution of 2-benzoxazolinone (20.0 g, 0.15 mol) in glacial acetic acid (220 mL) and the mixture was stirred at room temperature for 3 days. The reaction mixture was poured into H₂O (1.2 L), and the white solid that formed was filtered off. Recrystallization of the white solid from hot EtOH (300 mL) gave the bromide of formula 1 (22.1 g, 70%), as an off-white solid: melting point (mp) 190–195° C.; IR (KBr): 3278, 1779, 1736, 1623 cm⁻¹; ¹H NMR (300 MHz, CD₃OD) δ 7.41 (d, J=2 Hz, 1H), 7.32 (dd, J=5, 2 Hz, 1H), 6.99 (d, J=5 Hz, 1H); CI MS (methane) (m/z): 215 [M+H]⁺.

Step 2: The bromide of formula 1 (12.8 g, 59.6 mmol) was dissolved in anhydrous tetrahydrofuran (THF) (220 mL), and the solution was cooled to −78° C. Solutions of MeMgBr (21.9 mL of a 3.0 M solution in Et₂O, 65.6 mmol), sec-BuLi (50.4 mL of a 1.3 M solution in cyclohexane, 65.6 mmol), and 1,4-cyclohexanedione mono-ethylene ketal (11.2 g, 71.5 mmol) in anhydrous THF (10 mL) were added sequentially at 30-minute intervals. After the final addition, the reaction mixture was allowed to warm to room temperature. The reaction was quenched by the addition of 1N HCl (25 mL). The reaction mixture was diluted with EtOAc (500 mL), washed with saturated (satd) NaCl (250 mL), dried (Na₂SO₄), filtered and concentrated under reduced pressure to provide a mixture of ketal of formula 2 and ketone of formula 3, as a brown oil.

Step 3: The crude mixture of ketal of formula 2 and ketone of formula 3 from Step 2 was stirred in trifluoroacetic acid (TFA) (20 mL) at room temperature for 20 minutes. The red solution was poured into CHCl₃ (500 mL), and the organic layer was washed with H₂O (2×100 mL), saturated NaHCO₃, and saturated NaCl, dried (Na₂SO₄), filtered and concentrated under reduced pressure. Purification by filtration through silica gel (eluent 9:1 CHCl₃/MeOH) gave a yellow oil. Crystallization from hexanes/EtOAc (3:1) gave cyclohexenone of formula 4 (8.1 g, 59%): ¹H NMR (300 MHz, DMSO-d₆) δ 7.40 (d, J=1 Hz, 1H), 7.30 (dd, J=8, 1 Hz, 1H), 7.06 (d, J=8 Hz, 1H), 6.11 (t, J=4 Hz, 1H), 3.01 J=2 Hz, 2H), 2.83 (t, J=7 Hz, 2H), 2.53 (m, 2H); CI MS (methane) (m/z): 230 [M+H]⁺.

Step 4: A mixture of the cyclohexenone of formula 4 (3.5 g, 15.3 mmol) in a 3: 2 mixture of EtOAc/EtOH (100 mL) and 10% Pd/C (0.5 g) was shaken under an H₂ atmosphere at 50 pounds per square inch (psi) for 4 hours. The solution was filtered through CELITE and concentrated under reduced pressure. Crystallization from hexanes/EtOAc (3:1) gave 6-(4-cyclohexanonyl)benzoxazolin-2-one of formula 5 (3.45 g, 98%) as a white solid: mp 202–211° C.; IR (KBr): 3339, 1777, 1713, 1618 cm⁻¹; ¹H NMR (300 MHz, DMSO-d₆) δ 7.26 (s, 1H), 7.08 (d, J=8 Hz, 1H), 7.01 (d, J=8 Hz, 1H), 3.08 (tt, J=14, 4 Hz, 1H), 2.63–2.51 (m, 2H), 2.24 (br d, J=14 Hz, 2H), 2.07–2.02 (m, 2H), 1.95–1.85 (dddd, J=14, 14, 14, 4 Hz, 2H).

PREPARATION 2

Preparation of 6-(4-substituted amino-cyclohexyl)-benzoxazolin-2-ones is shown below in Scheme 18.

Scheme 18

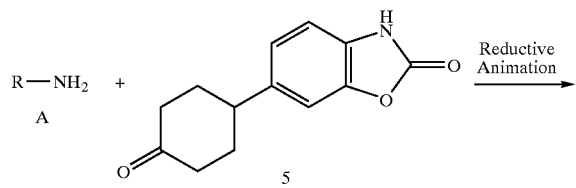

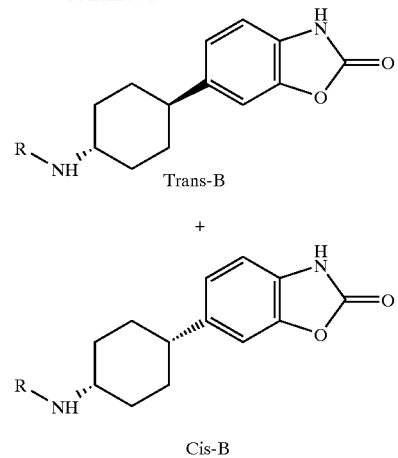

In general, these compounds can be prepared by a reductive amination reaction between an amine of formula (A) and 6-(4-cyclohexanonyl)benzoxazolin-2-one of formula (5) to give the trans and cis cyclohexylamines of formulas (trans-B) and (cis-B), respectively.

For example, a mixture of 1 mol equivalent of methylbenzylamine, 1 mol equivalent of ketone of formula 5, 1:1 2-propanol:1,2-dichloroethane, (and optionally 1 mol equivalent of triethylamine if methylbenzylamine as its hydrochloride or acetic acid salt is used instead of the free base), and 3 Å molecular sieves is stirred for 1 hour at room temperature. Excess sodium borohydride or sodium triacetoxyborohydride is added, and the mixture is stirred overnight to give 6-[(4-benzyl-methyl-amino)-cyclohexyl]-3H-benzoxazolin-2-one after purification by flash chromatography on silica gel. 6-[(4-Benzyl-methyl-amino)-cyclohexyl]-3H-benzoxazol-2-one is then combined with a catalytic amount of 10% Pd/C in THF-MeOH, and shaken under H₂ atmosphere at 50 psi to give 6-(4-methylamino) cyclohexyl-3H-benzoxazolin-2-one of formula 15 after purification by flash chromatography. See Example 1 below for experimental details.

PREPARATION 3

The preparation of 4-(4-Fluoro-phenyl)-cyclohexanone of formula 34 is described below in Scheme 19.

Scheme 19

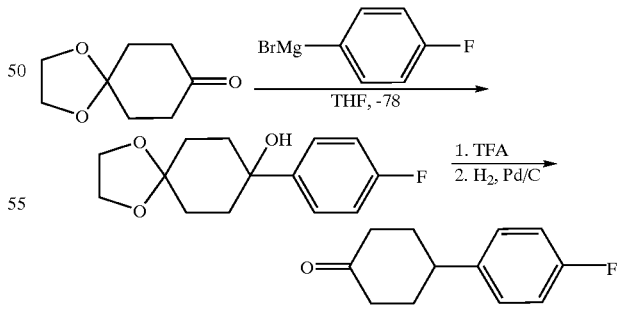

Step 1: 1,4-Cyclohexanedione mono-ethylene ketal (10.1 g, 64.7 mmol) was dissolved in anhydrous THF (100 mL), and the solution was cooled to −78° C. 4-Fluorophenylmagnesium bromide (78 mL of a 1.0 M solution in THF, 78 mmol) was added slowly over 10 minutes. After 20 minutes, saturated NH₄Cl (10 mL) was added and the mixture allowed to warm to room temperature. The mixture was partitioned between CHCl₃ and saturated NH₄Cl. The organic layer was dried (Na₂SO₄), filtered through CELITE, and concentrated under reduced pressure. Purification by flash chromatography (silica gel, 1:9 to 3:7 EtOAc: hexanes, loaded in a minimum of CH₂Cl₂) gave 4-(4-fluoro-phenyl)-4-hydroxy-cyclohexanone ethylene ketal (10.9 g, 67%); ¹H NMR (300 MHz, CDCl₃) δ 7.5 (dd, J=8, 8 Hz, 2H), 7.05 (dd, J=8, 8 Hz, 2H), 4.00–3.91 (m, 5H), 2.25–2.08 (m, 4H), 1.85 (d, J=8 Hz, 2H), 1.65 (d, J=8 Hz, 2H).

Step 2: Compound 4-(4-Fluoro-phenyl)-4-hydroxy-cyclohexanone ethylene ketal (8.23 g, 32.6 mmol) from Step 1 was stirred in TFA (25 mL) for 15 minutes. The reaction mixture was poured into H₂O (100 mL) and then extracted with CHCl₃ (2×75 mL). The organic solution was washed with saturated bicarbonate, dried (Na₂SO₄), filtered and concentrated under reduced pressure to afford crude 1-(4-fluorophenyl)-cyclohexen-4-one (6.44 g); ¹H NMR (300 MHz, CDCl₃) δ 7.35 (dd, J=8, 8 Hz, 2H), 7.04 (dd, J=8, 8 Hz, 2H), 6.05 (m, 1H), 3.05 (m, 2H), 2.87 (m, 2H), 2.65 (dd, J=7, 7 Hz, 2H).

Step 3: A solution of the crude 1-(4-fluorophenyl)-cyclohexen-4-one (6.44 g) from Step 2, 10% Pd/C (0.20 g) in EtOAc (100 mL) was shaken under an H₂ atmosphere at 50 psi for 1 hour. The solution was filtered through CELITE, and the filtrate was concentrated under reduced pressure. Purification by flash chromatography (silica, 1:9 EtOAc: hexanes) gave the ketone of formula 34 (5.49 g, 88%) as a pale yellow solid: mp 35–39° C.; IR (KBr): 2935, 1713, 1510 cm⁻¹; ¹H NMR (500 MHz, CDCl₃) δ 7.22–7.15 (m, 2H), 7.04–6.96 (m, 2H), 3.02 (dt, J=7, 3 Hz, 1H), 2.55–2.44 (m, 4H), 2.23–2.21 (m, 2H), 1.95–1.86 (m, 2H); CI-MS (methane) (m/z): 193 [M+H]⁺; HPLC: method A, 11.59 min (96.7%). Certain amines containing aryl groups are known:

2-(4-Fluorophenoxy)ethylamine: Beilstein Registry Number: 1941572; Chemical Abstracts Service Registration Number (CAS Reg. No.): 6096-89-5; Shtacher G., Taub W., *J. Med. Chem.* 1966;9: 197–203.

3-(4-Fluorophenyl)propylamine: Beilstein Registry Number: 7757402; Fujimura K., Matsumoto J., Niwa M., Kobayashi T., Kawashima Y. et al., *Bioorg. Med. Chem.* 1997;55: 1675–1684.

3-Phenylsulfanylpropylamine: Beilstein Registry Number: 3695289; CAS : 34946-13-9; References to use of: Uher M.; Jendrichovsky, J. *Collect. Czech Chem. Commun.* 1973;38: 620–624; Tucker H., Coope J. F., *J. Med. Chem.* 1978;21: 769–773.

3-p-Tolylpropylamine: Beilstein Reference Number: 3235743; CAS: 54930-39-1; v.Braun; Wirz, *Chem. Ber.* 1927;60:107.

Certain compounds of the present invention have been prepared as described in the Examples below.

EXAMPLE 1 trans-6-(5-{[Methyl-(4-phenyl-cyclohexyl)-amino]-methyl}-4,5-dihydro-isoxazol-3-yl)-3H-benzoxazol-2-one (17)

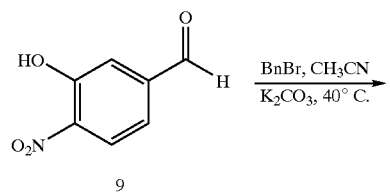

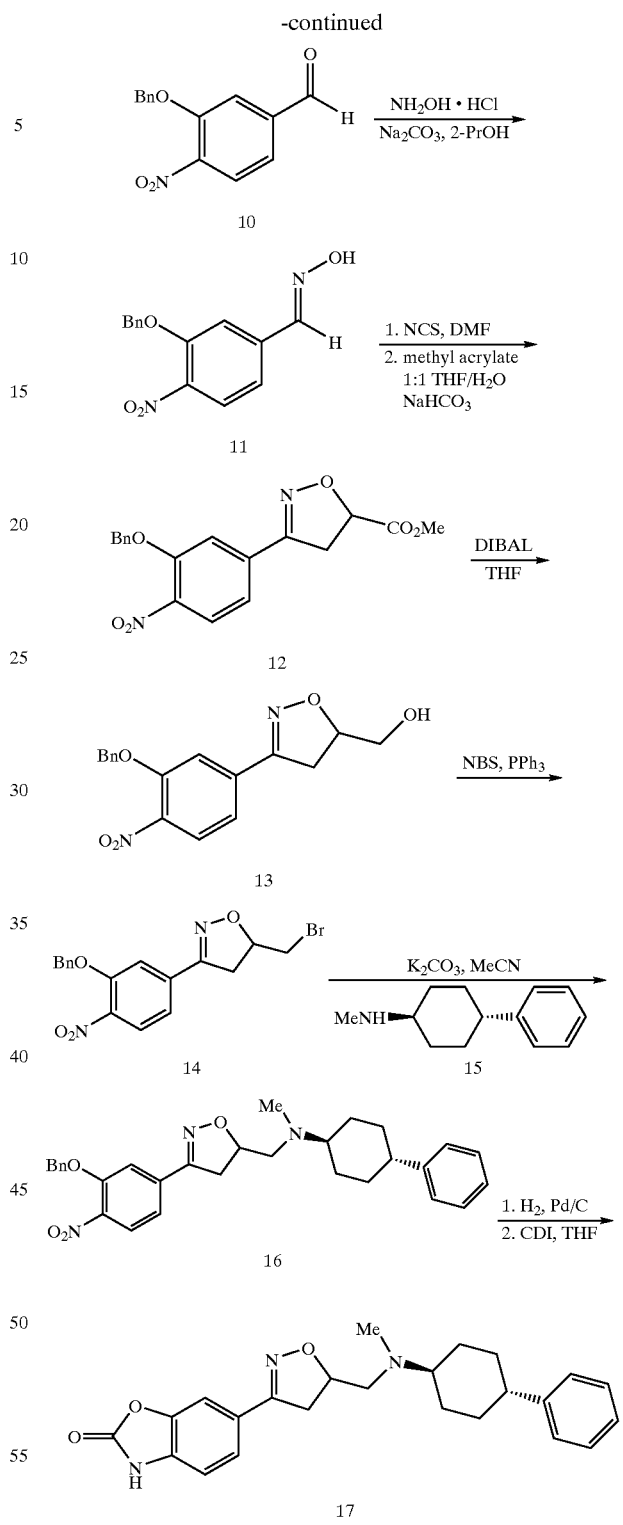

Step 1: A solution of aldehyde of formula 9 (10.4 g, 62.1 mmol), benzyl bromide (7.4 mL, 62.1 mmol), and K₂CO₃ (9.4 g, 68.3 mmol) in CH₃CN (200 mL) was stirred overnight at 40° C. After cooling to room temperature, the mixture was filtered, and the filtrate was concentrated under reduced pressure. The residue was dissolved in $CH_2Cl_2$ and treated with activated charcoal. Concentration under reduced pressure gave aldehyde of formula 10 as an orange oil that solidified over time while drying under high vacuum. The crude product was used without further purification: $^1$H NMR (500 MHz, $CDCl_3$) δ 10.06 (s, 1H), 7.97 (d, J=8 Hz, 1H), 7.69 (d, J=1 Hz, 1H), 7.58 (dd, J=8, 1 Hz, 1H), 7.51 (d, J=8 Hz, 2H), 7.44 (dd, J=8, 8 Hz, 2H), 7.40–7.30 (m, 1H), 5.35 (s, 2H).

Step 2: A solution of aldehyde of formula 10 (62.1 mmol) from Step 1, $NH_2OH \cdot HCl$ (4.32 g, 62.1 mmol), and $Na_2CO_3$ (13.2 g, 124 mmol) in 2-PrOH (60 mL) was stirred for 1 hour at 40° C. The mixture was concentrated under reduced pressure and the residue partitioned between EtOAc and $H_2O$. The organic layer was dried ($Na_2SO_4$) and concentrated under reduced pressure to give oxime of formula 11 (16.17 g, 96%) as a yellow solid. The crude product was used without further purification: $^1$H NMR (500 MHz, $CDCl_3$) δ 8.09 (s, 1H), 7.86 (d, J=8 Hz, 1H), 7.72 (br s, 1H), 7.47–7.33 (m, 6H), 7.18 (d, J=9 Hz, 1H), 5.25 (s, 2H).

Step 3: A solution of oxime of formula 11 (7.76 g, 28.5 mmol) from Step 2 and freshly crystallized (from benzene) N-chlorosuccinimide (NCS, 3.80 g, 28.5 mmol) in N,N-dimethylformamide (DMF) (30 mL) was stirred at room temperature for 1 hour. The reaction was partitioned between EtOAc and $H_2O$. The organic layer was washed with saturated NaCl, dried ($Na_2SO_4$), and concentrated under reduced pressure. The residue was dissolved in 1:1 THF: $H_2O$ (30 mL). Sodium bicarbonate (7.20 g, 86.5 mmol) and methyl acrylate (2.3 mL, 37.0 mmol) were added, and the reaction mixture was stirred overnight. Note: After 30 minutes, a mild exotherm occurred. The reaction was diluted with EtOAc, and the organic layer was washed with saturated NaCl, dried ($Na_2SO_4$), and concentrated under reduced pressure to give ester of formula 12 (4.56 g, 45%) as a yellow oil: $^1$H NMR (500 MHz, $CDCl_3$) δ 7.87 (d, J=9 Hz, 1H), 7.58 (d, J=2 Hz, 1H), 7.48 (d, J=8 Hz, 2H), 7.39 (dd, J=8, 8 Hz, 2H), 7.35–7.31 (m, 1H), 7.19 (dd, J=9, 2 Hz, 1H), 5.26 (s, 2H), 5.24 (dd, J=12, 7 Hz, 1H), 3.83 (s, 3H), 3.61 (ddd, J=17, 12, 7 Hz, 2H).

Step 4: Ester of formula 12 (1.00 g, 2.80 mmol) from Step 3 was dissolved in hot THF (25 mL) and the solution cooled in an ice bath. Diisobutyl aluminum hydride (DIBAL) (5.60 mL of a 1.0 M solution in cyclohexane, 5.60 mmol) was added, and the reaction was stirred for 45 minutes. The reaction was diluted with MeOH (2 mL) and a saturated aqueous solution of Rochelle's salt (25 mL) was added. After stirring briefly, EtOAc was added and the solution continued to stir for several hours. The organic layer was dried ($Na_2SO_4$) and concentrated under reduced pressure. Purification by chromatography (silica gel, 5:95 to 1:9 MeOH: $CH_2Cl_2$) gave alcohol of formula 13 (721 mg, 79%) as a yellow solid: $^1$H NMR (500 MHz, $CDCl_3$) δ 7.82 (d, J=8 Hz, 1H), 7.51 (d, J=2 Hz, 1H), 7.43 (d, J=8 Hz, 2H), 7.36 (dd, J=8, 8 Hz, 2H), 7.31–7.29 (m, 1H), 7.15 (dd, J=8, 2 Hz, 1H), 5.20 (s, 2H), 4.87 (dddd, J=10, 8, 5, 4 Hz, 1H), 3.88 (dd, J=12, 4 Hz, 1H), 3.68 (dd, J=12, 5 Hz, 1H), 3.27 (ddd, J=16, 10, 8 Hz, 2H), 2.50 (br s, 1H).

Step 5: Triphenyl phosphine (6.00g, 22.8 mmol) and N-bromosuccinimide (4.0 g, 22.8 mmol) were added to an ice-cold solution of alcohol of formula 13 (5.72 g, 18.3 mmol) from Step 4 in THF (50 mL), and the solution was stirred for 1 hour. The mixture was partitioned between EtOAc and satd $NaHCO_3$. The organic layer was washed with satd NaCl, dried ($Na_2SO_4$), and concentrated under reduced pressure. Purification by chromatography (silica gel, 1:4 to 1:1 EtOAc: hexanes) gave bromide of formula 14 (4.37 g, 65%) as a yellow solid: $^1$H NMR (500 MHz, $CDCl_3$) δ 7.87 (d, J=8 Hz, 1H), 7.56 (d, J=2 Hz, 1H), 7.45 (d, J=8 Hz, 2H), 7.39 (dd, J=8, 8 Hz, 2H), 7.34–7.31 (m, 1H), 7.19 (dd, J=8, 2 Hz, 1H), 5.25 (s, 2H), 4.97 (dddd, J=10, 7, 6, 4 Hz, 1H), 3.59 (dd, J=10, 4 Hz, 1H), 3.44 (ddd, J=17, 10, 6 Hz, 1H), 3.29 (dd, J=17, 7 Hz, 2H).

Step 6: A mixture of bromide of formula 14 (400 mg, 1.02 mmol) from Step 5, amine of formula 15, prepared as described in Preparation 2 (215 mg, 0.930 mmol), and $K_2CO_3$ (465 mg, 3.37 mmol) in acetonitrile (15 mL) was heated under reflux overnight. After cooling to room temperature, the reaction mixture was concentrated under reduced pressure and then partitioned between EtOAc and water. The organic layer was dried ($Na_2SO_4$), filtered, and concentrated under reduced pressure. Purification by flash chromatography (silica gel, 5:1 EtOAc: hexanes) gave amine of formula 16 (210 mg, 40%), as a pale yellow solid: $^1$H NMR (500 MHz, DMSO-$d_6$) δ 7.97 (d, J=9 Hz, 1H), 7.61 (s, 1H), 7.48–7.35 (m, 10H), 7.21 (d, J=9 Hz, 1H), 5.28 (s, 2H), 5.25 (m, 1H), 3.64–3.32 (m, 4H), 3.28 (m, 1H), 2.82 (s, 3H), 2.64 (m, 1H), 2.21 (br d, J=9 Hz, 2H), 2.11 (br d, J=9 Hz, 2H), 1.75 (dddd, J=9, 9, 9, 2 Hz, 2H), 1.45 (dddd, J=9, 9, 9, 2 Hz, 2H).

Step 7: A mixture of amine of formula 16 (210 mg, 0.421 mmol) from Step 6 and 10% Pd/C (50 mg) in 1:1 THF:MeOH (20 mL) was shaken under an atmosphere of $H_2$ (g) at 50 psi for 32 hours. The reaction mixture was filtered through CELITE and concentrated under reduced pressure to give an unstable solid. While maintaining an atmosphere of $N_2$, the solid was quickly taken up in THF (5 mL), 1,1'-carbonyldiimidazole (CDI) (103 mg, 0.632 mmol) was added, and the resultant mixture heated under reflux for 2 hours. After cooling to room temperature, the mixture was diluted with EtOAc and washed with water. The organic layer was dried ($Na_2SO_4$), filtered, and concentrated under reduced pressure. Purification by flash chromatography (silica gel, 4:1 $CH_2Cl_2$:MeOH) and conversion to the HCl salt according to the above general method gave trans-6-(5-{[methyl-(4-phenyl-cyclohexyl)-amino]-methyl}-4,5-dihydro-isoxazol-3-yl)-3H-benzoxazol-2-one hydrochloride as a tan solid (70 mg, 37%): mp 270–274° C.; IR (KBr): 3433, 3095, 1772 cm$^-$; $^1$H NMR (500 MHz, DMSO-$d_6$) δ 9.08 (s, 1H), 7.72 (s, 1H), 7.32 (d, J=8 Hz, 1H), 7.29–7.08 (m, 6H), 5.24 (m, 2H), 3.97 (m, 1H), 3.39–3.14 (m, 4H), 2.85 (s, 3H), 2.12 (m, 2H), 1.94 (m, 2H), 1.57 (m, 2H), 1.51 (m, 2H); CI-MS (methane) (m/z): 406 [M+H]$^+$; HRMS-API (m/z): [M+H]$^+$ calcd for $C_{24}H_{27}N_3O_3$, 406.2130; found, 406.2136; HPLC: method A, 6.05 minutes (96.5%); method B, 10.96 minutes (95.6%).

EXAMPLE 2 trans-6-{4-[Methyl-(2-methyl-5-phenyl-furan-3-ylmethyl)-amino]-cyclohexyl}-3H-benzoxazol-2-one (21)

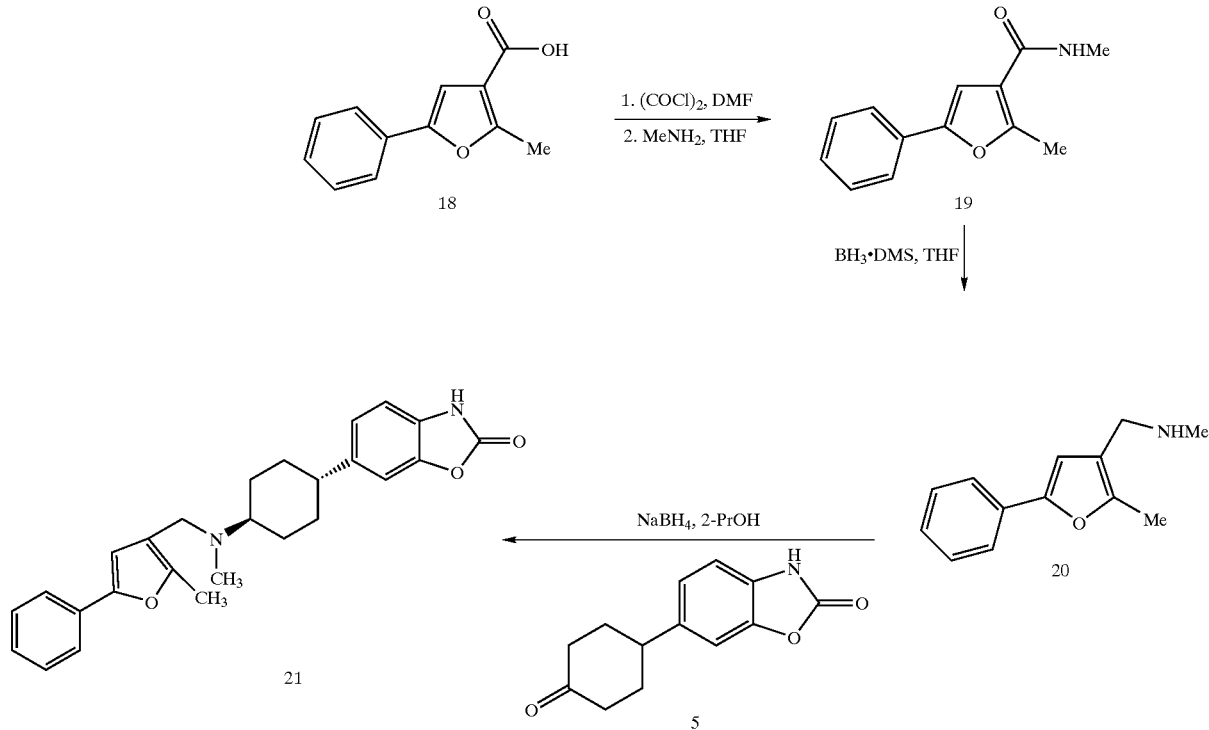

Step 1: To an ice-cold, stirred solution of oxalyl chloride (1.25 g, 9.89 mmol) in $CH_2Cl_2$ (15 mL) was added DMF (100 mg, 1.37 mmol). After stirring for 10 minutes, a solution of 2-methyl-5-phenylfuranoic acid (18) (1.0 g, 4.95 mmol) in $CH_2Cl_2$ (20 mL) was added, and stirring was continued for 2 hours. The reaction mixture was concentrated under reduced pressure and then taken up in THF (15 mL). After cooling to 0° C., methylamine (5.44 mL, 10.87 mmol) was added, and the mixture was stirred for 30 minutes, and then poured into water. The aqueous solution was extracted with EtOAc. The organic layer was dried ($Na_2SO_4$), filtered, and concentrated under reduced pressure to give amide of formula 19 (1.0 g, 94%), as a white solid: $^1$H NMR (500 MHz, $CDCl_3$) δ 7.61 (d, J=8 Hz, 2H), 7.38 (t, J=8 Hz, 2H), 7.27 (m, 1H), 6.62 (s, 1H), 5.81 (br s, 1H), 2.90 (d, J=5 Hz, 3H), 2.66 (s, 3H).

Step 2: To an ice-cold, stirred solution of amide of formula 19 (1.0 g, 4.65 mmol) from Step 1 in THF (20 mL) was added borone-dimethylsulfide ($BH_3$-DMS) (2.56 mL of a 2.0 M solution in THF, 5.12 mmol). The reaction mixture was stirred at room temperature overnight, and then at 40° C. for 3 hours. After cooling to room temperature, MeOH was added, and the resultant mixture was concentrated under reduced pressure. The crude product was diluted with MeOH (10 mL) and treated with excess HCl (1N in $Et_2O$). Concentration under reduced pressure, followed by purification by flash chromatography (silica gel, 9:1:0.1 $CH_2Cl_2$:MeOH:$NH_4OH$) gave amine of formula 20 (458 mg, 49%) as a clear oil: $^1$H NMR (500 MHz, $CDCl_3$) δ 7.60 (d, J=9Hz, 2H), 7.34 (t, J=9 Hz, 2H), 7.20 (m, 1H), 6.59 (s, 1H), 3.69 (br s, 1H), 3.54 (s, 2H), 2.45 (s, 3H), 2.33 (s, 3H).

Step 3: A mixture of amine of formula 20 (458 mg, 2.28 mmol) from Step 2, ketone of formula 5, prepared above in Preparation 1, (526 mg, 2.28 mmol), and 3A molecular sieves in 2-PrOH (20 mL) was stirred for 4 hours. $NaBH_4$ (121 mg, 3.19 mmol) was added, and stirring was continued overnight. Concentration under reduced pressure, followed by purification by flash chromatography (silica gel, 97:3:1 $CH_2Cl_2$:MeOH:$NH_4OH$), and conversion to the HCl salt following the general procedure described above, gave trans-6-{4-[methyl-(2-methyl-5-phenyl-furan-3-ylmethyl)-amino]-cyclohexyl}-3H-benzoxazol-2-one (21) (405 mg, 43%), as a white solid: mp 176–183° C.; IR (KBr): 2934, 1771 $cm^{-1}$; $^1$H NMR (500 MHz, DMSO-$d_6$) δ 7.64 (d, J=7 Hz, 2H), 7.44 (t, J=7 Hz, 2H), 7.20 (m, 1H), 7.01 (s, 1H), 6.99 (m, 3H), 4.25 (m, 1H), 4.10 (m, 1H), 3.28 (m, 1H), 3.21 (m, 1H), 2.69 (s, 3H), 2.58 (s, 3H), 1.89 (m, 2H), 1.80 (m, 2H), 1.45 (m, 2H), 1.25 (m, 2H); CI-MS (methane) (m/z): 417 $[M+H]^+$; HRMS-API (m/z): $[M+H]^+$ calcd for $C_{26}H_{28}N_2O_3$, 417.2178; found, 417.2166; HPLC: method A, 5.42 minutes (>99%); method B, 10.4 minutes (>99%); Analysis Calcd for $C_{26}H_{28}N_2O_3 \cdot HCl \cdot H_2O$: C, 66.30; H, 6.63; N, 5.95. Found: C, 66.12; H, 6.63; N, 5.72.

EXAMPLES 3a AND 3b 3a trans-(R)-6-{4-[2-Oxo-3-phenyl-oxazolidin-5-ylmethyl)-amino]-cyclohexyl}-3H-benzoxazol-2-one (27) and 3b trans-(R)-6-{4-[Methyl-(2-oxo-3-phenyl-oxazolidin-5-ylmethyl)-amino]-cyclohexyl}-3H-benzoxazol-2-one (28)

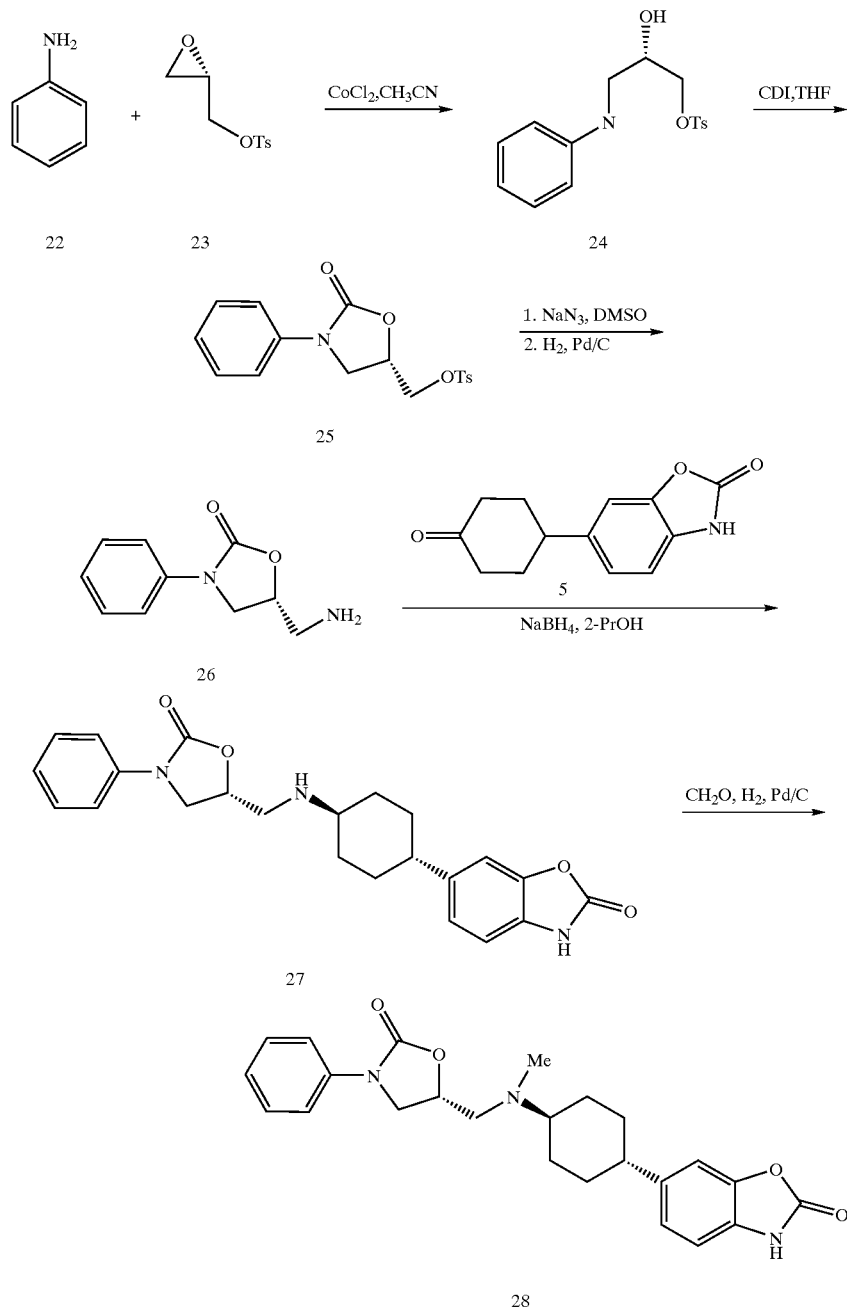

pressure, and the residue was dissolved in EtOAc. The solution was washed with saturated NaHCO$_3$, saturated NaCl, dried (Na$_2$SO$_4$), filtered and concentrated under reduced pressure. Purification by flash chromatography (silica gel, 1:4 to 1:2 EtOAc: hexanes) gave alcohol of formula 24 (1.84 g, 65%): $^1$H NMR (300 MHz, CDCl$_3$) δ 7.77 (d, J=8 Hz, 2H), 7.32 (d, J=8 Hz, 2H), 7.14 (dd, J=8, 8 Hz, 2H), 6.71 (dd, J=8, 8 Hz, 1H), 6.57 (d, J=8 Hz, 2H), 4.10–4.00 (m, 3H), 3.23 (dd, J=13, 4 Hz, 2H), 3.11 (dd, J=13, 6Hz, 2H), 2.42 (s, 3H).

Step 1: Anhydrous CoCl$_2$ (100 mg, 0.770 mmol) was added to a solution of 2S-(+)-glycidyl tosylate of formula 23 (2.02 g, 8.85 mmol) and aniline of formula 22 (810 μL, 8.85 mmol) in CH$_3$CN (25 mL). The mixture was stirred for 24 hours. The reaction solvent was removed under reduced Step 2: Carbonyl diimidazole (1.16 g, 7.17 mmol) was added to an ice cold solution of alcohol of formula 24 (1.84 g, 5.74 mmol) from Step 1 and Et$_3$N (2.0 mL, 14.3 mmol)

in THF (25 mL). The reaction solvent was evaporated under reduced pressure, and the residue was dissolved in EtOAc. The solution was washed with saturated NaHCO₃, saturated NaCl, dried (Na₂SO₄), filtered, and concentrated under reduced pressure. Purification by flash chromatography (silica gel, 3:7 to 2:3 EtOAc: hexanes) gave oxazolidinone of formula 25 (1.69 g, 85%) as a white solid: $^1$H NMR (300 MHz, CDCl₃) δ 7.78 (d, J=8 Hz, 2H), 7.47 (d, J=8 Hz, 2H), 7.39–7.33 (m, 4H), 7.15 (dd, J=8 Hz, 1H), 5.29–4.79 (m, 1H), 4.26–4.23 (m, 2H), 4.07 (dd, J=9, 9 Hz, 1H), 3.89 (dd, J=9, 6 Hz, 1H), 2.44 (s, 3H).

Step 3: Oxazolidinone of formula 25 (1.69 g, 4.87 mmol) and NaN₃ (633 mg, 9.74 mmol) were stirred at 80° C. in dimethylsulfoxide (DMSO) (5 mL) for 8 hours. The reaction mixture was partitioned between EtOAc and water. The organic layer was washed with saturated NaCl, dried (Na₂SO₄), filtered, and concentrated under reduced pressure. Purification by flash chromatography (silica gel, 2:5 EtOAc: hexanes) gave the corresponding azide (1.04 g, 98%): $^1$H NMR (300 MHz, CDCl₃) δ 7.55 (d, J=8 Hz, 2H), 7.39 (dd, J=8, 8 Hz, 2H), 7.16 (dd, J=8, 8 Hz, 1H), 4.82–4.74 (dddd, J=9, 9, 6, 5 Hz, 1H), 4.10 (dd, J=9, 9 Hz, 1H), 3.87 (dd, J=9, 6 Hz, 1H), 3.69 (dd, J=13, 5 Hz, 1H), 3.59 (dd, J=13, 5 Hz, 1H).

Step 4: A mixture of the azide from Step 3 (1.04 g, 4.77 mmol), acetic acid (350 μL, 5.96 mmol), CH₂Cl₂ (10 mL), MeOH (3 mL), and 20% Pd(OH)₂/C (100 mg) was shaken under a H₂ atmosphere at 50 psi overnight. The mixture was filtered, and the solvent was removed under reduced pressure. Purification by chromatography (silica gel, 1:9 to 1:5 MeOH: CH₂Cl₂) gave the amine of formula 26 (996 mg, 83%) as the acetic acid salt. $^1$H NMR (300 MHz, CD₃OD) δ 7.54 (d, J=8 Hz, 2H), 7.36 (dd, J=8, 8 Hz, 2H), 7.14 (dd, J=8, 8 Hz, 1H), 4.92–4.82 (m, 1H), 4.18 (dd, J=9, 9 Hz, 1H), 3.85 (dd, J=9, 6 Hz, 1H), 3.32–3.13 (m, 2H), 1.92 (s, 3H).

Step 5: A mixture of amine of formula 26 as the acetic acid salt (502 mg, 1.99 mmol), ketone of formula 5 (460 mg, 1.99 mmol), Et₃N (275 μL, 1.99 mmol), and 3 Å molecular sieves in a 1:1 solution of 2-PrOH:1,2-dichloroethane (10 mL) was stirred for 1 hour. NaBH₄ (121 mg, 3.19 mmol) was added, and stirring was continued overnight. Concentration under reduced pressure, followed by purification by flash chromatography (silica gel, 5:95 CH₂Cl₂:MeOH) and (silica gel, 1:5:2 MeOH:EtOAc:hexanes) gave trans-(R)-6-{4-[2-oxo-3-phenyl-oxazolidin-5-ylmethyl)-amino]-cyclohexyl}-3H-benzoxazol-2-one (27) (450 mg, 55%): $^1$H NMR (500 MHz, CD₃OD) δ 7.56 (d, J=8 Hz, 2H), 7.38 (dd, J=8, 8 Hz, 2H), 7.15 (dd, J=7, 7 Hz, 1H), 7.09 (s, 1H), 7.04 (d, J=8 Hz, 1H), 6.97 (d, J=8 Hz, 1H), 4.84–4.77 (m, 1H), 4.19 (dd, J=9, 9 Hz, 1H), 3.86 (dd, J=8, 8 Hz, 1H), 3.02 (d, J=6 Hz, 2H), 2.63 (dt, J=11, 6 Hz, 1H), 2.57 (dt, J=12, 6 Hz, 1H), 2.11 (d, J=11 Hz, 2H), 1.94 (d, J=12 Hz, 2H), 1.59–1.51 (m, 2H), 1.34–1.26 (m, 2H); CI-MS (m/z): 408 [M+H]⁺.

Step 6: A mixture of trans-(R)-6-{4-[2-oxo-3-phenyl-oxazolidin-5-ylmethyl)-amino]-cyclohexyl}-3H-benzoxazol-2-one of formula 27 (429 mg, 1.03 mmol) from Step 5, p-formaldehyde (300 mg, 10.0 mmol), CH₂Cl₂ (10 mL), MeOH (5 mL), water (5 mL), and 10% Pd/C (100 mg) was stirred under a balloon of H₂ for 2 days. The mixture was filtered, and the solvent was removed under reduced pressure. Purification by flash chromatography (silica gel, 89:10:1 CH₂Cl₂, MeOH, NH₄OH) followed by preparatory HPLC (method C) and conversion to the HCl salt according to the general procedure described above gave trans-6-{4-[methyl-((R)-2-oxo-3-phenyl-oxazolidin-5-ylmethyl)-amino]-cyclohexyl}-3H-benzoxazol-2-one hydrochloride (28) (218 mg, 47%): mp 211–223° C.; IR (KBr): 3415, 2942, 2657, 1762 cm⁻¹; $^1$H NMR (500 MHz, DMSO-d₆) δ 11.50 (s, 1H), 11.00 (br s, 0.5H), 10.35 (br s, 0.5H), 7.56 (dd, J=8, 8 Hz, 2H), 7.42 (dd, J=8, 8 Hz, 2H), 7.17 (s, 1H), 7.16 (dd, J=7, 7 Hz, 1H), 7.00 (s, 2H), 5.33–5.27 (m, 1H), 4.30–4.26 (m, 1H), 3.85–3.77 (m, 1H), 3.66–3.63 (m, 1H), 3.50–3.31 (m, 2H), 2.82 (s, 3H), 2.63–2.53 (m, 1H), 2.23–2.17 (m, 2H), 1.94 (d, J=10 Hz, 2H), 1.66–1.55 (m, 4H); CI-MS (m/z): 422 [M+H]⁺; HPLC: method A, 5.32 minutes (97.8%), method B, 9.89 minutes (>99%); Anal. Calcd for C₂₄H₂₇N₃O₄·HCl·0.25H₂O: C, 62.33; H, 6.21; N, 9.09. Found: C, 62.41; H, 6.16; N, 9.15.

EXAMPLES 4a AND 4b 4a trans-6-{5-[4-(4-Fluoro-phenyl)-cyclohexylamino]-methyl-2-oxo-oxazolindin-3-yl}-3H-benzoxazol-2-one (35)

4b trans-6-(5-{[4-(4-Fluoro-phenyl)-cyclohexyl]-methyl-amino}-methyl-2-oxo-oxazolindin-3-yl)-3H-benzoxazol-2-one (36)

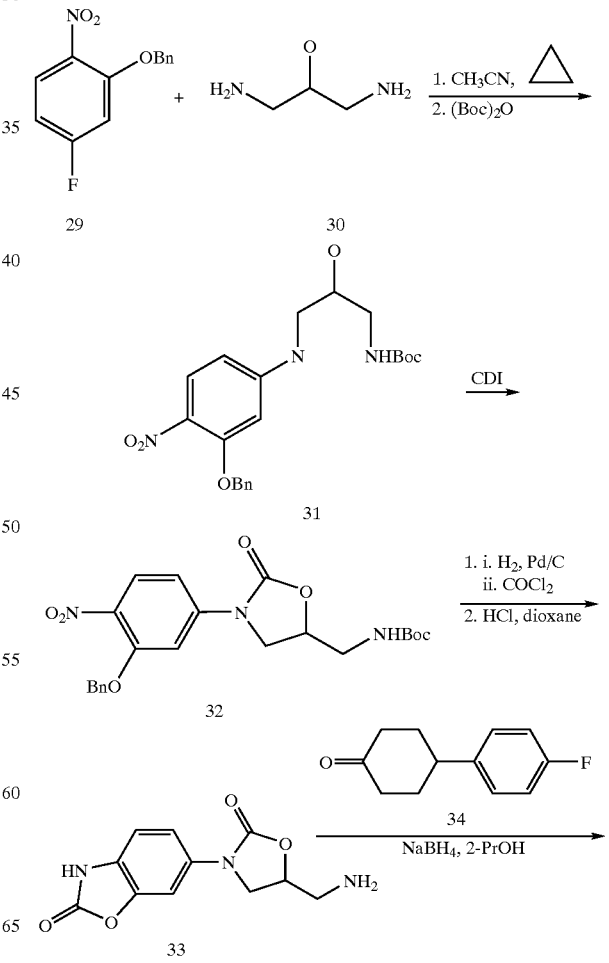

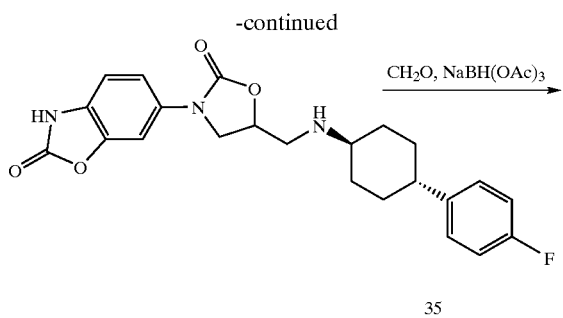

35

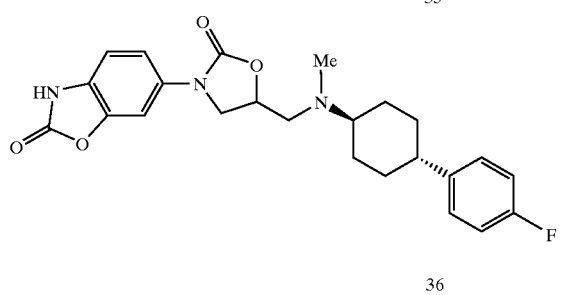

36

Step 1: A solution of fluoride of formula 29 (7.07 g, 28.6 mmol) and 1,3-diamino-2-propanol of formula 30 (2.58 g, 28.6 mmol) in $CH_3CN$ (50 mL) was stirred at reflux overnight. After cooling to room temperature, $NaHCO_3$ (2.40 g, 28.6 mmol), water (10 mL), and $(Boc)_2O$ were added and the mixture stirred for 2 hours. The reaction was diluted with EtOAc, and the organic layer was washed with satd NaCl, dried ($Na_2SO_4$), filtered, and concentrated under reduced pressure. Purification by flash chromatography (silica gel, 1:2 to 3:2 EtOAc: hexanes then 1:9 MeOH:$CH_2Cl_2$) gave alcohol of formula 31 (5.43 g, 46%): $^1$H NMR (500 MHz, $CDCl_3$) δ 7.97 (d, J=9 Hz, 1H), 7.50 (d, J=8 Hz, 2H), 7.39 (dd, J=8, 8 Hz, 2H), 7.31 (dd, J=8 Hz, 1H), 6.19–6.16 (m, 2H), 5.19 (s, 2H), 4.97 (br s, 1H), 4.89 (br s, 1H), 3.90–3.87 (m, 1H), 3.27–3.15 (m, 4H), 3.00 (br s, 1H), 1.46 (s, 9H).

Step 2: To a solution of alcohol of formula 31 (5.43 g, 13.0 mmol) from Step 1,4-(N,N-dimethylamino)pyridine (0.08 g, 0.65 mmol), $Et_3N$ (3.62 mL, 26.0 mmol) in THF (50 mL) was added CDI (2.32 g, 14.3 mmol), and the solution was heated to reflux for 2 hours. The reaction solvent was removed under reduced pressure. Purification by flash chromatography (silica gel, 2:4 to 3:2 EtOAc: hexanes) and (silica gel, 1:99 to 5:95 acetone: hexanes) gave oxazolidinone of formula 32 (4.61 g, 80%) as a pale yellow solid: $^1$H NMR (500 MHz, $CDCl_3$) δ 7.93 (d, J=9 Hz, 1H), 7.82 (br s, 1H), 7.49 (d, J=8 Hz, 2H), 7.38 (dd, J=8, 8 Hz, 2H), 7.30 (d, J=8 Hz, 1H), 6.79 (d, J=7 Hz, 1H), 5.23 (s, 2H), 5.00 (br s, 1H), 4.76–4.71 (m, 1H), 4.01 (dd, J=9 Hz, 1H), 3.84–3.80 (m, 1H), 3.50 (dd, J=5 Hz, 2H), 1.39 (s, 9H).

Step 3: A mixture of oxazolidinone of formula 32 (1.00 g, 2.25 mmol) and 10% Pd/C (150 mg) in THF (50 mL) was shaken under an atmosphere of $H_2$ at 50 psi for 3 hours. The reaction vessel was flushed with $N_2$, then $Et_3N$ (1.25 mL) and $COCl_2$ (1.20 mL of a 20% solution in toluene, 2.25 mmol) were added and the reaction stirred for 2 hours. The reaction was quenched with saturated $NaHCO_3$, filtered, and the THF removed under reduced pressure. The aqueous solution was extracted with EtOAc. The organic layer was dried ($Na_2SO_4$) and the solvent removed under reduced pressure. Purification by chromatography (silica gel 1:2 to 4:5 EtOAc: hexanes) gave a benzoxazolidinone intermediate (510 mg, 65%): $^1$H NMR (500 MHz, $CD_3OD+CDCl_3$) δ 7.59 (br s, 1H), 7.22 (d, J=8 Hz, 1H), 7.06 (d, J=8 Hz, 1H), 4.76–4.70 (m, 2H), 4.16–4.07 (m, 1H), 3.88–3.84 (m, 1H), 3.44 (br s, 2H), 1.41 (s, 9H); CI-MS (m/z): 350 $[M+H]^+$.

Step 4: Benzoxazolidinone intermediate of Step 3 (500 mg, 1.43 mmol) was stirred with anhydrous HCl (15 mL of a 4 M solution in dioxane, 60 mmol) for 1.5 hours. Concentration of the reaction solvent under reduced pressure followed by concentration from toluene (2×25 mL) gave amine of formula 33 (405 mg, 100%) as the HCl salt: $^1$H NMR (500 MHz, DMSO-$d_6$) δ 11.65 (br s, 1H), 8.43 (br s, 3H), 7.58 (d, J=2 Hz, 1H), 7.23 (dd, J=8, 2 Hz, 1H), 7.12 (d J=8 Hz, 1H), 4.98–4.93 (m, 1H), 4.18 (dd, J=9, 9 Hz, 1 H), 3.89 (dd, J=7 Hz, 1H), 3.24–3.20 (m, 2H).

Step 5: A mixture of amine of formula 33 as the HCl salt (420 mg, 1.47 mmol) from Step 4, ketone of formula 34 (425 mg, 2.21 mmol), 3 Å molecular sieves (200 mg), N-methylmorpholine (170 μL, 1.54 mmol), DMSO (10 mL), and 2-propanol were stirred for 2 hours. Sodium borohydride (56 mg, 1.47 mmol) was added, and the reaction was stirred overnight. The reaction was quenched with MeOH, filtered, and the reaction solvent removed under reduced pressure. The residue was partioned between EtOAc and water. A white solid formed and was collected by filtration. A suspension of the white solid in MeOH was treated with excess 1N HCl: $Et_2O$, and the resulting solution was concentrated under reduced pressure. Purification by flash chromatography (silica gel, 5:95 to 1:9 MeOH:$CH_2Cl_2$) gave a solid. The solid was dissolved in hot MeOH and then precipitated by the addition of $Et_2O$. The precipitated solid was collected by filtration to afford trans-6-{5-[4-(4-fluoro-phenyl)-cyclohexylamino]-methyl-2-oxo-oxazolidin-3-yl}-3H-benzoxazol-2-one (336 mg, 50%): mp 283–292° C.; IR (KBr): 2942, 1768, 1509 $cm^{-1}$; $^1$H NMR (500 MHz, DMSO-$d_6$) δ 11.67 (s, 1H), 9.55 (br s, 1H), 9.12 (br s, 1H), 7.60 (d, J=2 Hz, 1H), 7.30–7.24 (m, 3H), 7.13–7.08 (m, 3H), 5.12 (br s, 1H), 4.23 (dd, J=9, 9 Hz, 1H), 3.91–3.88 (m, 1H), 3.46–3.41 (m, 2H), 3.16 (m, 1H), 2.58–2.49 (m, 1H), 2.22 (d, J=11 Hz, 2H), 1.89 (d, J=11 Hz, 2H), 1.64–1.46 (m, 4H); API-MS (m/z): 426 $[M+H]^+$; HPLC: method A, 5.75 minutes (96.6%), method B, 13.21 minutes (>99%); Anal. Calcd for $C_{23}H_{24}FN_3O_4 \cdot HCl \cdot 0.5H_2O$: C, 58.66; H, 5.56; N, 8.92. Found: C, 58.88; H, 5.68; N, 8.91.

Step 6: To a stirred solution of trans-6-{5-[4-(4-fluoro-phenyl)-cyclohexylamino]-methyl-2-oxo-oxazolidin-3-yl}-3H-benzoxazol-2-one of formula 35 (235 mg, 0.509 mmol) from Step 5 in MeOH (7 mL), water (1 mL), and $CH_2Cl_2$ (3 mL) was added NaOH (510 μL of a 1N aqueous solution, 0.509 mmol) and p-formaldehyde (60 mg, 2.03 mmol). After 15 minutes, $NaBH(OAc)_3$ was added and stirring continued for 1 hour. Solid NaOH was added to give a clear solution which was then concentrated under reduced pressure. Purification by flash chromatography (silica gel, 5: 95 to 1:9 MeOH:$CH_2Cl_2$) gave the free amine. Conversion to the HCl salt by the general method described above gave trans-6-(5-{[4-(4-fluoro-phenyl)-cyclohexyl]-methyl-amino}-methyl-2-oxo-oxazolidin-3-yl)-3H-benzoxazol-2-one hydrochloride (36) (200 mg, 82%): mp 294–306° C.; IR (KBr): 3426, 2937, 2624, 1767, 1508 $cm^{-1}$; $^1$H NMR (500 MHz, DMSO-$d_6$) δ 11.71 (s, 2H), 10.69 (br s, 1H), 10.11 (br s, 1H), 7.60–7.58 (m, 2H), 7.28–7.23 (m, 6H), 7.14–7.09 (m, 6H), 5.30–5.23 (m, 2H), 4.28–4.23 (m, 2H), 3.83–3.75 (m, 3H), 3.63–3.61 (m, 2H), 3.45–3.36 (m, 3H), 2.85 (s, 3H), 2.84 (s, 3H), 2.58–2.52 (m, 2H), 2.20–2.11 (m, 4H), 1.94 (m, 4H), 1.70–1.51 (m, 8 H); API-MS (m/z): 440 $[M+H]^+$; HPLC: method A, 5.90 minutes (97.3%); Anal. Calcd for $C_{24}H_{26}FN_3O_4 \cdot HCl$: C, 60.57; H, 5.72; N, 8.83. Found: C, 60.50; H, 5.65; N, 8.72.

EXAMPLES 5a AND 5b 5a trans-6-{4-[(5-Methyl-2-phenyl-thiazol-4-ylmethyl)-amino]-cyclohexyl}-3H-benzoxazol-2-one (42) and 5b trans-6-{4-[Methyl-(5-methyl-2-phenyl-thiazol-4-ylmethyl)-amino]-cyclohexyl}-3H-benzoxazol-2-one (43)

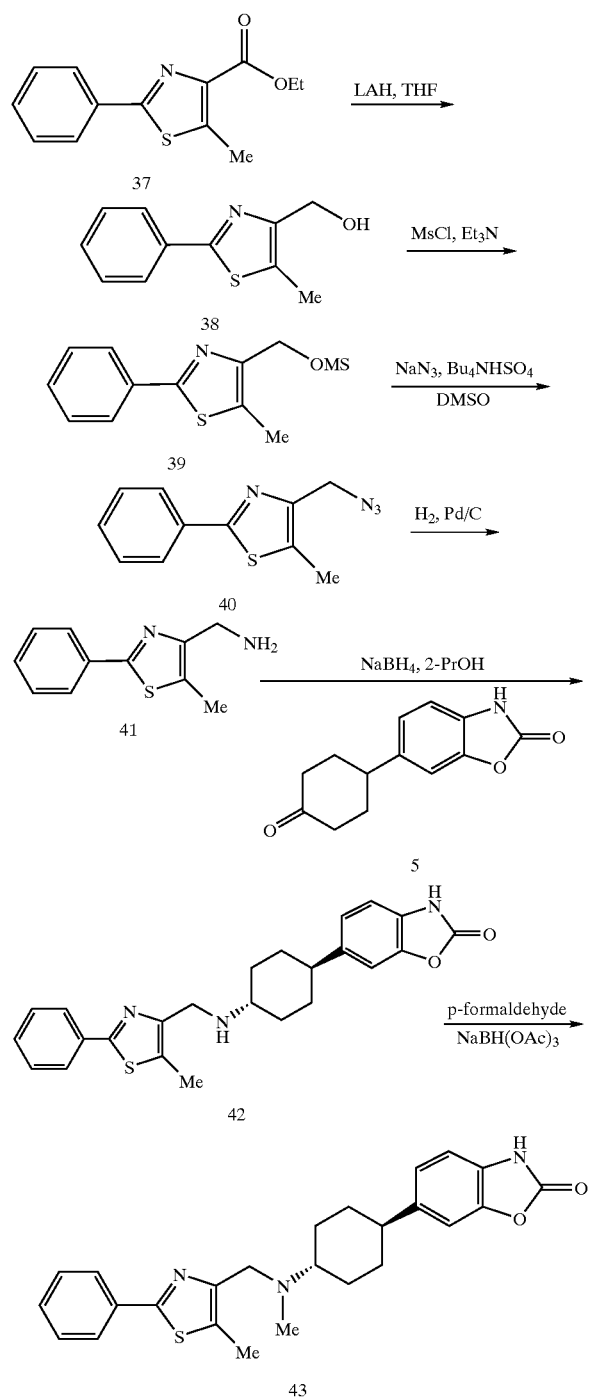

Step 1: To an ice-cold, stirred solution of ester of formula 37 (1.51 g, 6.11 mmol) in THF (40 mL) was added lithium aluminum hydride (LAH) (6.72 mL of a 1.0 M solution in Et$_2$O, 6.72 mmol), and the mixture was stirred for 1 hour. The reaction was quenched by the addition of water, 2N NaOH, and saturated NaCl. The organic layer was dried (Na$_2$SO$_4$), filtered, and concentrated under reduced pressure to give alcohol of formula 38 (1.22 g, 96%), as a white solid: $^1$H NMR (500 MHz, CDCl$_3$) δ 7.91 (m, 2H), 7.48 (m, 3H), 5.13 (s, 2H), 3.29 (s, 3H).

Step 2: To an ice cold, stirred solution of alcohol of formula 38 (1.2 g, 5.9 mmol) from Step 1 in CH$_2$Cl$_2$ (15 mL), was added Et$_3$N (888 mg, 8.78 mmol) and mesyl chloride (MsCl) (872 mg, 7.61 mmol). The reaction mixture was stirred for 1 hour, then washed with 2N HCl and saturated NaCl. The organic layer was dried (Na$_2$SO$_4$), filtered, and concentrated under reduced pressure to give mesylate of formula 39 (1.43 g, 86%), as a yellow solid: $^1$H NMR (500 MHz, CDCl$_3$) δ 7.93 (m, 2H), 7.46 (m, 3H), 5.36 (s, 2H), 2.59 (s, 3H), 2.51 (s, 3H).

Step 3: A mixture of mesylate of formula 39 (1.43 g, 5.05 mmol) from Step 2, sodium azide (657 mg, 10.1 mmol) and tetra(n-butyl)ammonium hydrogen sulfate (171 mg, 0.505 mmol) in DMSO (15 mL) was heated to 40° C. overnight. The reaction mixture was poured into ice water and extracted with EtOAc. The organic layer was dried (Na$_2$SO$_4$), filtered, and concentrated under reduced pressure to give azide of formula 40 (600 mg, 52%), as a clear oil: $^1$H NMR (500 MHz, CDCl$_3$) δ 7.91 (m, 2H), 7.42 (m, 3H), 4.74 (s, 2H), 2.56 (s, 3H).

Step 4: A mixture of azide of formula 40 (600 mg, 2.61 mmol) and 10% Pd/C (50 mg) and HCl (1 mL) in EtOH (20 mL) was shaken under an atmosphere of H$_2$ (g) at 50 psi for 3 hours. The reaction mixture was filtered through CELITE and concentrated under reduced pressure to give amine of formula 41 (532 mg, 96%) (HCl salt), as a white solid: $^1$H NMR (500 MHz, CDCl$_3$) δ 7.87 (m, 2H), 7.45 (m, 3H), 3.88 (s, 2H), 2.51 (s, 3H).

Step 5: A mixture of amine of formula 41 (410 mg, 2.00 mmol) from Step 4, ketone of formula 5 (464 mg, 2.00 mmol), and 3 Å molecular sieves in 2-PrOH (20 mL) was stirred for 3 hours, NaBH$_4$ (105 mg, 2.80 mmol) was added, and the mixture was stirred overnight. The reaction mixture was concentrated under reduced pressure. Purification by flash chromatography (silica gel, 95:5:1 CH$_2$Cl$_2$:MeOH:NH$_4$OH) gave trans-6-{4-[(5-methyl-2-phenyl-thiazol-4-ylmethyl)-amino]-cyclohexyl}-3H-benzoxazol-2-one (42) (510 mg, 56%), as a white solid: $^1$H NMR (500 MHz, DMSO-d$_6$) δ 9.18 (br s, 1H), 8.25 (br s, 1H), 7.97 (m, 1H), 7.46 (m, 5H), 7.19 (m, 1H), 7.04 (m, 1H), 4.43 (m, 1H), 4.21 (m, 1H), 3.10 (m, 1H), 2.58 (m, 1H), 2.46 (s, 3H), 2.23 (m, 2H), 1.94 (m, 2H), 1.49 (m, 4H).

Step 6: A mixture of trans-6-{4-[(5-methyl-2-phenyl-thiazol-4-ylmethyl)-amino]-cyclohexyl}-3H-benzoxazol-2-one of formula 42 (510 mg, 1.12 mmol), 2N NaOH (1 mL), and p-formaldehyde (168 mg, 5.60 mmol) in MeOH (10 mL) was stirred for 3 hours, NaBH(OAc)$_3$ (332 mg, 1,56 mmol) was added, and the mixture was stirred overnight. The reaction was quenched by addition of MeOH. Concentration under reduced pressure followed by purification by flash chromatography (silica gel, 95:5:1 CH$_2$Cl$_2$:MeOH:NH$_4$OH) gave trans-6-{4-[methyl-(5-methyl-2-phenyl-thiazol-4-ylmethyl)-amino]-cyclohexyl}-3H-benzoxazol-2-one (43) (345 mg, 71%), as a white solid: mp 246–248° C.; IR (KBr): 2927, 1773 cm$^{-1}$: $^1$H NMR (500 MHz, DMSO-d$_6$) δ 7.88 (dd, J=8, 2 Hz, 1H), 7.44 (m, 5H), 7.15 (s, 1H), 6.98 (m, 1H), 3.75 (s, 2H), 2.53 (m, 1H), 2.48 (m, 1H), 2.48 (s, 3H), 2.24 (s, 3H), 1.86 (m, 4H), 1.47 (m, 4H); CI-MS (methane) (m/z): 434 [M+H]$^+$; HRMS-API (m/z): [M+H]⁺ calcd for $C_{25}H_{27}N_3O_2S$, 434.1902; found, 434.1903; HPLC: method A, 12.46 minutes (99.0%); method B, 14.05 minutes (98.7%); Anal. Calcd for $C_{25}H_{27}N_3O_2S·0.25H_2O$: C, 68.54; H, 6.33; N, 9.59. Found: C, 68.21; H, 6.07; N, 9.59.

EXAMPLES 6a AND 6b 6a trans-6-(4-{[3-(4-Fluoro-phenyl)-4,5-dihydro-isoxazol-5-ylmethyl]-amino}-cyclohexyl)-3H-benzoxazol-2-one (51) and 6b trans-6-(4-{[3-(4-Fluoro-phenyl)-4,5-dihydro-isoxazol-5-ylmethyl]-methyl-amino}-cyclohexyl)-3H-benzoxazol-2-one (52)

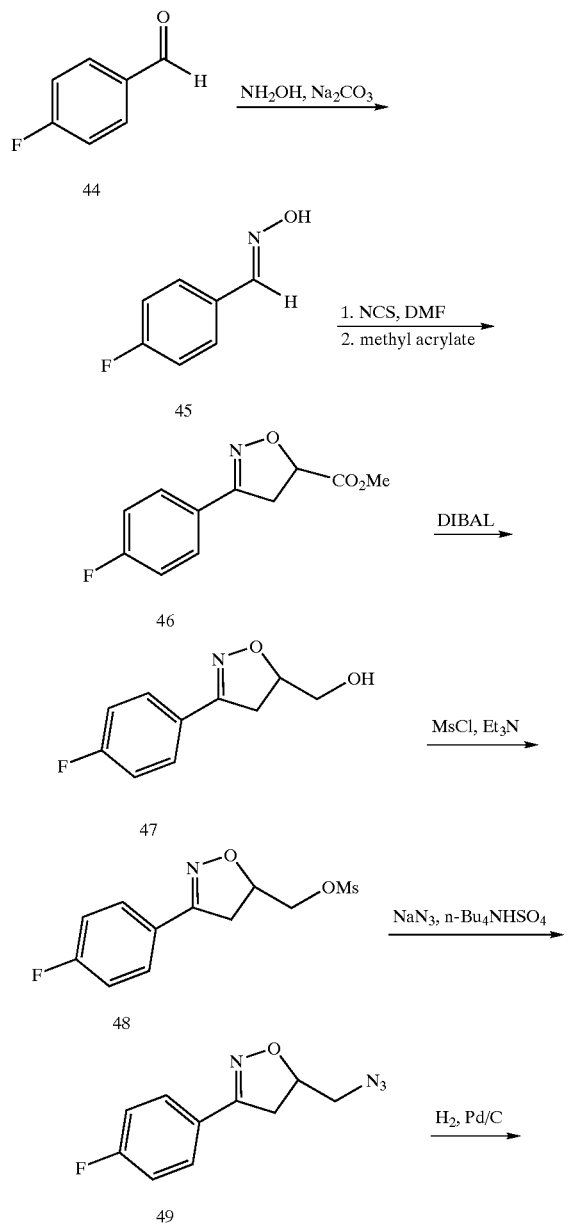

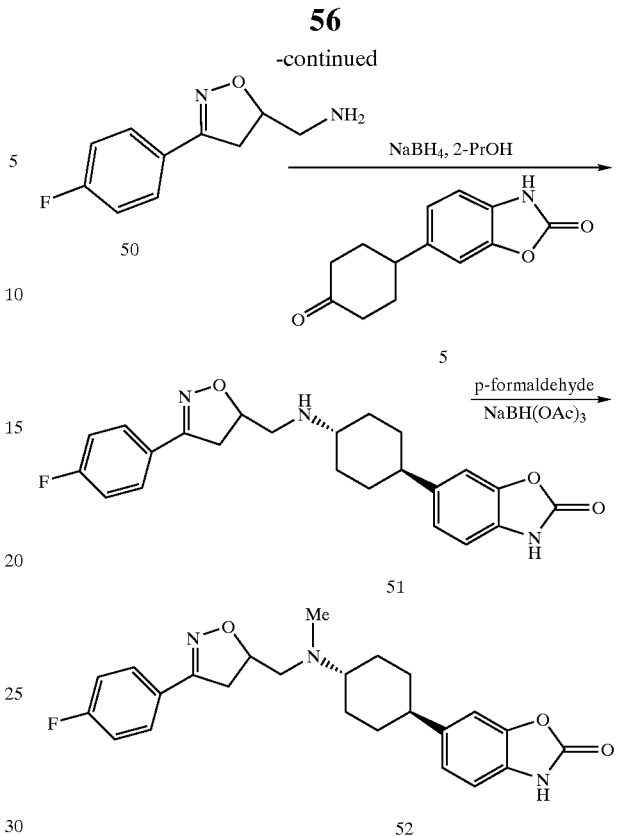

Step 1: A mixture of aldehyde of formula 44 (5.00 g, 40.3 mmol), hydroxylamine hydrochloride (3.36 g, 48.3 mmol), and sodium carbonate (9.40 g, 88.6 mmol) in 2-PrOH (80 mL) was heated to 40° C. overnight. After cooling to room temperature, the mixture was partitioned between EtOAc and water. The organic layer was dried ($Na_2SO_4$), filtered, and concentrated under reduced pressure to give oxime of formula 45 (5.03 g, 90%), as a white foam: ¹H NMR (500 MHz, DMSO-d₆) δ 11.19 (s, 1H), 8.13 (s, 1H), 7.64 (dd, J=6, 3 Hz, 2H), 7.24 (t, J=3 Hz, 2H).

Step 2: A mixture of oxime of formula 45 (5.03 g, 36.45 mmol) from Step 1 and NCS (4.87 g, 36.45 mmol) in DMF (70 mL) was stirred for 4 hours, then poured into EtOAc and water. The organic layer was washed with water (3×), dried ($Na_2SO_4$), filtered, and concentrated under reduced pressure to give a yellow oil. A mixture of the oil, methyl acrylate (4.08 g, 47.4 mmol) and $NaHCO_3$ (9.19 g, 109.4 mmol) in 1:1 THF:water (20 mL) was stirred overnight. The reaction mixture was diluted with EtOAc and washed with water. The organic layer was dried ($Na_2SO_4$), filtered, and concentrated under reduced pressure. Purification by flash chromatography (silica gel, 4:1 hexanes:EtOAc) gave ester of formula 46 (5.86 g, 73%), as a white solid: ¹H NMR (500 MHz, CDCl₃) δ 7.67 (dd, J=6,3 Hz, 2H), 7.10 (t, J=3 Hz, 2H), 5.17 (m, 1H), 3.81 (s, 3H), 3.62 (m, 2H).

Step 3: To an ice-cold, stirred solution of ester of formula 46 (5.78 g, 25.9 mmol) from Step 2 in THF (60 mL), was added DIBAL (23.6 mL of a 1.0 M solution in hexanes, 23.6 mmol). The reaction was stirred for 1.5 hours. An additional 2 equivalents of DIBAL were added, and stirring was continued overnight. The reaction was quenched with EtOAc and saturated Rochelle's salt, and the mixture was stirred until a clear solution formed. The organic layer was dried ($Na_2SO_4$), filtered, and concentrated under reduced pressure. Purification by flash chromatography (silica gel, 1:1 hexanes:EtOAc) gave alcohol of formula 47 (3.66 g, 72%), as a white solid: $^1$H NMR (500 MHz, DMSO-d$_6$) δ 7.72 (dd, J=6, 3 Hz, 2H), 7.29 (t, J=3 Hz, 2H), 4.94 (t, J=5 Hz, 1H), 4.71 (m, 1H), 3.52 (m, 2H), 3.40 (m, 1H), 3.27 (m, 1H); CI-MS (methane) (m/z): 196 [M+H]$^+$.

Step 4: To an ice-cold, stirred solution of alcohol of formula 47 (3.0 g, 15.4 mmol) from Step 3 in CH$_2$Cl$_2$ (45 mL) was added Et$_3$N (2.57 mL, 18.47 mmol), and MsCl (1.79 mL, 23.09 mmol), and the mixture was stirred for 25 minutes. The organic layer was washed with 1N HCl, dried (Na$_2$SO$_4$), filtered, and concentrated under reduced pressure to give mesylate of formula 48 as an oil, which was used immediately.

Step 5: A mixture of mesylate of formula 48 (4.20 g, 15.4 mmol) from Step 4, NaN$_3$ (2.00 g, 30.8 mmol), and tetra (n-butyl)ammonium hydrogen sulfate (523 mg, 1.54 mmol) in DMSO (15 mL) was heated to 40° C. overnight. After cooling to room temperature, the mixture was poured into water and extracted with EtOAc. The organic layer was dried (Na$_2$SO$_4$), filtered, and concentrated under reduced pressure. Purification by flash chromatography (silica gel, 2:1 hexanes:EtOAc) gave azide of formula 49 (2.23 g, 66%), as a yellow oil: $^1$H NMR (500 MHz, CD$_3$OD) δ 7.75 (dd, J=6, 3 Hz, 2H), 7.11 (t, J=3 Hz, 2H), 4.82 (m, 1H), 3.61–3.15 (m, 4H).

Step 6: A mixture of azide of formula 49 (2.20 g, 10.0 mmol) from Step 5, 10% Pd/C (100 mg), and concentrated. HCl (0.83 mL) in EtOH (30 mL) was shaken under an atmosphere of H$_2$ (g) at 50 psi for 3 hours. The reaction mixture was filtered through CELITE and treated with activated charcoal. The resulting mixture was filtered through CELITE, concentrated and converted to the HCl salt according to the general procedure describe above to give amine of formula 50 as the HCl salt (324 mg, 14%) as a white solid: $^1$H NMR (500 MHz, DMSO-d$_6$) δ 8.41 (br s, 3H), 7.73(dd, J=6, 3 Hz, 2H), 7.34 (t, J=3 Hz, 2H), 5.02 (m, 1H), 3.61–3.15 (m, 4H).

Step 7: A mixture of amine of formula 50 as the HCL salt (327 mg, 1.42 mmol) from Step 6, ketone of formula 5 (336 mg, 1.42 mmol) in 2-PrOH (30 mL) was stirred for 3 hours, NaBH$_4$ (75 mg, 1.99 mmol) was added, and the reaction mixture was stirred overnight. MeOH was added to quench the reaction, and the resulting mixture was concentrated under reduced pressure. Purification by flash chromatography (silica gel, 95:5:1 CH$_2$Cl$_2$:MeOH:NH$_4$OH) gave trans-6-(4-{[3-(4-fluoro-phenyl)-4,5-dihydro-isoxazol-5-ylmethyl]-amino}-cyclohexyl)-3H-benzoxazol-2-one (51) (190 mg, 33%), as a white solid: $^1$H NMR (500 MHz, DMSO-d$_6$) δ 7.73 (dd, J=6, 3 Hz, 2H), 7.34 (t, J=3 Hz, 2H), 7.17 (s, 1H), 6.98 (m, 3H), 4.84 (m, 1H), 3.38 (m, 2H), 3.19 (m, 2H), 2.84 (m, 2H), 1.88 (br d, J=8 Hz, 2H), 1.80 (br d, J=8 Hz, 2H), 1.36 (dddd, J=8, 8, 8, 2 Hz, 2H), 1.18 (dddd, J=8, 8, 8, 2 Hz, 2H).

Step 8: A mixture of trans-6-(4-{[3-(4-fluoro-phenyl)-4,5-dihydro-isoxazol-5-ylmethyl]-amino}-cyclohexyl)-3H-benzoxazol-2-one (51) (190 mg, 0.464 mmol) from Step 7, p-formaldehyde (70 mg, 2.32 mmol), and 2N NaOH (1 mL) in MeOH (15 mL) was stirred for 3 hours, NaBH(OAc)$_3$ (138 mg, 0.650 mmol) was added, and the reaction mixture was stirred overnight. Solid NaOH was added until the solution turned clear. The reaction mixture was concentrated under reduced pressure. Purification by flash chromatography (silica gel, 95:5:1 CH$_2$Cl$_2$:MeOH:NH$_4$OH) gave trans-6-(4-{[3-(4-fluoro-phenyl)-4,5-dihydro-isoxazol-5-ylmethyl]-methyl-amino}-cyclohexyl)-3H-benzoxazol-2-one (52) (60 mg, 31%), as a white foam: mp 109–114° C.; IR (KBr): 3430, 2927, 1772 cm$^{-1}$; $^1$H NMR (500 MHz, DMSO-d$_6$) δ 7.74 (dd, J=6, 3 Hz, 2H), 7.27 (m, 2H), 7.13 (s, 1H), 6.97 (m, 2H), 4.55 (m, 1H), 3.33 (m, 2H), 3.18 (m, 2H), 2.56 (m, 1H), 2.44 (m, 1H), 2.28 (s, 3H), 1.87 (m, 4H), 1.38 (m, 2H), 1.26 (m, 2H); API-MS (m/z): 424 [M+H]$^+$; HRMS-API (m/z): [M+H]$^+$ calcd for C$_{24}$H$_{26}$FN$_3$O$_3$, 424.2036; found, 424.2036; HPLC: method A, 5.39 minutes (98.1%); method B, 10.86 minutes (>99%).

As noted above, the invention compounds are subtype selective NMDA receptor antagonists. The compounds have been evaluated in standard assays commonly used to measure activity. Typical assays were carried out as follows.

BIOLOGICAL METHODS (I) Electrophysiological Assays at NMDA Receptor Subunits (in Vitro)

(a) The NR1A/NR2B Assay (i) Preparation of Subunit RNA's:

cDNA clones encoding the NR1A, NR2A, NR2B, and NR2C rat NMDA receptor subtypes are used (see, Moriyoshi et al., Nature (Lond.) 1991;354:31–37; Kutsuwada et al., Nature (Lond.) 1992;358: 36–41; Monyer et al., Science (Washington, D.C.) 1992;256: 1217–1221; Ikeda et al., FEBS Lett. 1992;313: 34–38; Ishii et al., J. Biol. Chem. 1993;268:2836–2843 for details of these clones or their mouse homologs). The clones are transformed into appropriate host bacteria and plasmid preparations are made with conventional DNA purification techniques. A sample of each clone is linearized by restriction; enzyme digestion of cRNA is synthesized with T3 RNA polymerase. The cRNA is diluted to 400 ng/μL and stored in 1 μL aliquots at −80° C. until injection.

(ii) The Xenopus Oocyte Expression System:

Mature female Xenopus laevis are anaesthetized (20–40 min) using 0.15% 3-aminobenzoic acid ethyl ester (MS-222) and from 2 to 4 ovarian lobes are surgically removed. Oocytes at developmental stages IV–VI (Dumont J. N., J. Morphol., 1972;136: 153–180) are dissected from the ovary still surrounded by enveloping ovarian tissues. Follicle-enclosed oocytes are micro-injected with 1:1 mixtures of NR1A:NR2A, 2B or 2C; injecting from 1 to 10 ng of RNA encoding each receptor subunit. NR1A encoding RNA is injected alone at ~20 ng. Oocytes are stored in Barth's medium containing (in mM): NaCl, 88; KC1, 1; CaCl$_2$, 0.41; Ca (NO$_3$)$_2$, 0.33; MgSO$_4$, 0.82 NaHCO$_3$, 2.4; HEPES 5, pH 7.4, with 0.11 mg/mL gentamicin sulphate. While oocytes are still surrounded by enveloping ovarian tissues, the Barth's medium is supplemented with 0.1% bovine serum. Oocytes are defolliculated from 1 to 2 days following injections by treatment with collagenase (0.5 mg/mL Sigma Type I for 0.5–1 hour)—(Miledi and Woodward, J. Phsyiol. (Lond.) 1989;416:601–621) and subsequently stored in serum-free medium.

(iii) Electrical Recordings:

Electrical recordings are made using a conventional two-electrode voltage clamp (Dagan TEV-200) over periods ranging from 3 to 21 days following injection (Woodward et al., Mol. Pharmacol., 1992;41: 89–103). Oocytes are placed in a 0.1 mL recording chamber continuously perfused (5–15 mL min$^{-1}$) with frog Ringer's solution containing (in mM): NaCl, 115; KCL, 2; BaCl$_2$, 1.8; HEPES, 5; pH 7.4. Drugs are applied by bath perfusion. Using oocytes expressing different subunit combinations of NMDA receptor, NMDA currents are activated by co-application of glutamate (100 μM) and glycine (1–100 μM) as agonists. Inhibitory potency of the novel antagonists of this invention is assessed on responses elicited by fixed concentrations of glutamate and glycine agonists, by measuring reductions in current induced by progressively increasing concentrations of invention compounds.

(iv) Concentration-inhibition Curves:

Concentration-inhibition curves were fitted with equation 1

$$I/I_{control} = 1/(1+([\text{antagonist}]/10^{-pIC_{50}})^n) \quad \text{Eq. 1}$$

in which $I_{control}$ is the current evoked by the agonists alone, $pIC_{50}=-\log IC_{50}$, $IC_{50}$ is the concentration of invention compound that produces half maximal inhibition of the electrical current, and n is the slope factor (see De Lean et al., *Am. J. Physiol.*, 1978;235:E97–102). For incomplete curves, analysis by fitting is unreliable, and $IC_{50}$ values are calculated by simple regression over linear portions of the curves using an ORIGIN software (Microcal Software, Boston, Mass.), a computer program for collection, analysis, and presentation of scientific data. The results of this assay may be reported as an $IC_{50}$ in micromolar ($\mu$M) concentration of invention compound.

(b) [$^3$H]Ifenprodil Binding Assay (IFPNR) Protocol:

(i) Materials:

Ifenprodil, [phenyl-$^3$H]-(specific activity, 66.2 Ci/mmol) was purchased from Dupont NEN Research Products (Boston, Mass.). Ifenprodil tartrate was purchased from Research Biochemicals International (Natick, Mass.). HEPES, glutamate, and glycine were purchased from Sigma Chemical Co. (St. Louis, Mo.).

(ii) Preparations:

All buffers and reagents used in assay incubations or to dissolve drugs were prepared using water purified through a Milli-Q reverse osmosis system (Millipore Corp., Bedford, Mass.) and treated with UV emissions. Prior to use in the assays buffers were further filtered through a sterile Corning filtration unit (Corning Glass Works, Corning, N.Y.) containing a 0.2 micron filter. Buffer used to rinse the membranes on the assay filters was prepared with purified water, but was not refiltered and was stored no longer than 5 days. Stock solutions of the drugs (usually 10 mM) were dissolved in 20 mM HEPES-KOH buffer pH 7.4 (assay buffer) with the addition of from 1 to 5 $\mu$L of glacial AcOH, if needed to keep them in solution. Eliprodil was used as the reference NMDA antagonist. A stock solution of eliprodil was prepared and was buffered with the addition of 10% DMSO. All subsequent dilutions from the stock solution were made in buffer.

An extensively washed buffy coat membrane fraction was prepared from frozen adult rat forebrains (Zivic-Miller Laboratories, Inc., Zelienople, Pa.) as described by Coughenour L. L., Cordon J. J., *J. Phannacol. Exp. Ther.*, 1997;280:584–592, and stored at $-80°$ C. On the day of the assay, pellets of the frozen membrane fractions were resuspended in 35 mL of assay buffer at pH 7.4 using a POLYTRON (Kinematica A.G. Company, Littau, Switzerland) mixer at setting 6. After incubation at 37° C. for 30 minutes in a shaking water bath, the homogenate was centrifuged 40,000×g for 10 minutes at 4° C. The pellets were resuspended in fresh buffer and centrifuged 3 more times before final suspension for use in the assay.

(iii) [$^3$H]Ifenprodil Binding Protocol:

Triplicate incubations were carried out in a volume of 0.5 mL in 1.3 mL polypropylene tubes (Marsh Biomedical Products Inc., Rochester, N.Y.) for 2 hours at room temperature. Incubations contained invention compounds, membranes (100–200 $\mu$g protein) and 4 nM [$^3$H]-ifenprodil in 20 mM HEPES-KOH buffer, pH 7.4 (assay buffer). Assays were started by addition of the membranes. Bound radioligand was separated by filtration under reduced pressure using a TOMTEC Mach II, 96 well cell harvester (Tomtec Inc, Orange, Conn.). Filtration was through Whatman GF/B glass fiber filters (Whatman Ltd., Maidstone, England), which had been soaked for at least 15 minutes in 0.3% polyethylenimine and allowed to air dry. The filters were rinsed with 3 mL of ice cold assay buffer within 6 seconds. Air was allowed to pass through the filters for an additional 10 seconds to remove residual moisture. The filter mat was supported on a cold ($-20°$ C.) TEFLON (E. I. Du Pont de Nemours and Company, Wilmington, Del.) coated support, and filters from individual wells were separated and placed in Mini Poly-Q vials (Beckman Instruments Inc., Fullerton, Calif.) and filled with 4 mL of scintillation cocktail (Beckman Ready Protein$^+$). Radioactivity retained on the filter was determined by liquid scintillation spectrophotometry. Nonspecific binding was defined as the binding in the presence of 1 mM ifenprodil. 90% of the total binding of ifenprodil was specific binding at the NR1A/NR2B NMDA receptor subtype active site (as opposed to binding at a remote site).

(iv) Data Analysis:

Binding curves were statistically analyzed for a best one- or two-site competition fit using GRAPHPAD PRISM software (GraphPad Software Inc., San Diego, Calif.), a computer program used to analyze and graph scientific data. The normalized data was fitted by nonweighted nonlinear regression to either $$y = \text{Bottom} + \frac{(\text{Top} - \text{Bottom})}{1 + 10^{x-LogEC_{50}}} \quad \text{or}$$

$$y = \text{Bottom} + (\text{Top} - \text{Bottom}) \frac{\text{Fraction-1}}{1 + 10^{x-LogEC_{50-1}}} + \frac{1-\text{Fraction-1}}{1 + 10^{x-LogEC_{50-2}}}$$

Control data was entered as 100%, and no parameters were constrained. Inhibition curves were compared by Anova with post-test comparisons of the $logIC_{50}$ with Dunnett's multiple comparisons post-test or Student's nonpaired, two-tailed t-test using GraphPad INSTAT (Harvey Motulsky, San Diego, Calif.) software.

The results of the IFPNR binding assay are reported in Table 1 in the column labeled "IFPNR" below as $IC_{50}$'s in micromolar ($\mu$M) concentrations.

TABLE 1

| Example | IFPNR $IC_{50}$ ($\mu$M) |
| --- | --- |
| 1 | 5.905 |
| 2 | 6.67 |
| 3a | N/A |
| 3b | 0.394 |
| 4a | >1 |
| 4b | >1 |
| 5a | N/A |
| 5b | 0.848 |
| 6a | N/A |
| 6b | 0.391 |

N/A means datum not available

As shown by the data in Table 1, the compounds of the invention are potent antagonists at the NMDA receptor.

In addition, certain animal models known to persons of ordinary skill in the pharmacology arts may be used to further characterize the compounds of the present invention. Examples of certain animal models useful in the present invention are described below.

(II) Animal Models:
(a) The Formalin Footpad Test (FT):

The FT model is used to test invention compounds for pain alleviating properties. The model produces a biphasic response in a test animal that results from a change in pain intensity over time. The FT model utilizes an injection of dilute formalin into the hindpaw of a rodent, which produces high intensity acute pain behaviors which are measured for the first 10 minutes post formalin injection (early phase responding). High intensity acute pain behaviors include rapid licking or biting of the injected hindpaw. The second phase is a prolonged period of lower intensity pain behaviors (late phase responding) which are measured from 11 to 45 minutes post formalin injection.

(i) Test Animals:

Male Wistar albino rats (Harlan Sprague-Dawley Labs) weighing approximately 100 g at the time of testing are used. Animals are group-housed and acclimated to the housing facility for 1 week prior to testing. Animals are maintained on a 12 hour/12 hour light/dark cycle and fed block rodent chow. From 4 to 8 animals are randomly assigned to either a vehicle only dose group or a vehicle plus invention compound treatment group on the day of testing.

(ii) Test Apparatus:

The testing apparatus is a 16 in.×8 in. box divided into two 8 in.×8 in. testing chambers. Each testing chamber comprises a floor and 3 walls made of clear plastic mirrors, and a fourth wall which is clear plastic that allowed observation of animal behavior. The top of each chamber is covered with a metal screen during testing to prevent animals from climbing out of the chamber. Two animals are tested simultaneously in the adjoining boxes, but animals are unable to observe one another.

(iii) Procedure:

Animals are weighed, and placed into holding cages (two animals per cage) in the testing room prior to dosing. Following approximately 30 minutes of acclimation to the testing room, to each pair of animals is administered orally (po) by gavage a mixture of invention compound plus vehicle or vehicle alone. The treated animals are then placed in individual test chambers, and allowed to acclimate to the chambers for at least 20 minutes. Then 50 $\mu$L of a 2.5% solution of formalin in vehicle is injected SC in the plantar surface of the left hindpaw from 30 to 120 minutes after administration of the invention compound. A session timer is started following the formalin injection, and the amount of time the animal spends licking or biting the injected paw is clocked with a hand-held stopwatch. The cumulative time spent engaging in a pain response is manually recorded at 5-minute intervals for 45 minutes post formalin injection. Early phase responding includes minutes 0 to 10, and late phase responding includes minutes 11 to 45. At the end of the testing period, animals are sacrificed using carbon dioxide.

(iv) Data Analysis:

As recited above, responding is divided into early phase (total time spent licking during minutes 0 to 10 following the formalin injection) behaviors and late phase (total time spent licking during minutes 11 to 45 post formalin injection) behaviors. Time values are obtained for the vehicle only dose group (the control group) and each treatment group. For the purpose of measuring the activity of the invention compounds, the late phase time values of a given treatment group are compared statistically to the late phase time values obtained for the control group using either Student's t-test or One-way Analysis of Variants (ANOVA).

The results are reported as the dose tested in milligrams of invention compound per kilogram of test animal (mg/kg).

A compound is characterized as active if it produced a statistically-significant decrease in the time animals administered invention compound plus vehicle spent engaging in pain-related behaviors compared to the time spent by animals receiving vehicle alone. Invention compounds are typically administered at 10 mg/kg and/or 30 mg/kg, and the activities are reported as either being greater than (>) or less than (<) these doses.

(b) The 6-OHDA Lesioned Rat Assay (6-OHDA):

The 6-OHDA model is used to test compounds of the invention for anti-Parkinsonism activity.

(i) 6-OHDA Lesioned Rat Assay Protocol:

6-Hydroxydopamine-lesioned rats are used (see Ungerstedt U., Arbuthnott G. W., Quantitative recording of rotational behavior in rats after 6-hydroxy-dopamine lesions of the nigrostraiatal dopamine system. *Brain Res.* 1971;24(3):485–493). Adult male Sprague-Dawley rats are anesthetized with chloral hydrate and unilateral lesions of the nigrostriatal dopamine system are accomplished by infusion of 8 $\mu$g of 6-hydroxydopamine HBr (6-OHDA) into the right medial forebrain bundle. Rats are pretreated 30 minutes before surgery with desipramine HCl 25 mg/kg intraperitoneally (IP) to protect noradrenergic neurons, and pargyline 25 mg/kg IP to potentiate the effects of 6-OHDA. A minimum of 3 weeks after surgery, the rotational behavior induced by apomorphine HCL 50 $\mu$g/kg administered subcutaneously (SC) is assessed. Only rats demonstrating more than 100 contraversive turns/hour to apomorphine are used for the present experiments.

(ii) Measurement of Animal Behavior:

Rotational behavior is measured using an automatic rotometer system (Rotorat Rotational Activity System, MED Associates, Georgia, Vt.). Anti-Parkinsonian activity is assessed as the ability of the invention compounds to potentiate the contraversive rotation induced by L-DOPA methyl ester, dosed at 10 mg/kg SC, over a 6-hour period. Experiments are conducted using a crossover paradigm where each rat received either vehicle plus L-DOPA, or an invention compound plus L-DOPA, in randomized order. Rats are tested at 7-day intervals. In experiments in which the invention compounds are tested orally (po), rats are food deprived for 16 hours.

(iii) Data Analysis:

Statistical analysis between treatment groups is performed using a paired t-test. The results are reported as the minimum effective dose (MED) in milligrams of invention compound per kilogram of test animal (mg/kg) required to produce a statistically-significant increase in total contraversive rotations in rats administered invention compound compared to rats receiving L-DOPA alone. Invention compounds are typically administered at 10 mg/kg and/or 30 mg/kg, and the MED's are reported as either being greater than (>) or less than (<) these doses.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I, or a compound of Formula VI or a corresponding pharmaceutically acceptable salt of a compound of Formula VI.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists or as agents for the treatment of diseases, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

EXAMPLE 7

Tablet Formulation:

| Ingredient | Amount (mg) |
| --- | --- |
| The compound of Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of disease caused by over excitation of NMDA receptor channel complexes.

EXAMPLE 8

Coated Tablets:

The tablets of Example 7 are coated in a customary manner with a coating of sucrose, potato starch, talc, tragacanth, and colorant.

EXAMPLE 9

Injection Vials:

The pH of a solution of 500 g of the compound of Example 4b and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the compound of Example 4b.

EXAMPLE 10

Suppositories:

A mixture of 25 g of the compound of Example 6b, 100 g of soya lecithin, and 1400 g of cocoa butter is fused, poured into molds, and allowed to cool. Each suppository contains 25 mg of the compound of Example 6b.

EXAMPLE 11

Solution:

A solution is prepared from 1 g of the compound of Example 5a, 9.38 g of $NaH_2PO_4.12H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Example 5a.

EXAMPLE 12

Ointment:

500 mg of the compound of Example 2 is mixed with 99.5 g of petroleum jelly under aseptic conditions. A 5 g portion of the ointment contains 25 mg of the compound of Example 2.

EXAMPLE 13

Capsules:

2 kg of the compound of Example 3a are filled into hard gelatin capsules in a customary manner such that each capsule contains 25 mg of the invention compound.

EXAMPLE 14

Ampoules:

A solution of 2.5 kg of the compound of Example 3b is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Example 3b.

While the forms of the invention exemplified herein such as, for example, the named species of Formulas I or VI and the recitation of treatment of Parkinson's constitute or pain presently preferred embodiments, many others are possible. It is not intended that said recited species of Formulas I or VI and preferred methods of use should, in any manner, limit or restrict the invention from the full scope as claimed herein.

Having described the present invention above, certain embodiments of the present invention are claimed as follows.

What is claimed is:

1. A compound of Formula VII

VII or pharmaceutically acceptable salts thereof, wherein

* means cis or trans or mixtures thereof;

$R_1$ is independently selected from alkyl, substituted alkyl, alkenyl, substituted alkenyl, alkoxy, substituted alkoxy, alkylaminoalkyl, hydroxyalkyl, (aminocarbonyl)-alkyl, (alkylthio)-alkyl, carboxyalkyl, haloalkyl, and halogen;

g is an integer of from 0 to 3;

R is hydrogen or alkyl;

d is 0;

B is a heterocyclene selected from the group consisting of:

X is O, S, or N—$R_3$ wherein $R_3$ is hydrogen or alkyl;

V is $CH_2$; and

—E—Y— is selected from the group consisting of
—CH=CH—N(H)—, —($CH_2$)$_2$—N(H)—,
—CH=N—N(H)—, —C(O)—$CH_2$—N(H)—,
—$CH_2$—C(O)—N(H)—, —$CH_2$S(O)—N(H)—,
—$CH_2$—S(O)$_2$—N(H)—, —CH=CH—CH(OH)—,
($CH_2$)$_2$—CH(OH)—, —C(O)—C(H)=C(OH)—,
—C(O)—N=C(OH)—, —N=CH—N(H)—,
—N(H)—C(O)—N(H)—, —O—C(O)—NH—,
—S—C(O)—NH—, —O—N=CH(OH)—,
—S—N=CH(OH)—, —N=N—N(H)—, —N=N—N(OH)—, —CH=CH—CH=C(OH)—, —($CH_2$)$_3$—CH(OH)—, —($CH_2$)$_2$—C(O)—N(H)—, —($CH_2$)$_2$—S(O)—N(H)—, —($CH_2$)$_2$—S(O)$_2$—N(H)—,
—CH=CH—C(O)—N(H)—, —C(O)—NH—N=C(OH)—, —CH=N—N=C(OH)—, —CH=N(O)—N=C(OH)—, —N(H)—C(O)—N=C(OH)—,
—N=CH—C(O)—NH—, —O—$CH_2$—C(O)—NH—, —S—$CH_2$—C(O)—NH— and —N(H)—C(O)—C(O)—N(H)—, 2. The compound according to claim 1 having the formula

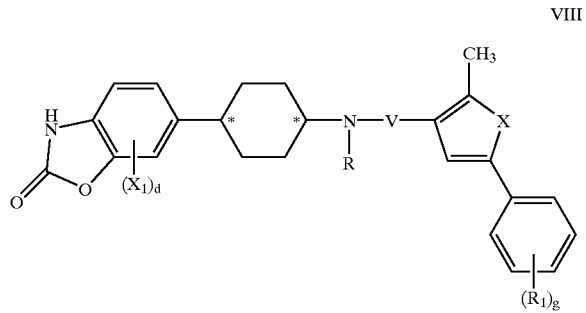

VIII or pharmaceutically acceptable salts thereof.

3. The compound according to claim 2 which is trans-6-{4-[methyl-(2-methyl-5-phenyl-furan-3-ylmethyl)-amino]-cyclohexyl}-3H-benzoxazol-2-one.

4. The compound according to claim 1 having the formula

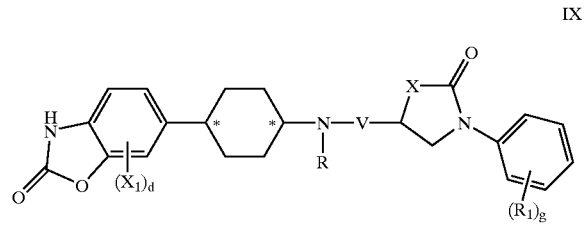

IX or pharmaceutically acceptable salts thereof.

5. The compound according to claim 4 selected from the group consisting of:

trans-(R)-6-{4-[(2-oxo-3-phenyl-oxazolidin-5-ylmethyl)amino]-cyclohexyl}-3H-benzoxazol-2-one; and trans-(R)-6-{4-[methyl-(2-oxo-3-phenyl-oxazolidin-5-ylmethyl)amino]-cyclohexyl}-3H-benzoxazol-2-one.

6. The compound according to claim 1 having the formula

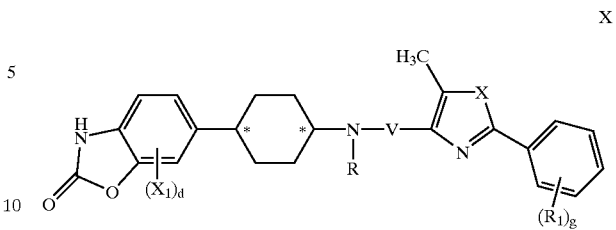

X or pharmaceutically acceptable salts thereof.

7. The compound according to claim 6 selected from the group consisting of:

trans-6-{4-[(5-methyl-2-phenyl-thiazol-4-ylmethyl)-amino]-cyclohexyl}-3H-benzoxazol-2-one; and trans-6-{4-(methyl-(5-methyl-2-phenyl-thiazol-4-ylmethyl)-amino]-cyclohexyl}-3H-benzoxazol-2-one.

8. The compound according to claim 1 having the formula

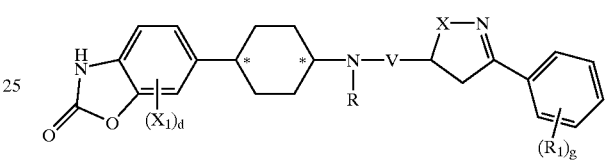

XI or pharmaceutically acceptable salts thereof.

9. The compound according to claim 8 selected from the group consisting of:

trans-6-(4-{[3-(4-fluoro-phenyl)-4,5-dihydro-isoxazol-5-ylmethyl]-amino}-cyclohexyl)-3H-benzoxazol-2-one; and trans-6-(4-{[3-(4-fluoro-phenyl)-4,5-dihydro-isoxazol-5-ylmethyl]-methyl-amino}-cyclohexyl)-3H-benzoxazol-2-one.

10. A pharmaceutical composition, comprising a therapeutically effective amount of a compound of Formula VII, or a pharmaceutically acceptable salt thereof, together with a pharmaceutically acceptable diluent, carrier, or excipient.

* * * * *